United States Patent
Maris et al.

(10) Patent No.: US 12,357,694 B2
(45) Date of Patent: Jul. 15, 2025

(54) METHODS AND COMPOSITIONS FOR USE OF TUMOR SELF-ANTIGENS IN ADOPTIVE IMMUNOTHERAPY

(71) Applicant: THE CHILDREN'S HOSPITAL OF PHILADELPHIA, Philadelphia, PA (US)

(72) Inventors: John M Maris, Philadelphia, PA (US); Mark Yarmarkovich, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 1248 days.

(21) Appl. No.: 16/979,138

(22) PCT Filed: Mar. 12, 2019

(86) PCT No.: PCT/US2019/021827
§ 371 (c)(1),
(2) Date: Sep. 8, 2020

(87) PCT Pub. No.: WO2019/178081
PCT Pub. Date: Sep. 19, 2019

(65) Prior Publication Data
US 2021/0213058 A1 Jul. 15, 2021

Related U.S. Application Data

(60) Provisional application No. 62/641,541, filed on Mar. 12, 2018.

(51) Int. Cl.
| | | |
|---|---|---|
| A61K 40/31 | (2025.01) | |
| A61K 40/11 | (2025.01) | |
| A61K 40/32 | (2025.01) | |
| A61K 40/42 | (2025.01) | |
| A61K 45/06 | (2006.01) | |
| C12N 9/12 | (2006.01) | |
| G01N 33/53 | (2006.01) | |
| G01N 33/569 | (2006.01) | |
| A61K 39/00 | (2006.01) | |

(52) U.S. Cl.
CPC .............. *A61K 45/06* (2013.01); *A61K 40/11* (2025.01); *A61K 40/32* (2025.01); *A61K 40/428* (2025.01); *C12N 9/1241* (2013.01); *G01N 33/5308* (2013.01); *G01N 33/56977* (2013.01); *A61K 2039/55522* (2013.01)

(58) Field of Classification Search
None
See application file for complete search history.

(56) References Cited

U.S. PATENT DOCUMENTS

| | | |
|---|---|---|
| 2003/0224424 A1 | 12/2003 | Garcia-Barcelo et al. |
| 2006/0073514 A1 | 4/2006 | Dedera et al. |
| 2011/0229504 A1 | 9/2011 | Fritsche et al. |
| 2016/0280757 A1* | 9/2016 | Mahr ...................... A61P 35/00 |
| 2017/0056486 A1 | 3/2017 | Mahr et al. |
| 2017/0080070 A1 | 3/2017 | Weinschenk et al. |
| 2017/0342125 A1* | 11/2017 | Mahr ..................... C07K 16/30 |
| 2018/0028634 A1 | 2/2018 | Chen |

FOREIGN PATENT DOCUMENTS

| | | | |
|---|---|---|---|
| JP | WO 13/061594 | * | 5/2001 |
| WO | WO 2004/007770 | | 1/2004 |
| WO | WO 2004/031409 | | 4/2004 |
| WO | WO 07/150077 | * | 12/2007 |
| WO | WO 2016/102272 | | 6/2016 |
| WO | WO 2016/156202 | | 10/2016 |
| WO | WO 17/184590 | * | 10/2017 |
| WO | WO 2017/202806 | | 11/2017 |

OTHER PUBLICATIONS

Essand et al., J. Internal Med., 2013, 273: 166-181.*
Deniger et al., Mol. Ther., 2016, 24: 1078-1089.*
Sequence alignment_4, 2024.*
Sequence alignment_8, 2024.*
Sequence alignment_24, 2024.*
Sequence alignment_6, 2024.*
European Search Report for EP 22209212 dated May 9, 2023, 14 pages.
Regadas et al., "Several Cis-regulatory Elements Control mRNA Stability, Translation Eficiency, and Expression Pattern of Prrxll (Paird Related Homeobox Protein-Like 1)", *Journal of Biological Chemistry*, 288(51): 36285-36301, Dec. 20, 2013.
Santa Cruz Biotechnology, "Phox2b (B-11): sc-376997" Jan. 1, 2023.
Son et al., "Database of mRNA gene expression profiles of multiple human organs", *Genome Research, Cold Spring Harbor Laboratory Press, US*, 15(3): 443-450, Mar. 1, 2005.
Yang et al., "PHOX2B Is Associated with Neuroblastoma Cell Differentiation", *Cancer Biotherapy & Radiopharmaceuticals*, 31(2): 44-51, Mar. 1, 2016.
Japanese Office Action for JP Appl. No. 2020-548676 dated Apr. 4, 2023, with English translation.
Abelin et al., "Mass Spectrometry Profiling of HLA-Associated Peptidomes in Mono-allelic Cells Enables More Accurate Epitope Prediction," *Immunity*, 46(2):315-326 2017.
Alexandrov et al., "Signatures of mutational processes in human cancer," *Nature*, 500(7463):415-421, 2013.
Himoudi et al., "MYCN as a target for cancer immunotherapy," *Cancer Immunology, Immunotherapy*, 57(5):693-70, 2008.
Lohmueller et al., "Current modalities in cancer immunotherapy: Immunomodulatory antibodies, CARs and vaccines," *Pharmacology & Therapeutics*, 178:31-47, 2017.
Marty et al., "MHC-I Genotype Restricts the Oncogenic Mutational Landscape," *Cell*, 171(6):1272-1283, 2017.

(Continued)

*Primary Examiner* — Ileana Popa
(74) *Attorney, Agent, or Firm* — Parker Highlander PLLC

(57) ABSTRACT

The present disclosure provides methods and compositions for immunotherapy employing a modified T cell or NK cell comprising a receptor that binds to newly identified tumor antigens that can be administered to patients for disease (e.g., cancer) treatment. Also described are polynucleotides and vectors encoding the same.

13 Claims, 6 Drawing Sheets

Specification includes a Sequence Listing.

(56) References Cited

OTHER PUBLICATIONS

PCT International Invitation to Pay Additional Fees issued in International Application No. PCT/US2019/021827, dated Jun. 3, 2019.
PCT International Search Report and Written Opinion issued in International Application No. PCT/US2019/021827, dated Jul. 25, 2019.
Rech et al., "Tumor immunity and survival as a function of alternative neopeptides in human cancer," *Cancer Immunol. Res.*, 6(3):276-287, 2018.
Rooney et al., "Molecular and genetic properties of tumors associated with local immune cytolytic activity," *Cell*, 160(1-2):48-61, 2015.
Tilan and Kitlinska, "Neuropeptide Y (NPY) in tumor growth and progression: Lessons learned from pediatric oncology," *Neuropeptides*, 55:55-66, 2016.
Winograd et al., "Induction of T-cell Immunity Overcomes Complete Resistance to PD-1 and CTLA-4 Blockade and Improves Survival in Pancreatic Carcinoma," *Cancer Immunology Research*, 3(4):399-411, 2015.
Yarmarkovich et al., "Abstract No. 5824: MHC class I immunogenicity and novel tumor antigen discovery in neuroblastoma [abstract]," In: Proceedings of the American Association for Cancer Research Annual Meeting, Washington, D.C., Apr. 1-5, 2017.
Nelson et al., "Novel immunotherapies for hematologic malignancies," *Immunological Reviews*, 263(1):90-105, 2014.
Office Communication issued in European Patent Application No. 1976795.7, dated Jan. 20, 2022.
Restifo et al., "Adoptive immunotherapy for cancer: harnessing the T cell response," *Nature Revies Immunology*, 12(4):269-281, 2012.

\* cited by examiner

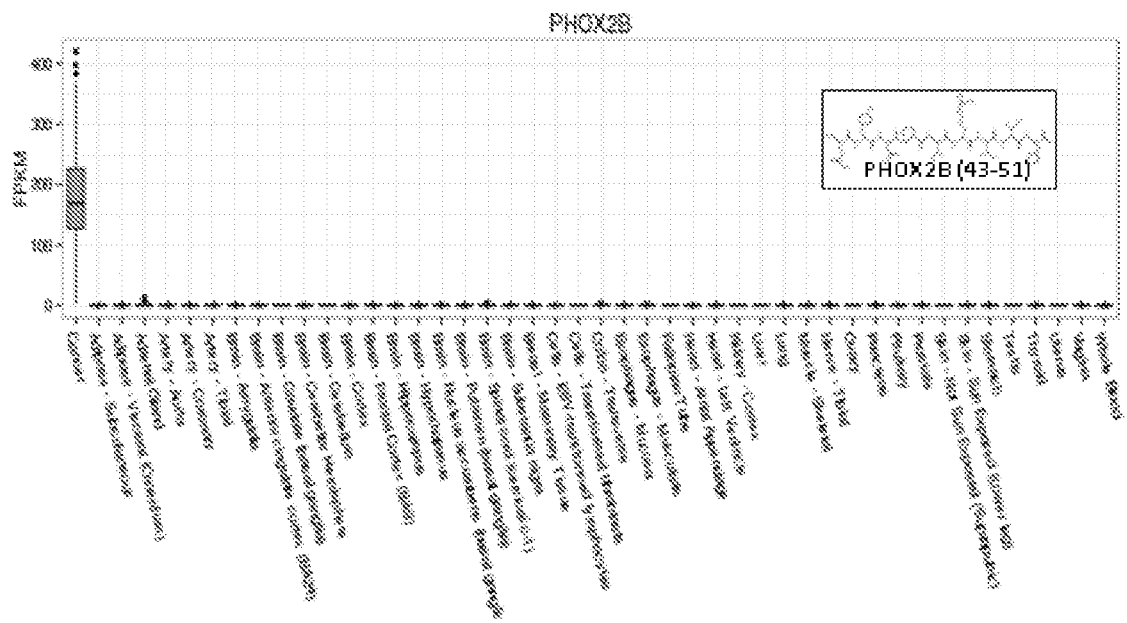
FIG. 3
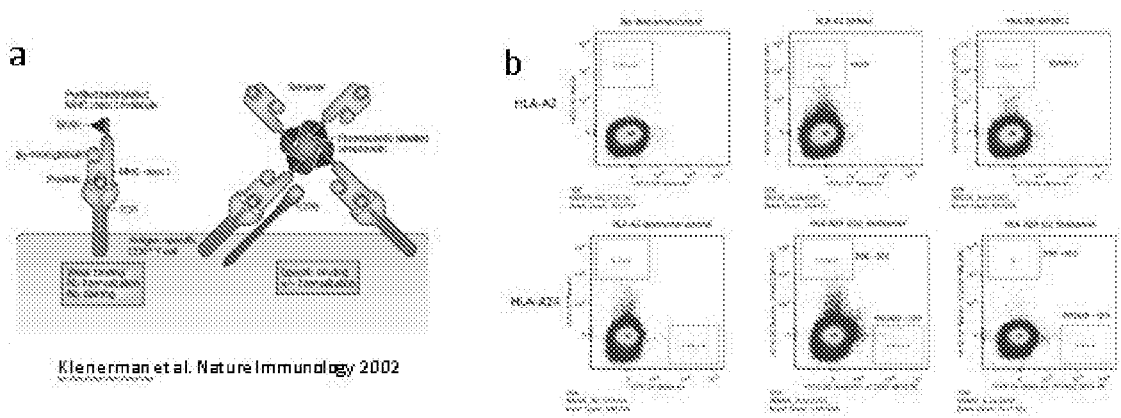
FIGS. 4A-B

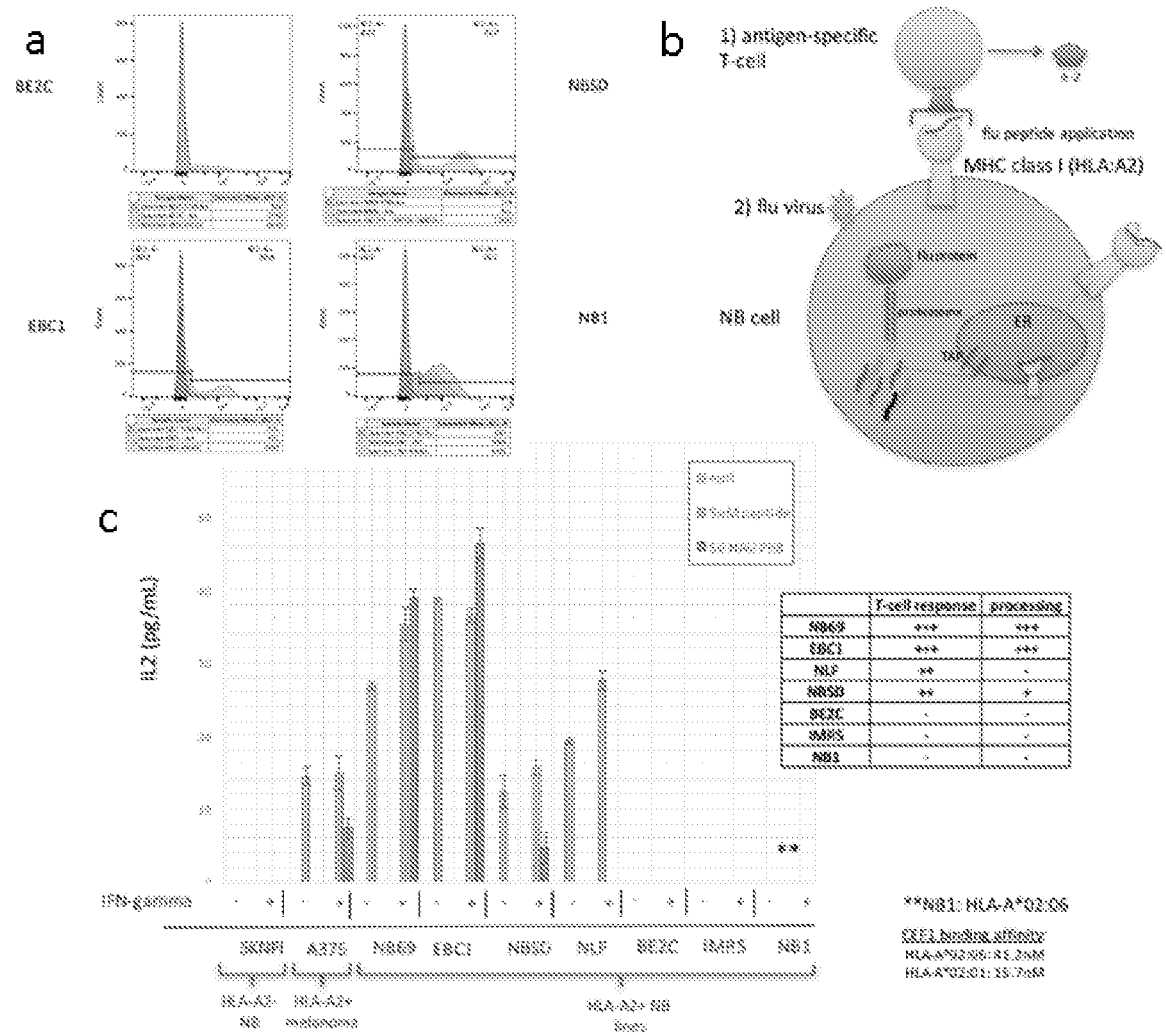
FIGS. 5A-C

METHODS AND COMPOSITIONS FOR USE OF TUMOR SELF-ANTIGENS IN ADOPTIVE IMMUNOTHERAPY

PRIORITY INFORMATION

This application is a national phase application under 35 U.S.C. § 371 of International Application No. PCT/US2019/021827, filed Mar. 12, 2019, which claims benefit of priority to U.S. Provisional Application Ser. No. 62/641,541, filed Mar. 12, 2018, the entire contents of each of which are hereby incorporated by reference.

Pursuant to 37 C.F.R. 1.821(c), a sequence listing is submitted herewith as an ASCII compliant text file named "CHOPP0015US_ST25.txt", created on Sep. 8, 2020 and having a size of ~40 kilobytes. The content of the aforementioned file is hereby incorporated by reference in its entirety.

BACKGROUND

1. Technical Field

The present disclosure relates generally to the fields of medicine, cancer, oncology, immunology, immunotherapy, cell biology, and molecular biology. In certain aspects, the field of the disclosure concerns adoptive immunotherapy. More particularly, it concerns tumor antigens, vaccines, chimeric antigen receptor (CAR) engineered T cells, T cells with engineered T-cell receptors (TCRs), engineered antibodies, and therapeutic methods of using such modalities.

2. Background

The immune system is thought to play a dual role in carcinogenesis (Ichim, 2005). First, when a proper immune response is mounted, the immune system is capable of eliminating neoplastic cells arising from early tumor-initiating events (immunoediting). In contrast, the immune system can initiate signaling of wound healing pathways that can help foster an environment conducive to tumorigenesis. The human leukocyte antigen (HLA) proteins present a snapshot of all nucleated cell's proteomes on the cell surface for surveillance by T cells. While an individual harbors six distinct HLA Class I alleles (A, B and C), a total of 13,145 unique Class I alleles have been characterized to date at these highly polymorphic loci (Robinson et al., 2018). Presentation of processed pathogen-derived peptide by at least one of these HLA alleles is a major bottleneck in the initiation of an adaptive immune response. Each HLA allele possesses the ability to present a distinct set of peptides to the immune system, based on the biophysical properties within the peptide binding groove which restrict specificity to a limited set of available peptides. Peptide binding is largely dictated by two HLA-facing anchor residues, which are restricted to a few amino acids at these positions (Fritsch et al., 2014). Recently, algorithms such as NetMHC and SYFPEITHI have allowed the prediction of binding affinity of peptide sequences to specific HLA alleles, resulting in the correct prediction of >75% of binders, with positive predictive values in the range of 90-95% (Andreatta et al., 2016; He et al., 2010; Nielsen et al., 2007).

Presented neoantigens can be divided into two distinct classes: group 1 resulting from mutations in the TCR-facing residues and correspondingly less likely to change the binding affinity of the peptide/HLA complex, and group 2 resulting from the anchor residues of the peptide, and thus presenting a longer sequence of novel polypeptides to the immune system, as compared to single-residue alterations in group one antigens (Fritsch et al., 2014). A properly mediated interaction between the HLA protein, presented peptide, and T cells serves to maintain the genomic integrity of the organism by eliminating cells harboring foreign genetic material both from external pathogens and those arising from somatic mutations. The tumor immunoediting theory predicts that early pathogenic events giving rise to precancerous cell growths can be eliminated by the adaptive immune system unless cancer cells evolve the ability to escape this selective pressure (Dunn et al., 2004).

While it has become increasingly appreciated that the adaptive immune system has the potential to play a significant role in the elimination of existing tumors, its role in the clearance of cancer cells during early initiating events has remained difficult to study. Though it has been well demonstrated that immunosuppression in humans is linked to an increased incidence of cancer (Grulich et al., 2007; Gallagher et al., 2010; Penn at al., 1973), it has remained difficult to quantify early immunoediting events, and to attribute the clearance of precancerous lesions in immunocompetent individuals to clearance of tumor-derived neoantigens, as opposed to other mechanisms such as the elimination of cells harboring cancer-inducing viruses.

SUMMARY

In accordance with the present disclosure, there is provided a chimeric antigen receptor (CAR) protein, wherein the CAR protein binds to an antigen set forth in Tables 1 or 2 or FIG. 6B. The CAR protein may bind to

| Sequence | |
|---|---|
| LLLPLLPPLSP, | (SEQ ID NO: 1) |
| LLLPLLPPL, | (SEQ ID NO: 23) |
| LLLPLLPPLSPS, | (SEQ ID NO: 24) |
| FLDETLRSLA, | (SEQ ID NO: 2) |
| QYNPIRTTF, | (SEQ ID NO: 3) |
| SYQKVIELF, | (SEQ ID NO: 4) |
| IYPDITYSL, | (SEQ ID NO: 5) |
| FLIENLLAA, | (SEQ ID NO: 6) |
| ALLSGVRQV, | (SEQ ID NO: 7) |
| VLFENTDSVHL, or | (SEQ ID NO: 8) |
| SAAMVESAL. | (SEQ ID NO: 9) |

Also provided is a polynucleotide molecule encoding a CAR protein as described above. The polynucleotide molecule may further comprise a promoter active in eukaryotic cell and may be further defined as an expression vector.

In another embodiment, there is provided a T cell receptor protein, wherein the T cell receptor protein binds to an antigen set forth in Tables 1 or 2 or FIG. 6B. The T cell receptor protein may bind to

LLLPLLPPLSP, (SEQ ID NO: 1)

LLLPLLPPL, (SEQ ID NO: 23)

LLLPLLPPLSPS, (SEQ ID NO: 24)

FLDETLRSLA, (SEQ ID NO: 2)

QYNPIRTTF, (SEQ ID NO: 3)

SYQKVIELF, (SEQ ID NO: 4)

IYPDITYSL, (SEQ ID NO: 5)

FLIENLLAA, (SEQ ID NO: 6)

ALLSGVRQV, (SEQ ID NO: 7)

VLFENTDSVHL, or (SEQ ID NO: 8)

SAAMVESAL. (SEQ ID NO: 9)

Also provided is a polynucleotide molecule encoding a T cell receptor protein as described above. The polynucleotide molecule may further comprise a promoter active in eukaryotic cell and may be further defined as an expression vector.

In still another embodiment, there is provided an engineered T cell comprising a polynucleotide molecule encoding a T cell receptor that binds an antigen from Tables 1 or 2 or FIG. 6B, such as

LLLPLLPPLSP, (SEQ ID NO: 1)

LLLPLLPPL, (SEQ ID NO: 23)

LLLPLLPPLSPS, (SEQ ID NO: 24)

FLDETLRSLA, (SEQ ID NO: 2)

QYNPIRTTF, (SEQ ID NO: 3)

SYQKVIELF, (SEQ ID NO: 4)

IYPDITYSL, (SEQ ID NO: 5)

FLIENLLAA, (SEQ ID NO: 6)

ALLSGVRQV, (SEQ ID NO: 7)

VLFENTDSVHL, or (SEQ ID NO: 8)

SAAMVESAL, (SEQ ID NO: 9)

The cell may be a T cell or an NK cell. The cell may further comprise a transposase.

In a further embodiment, there is provided a method of treating cancer in a human subject in need thereof comprising administering to the subject an effective amount of a cell therapy comprising one or more cells as described above. The method may further comprise administering to said human subject a second cancer therapy, such as chemotherapy, immunotherapy, radiotherapy, hormone therapy or surgery. The second cancer therapy may be administered at the same time as the cell therapy, or before or after the cell therapy. The method may also further comprise administering to said human subject a second administration of an effective amount of one or more cells as defined above.

The cancer may be a metastatic, recurrent or drug-resistant cancer. The cell therapy may be administered local to cancer site, region to a cancer site, or systemically. The cancer may be neuroblastoma, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma In still a further embodiment, there is provided a method of identifying a non-canonical tumor antigen comprising (a) obtaining tumor RNA and/or DNA from a tumor sample; (b) sequencing said RNA and/or DNA; (c) comparing tumor gene expression data to tumor-specific differential analysis of TARGET/TCGA vs. GTEx, thereby identifying highly expressed genes known to be specific to the tumor and absent in normal tissue; (d) obtaining MHC molecules from said tumor sample; (e) characterizing MHC bound ligands by elution and LC/MS/MS proteomics; (f) filtering identified MHC ligands based on differential expression in tumor; (g) filtering the remaining ligands from step (f) based on their absence in databases of normal ligandomes; and (h) identifying a non-canonical tumor antigen by matching empirically characterized ligands with RNA sequencing reads that do not map to canonical proteins.

The method may further comprise applying neural network machine learning to prioritize tumor antigens based on peptide/MHC binding affinity, quantitative abundance of tumor ligands on MHC surface as determined by LC/MS/MS, biological relevance to tumor type, recurrence across other tumors, population frequency of presenting HLA allele, and/or recurrence of antigen across multiple tumors. The method may also further comprise validating said identified antigen by (i) preparing a tumor antigen/MHC dextramer and sorting antigen-specific CD8 cells from healthy HLA-matched donors; and (j) performing single cell sequencing on the sorted antigen-specific T-cells to obtain paired α/β TCR sequences. The method may also further comprise pairing said α/β TCR sequences with mouse constant regions followed by codon optimization and expressing the codon optimized construct in mammalian cells. The method may also further comprise co-culturing the mammalian cells with tumors cells.

In an additional embodiment, there is provided a fusion protein comprising (i) a first single chain antibody that binds selectively to an antigen in Tables 1 or 2 or FIG. 6B, such as

| | |
|---|---|
| LLLPLLPPLSP, | (SEQ ID NO: 1) |
| LLLPLLPPL, | (SEQ ID NO: 23) |
| LLLPLLPPLSPS, | (SEQ ID NO: 24) |
| FLDETLRSLA, | (SEQ ID NO: 2) |
| QYNPIRTTF, | (SEQ ID NO: 3) |
| SYQKVIELF, | (SEQ ID NO: 4) |
| IYPDITYSL, | (SEQ ID NO: 5) |
| FLIENLLAA, | (SEQ ID NO: 6) |
| ALLSGVRQV, | (SEQ ID NO: 7) |
| VLFENTDSVHL, or | (SEQ ID NO: 8) |
| SAAMVESAL; | (SEQ ID NO: 9) | and (ii) a second single chain antibody that binds to a T or B cell. The second single chain antibody may be bind to CD3, to a T cell, or to a B cell. The fusion protein may further comprise a label or a therapeutic moiety.

In still an additional embodiment, there is provided a vaccine composition comprising one or more antigens as set forth in Tables 1 and 2 or FIG. 6B, such as

| | |
|---|---|
| LLLPLLPPLSP, | (SEQ ID NO: 1) |
| LLLPLLPPL, | (SEQ ID NO: 23) |
| LLLPLLPPLSPS, | (SEQ ID NO: 24) |
| FLDETLRSLA, | (SEQ ID NO: 2) |
| QYNPIRTTF, | (SEQ ID NO: 3) |
| SYQKVIELF, | (SEQ ID NO: 4) |
| IYPDITYSL, | (SEQ ID NO: 5) |
| FLIENLLAA, | (SEQ ID NO: 6) |
| ALLSGVRQV, | (SEQ ID NO: 7) |
| VLFENTDSVHL, or | (SEQ ID NO: 8) |
| SAAMVESAL. | (SEQ ID NO: 9) |

The vaccine composition may further comprise an adjuvant, may further comprise a biological response modifier, and/or may further comprise a chemokine. The one or more antigens may be delivered in an intact dendritic cell. Also provided is a method of generating an anti-cancer immune response is a subject comprising administering to said subject a vaccine composition as defined above.

Other objects, features and advantages of the present disclosure will become apparent from the following detailed description. It should be understood, however, that the detailed description and the specific examples, while indicating particular embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 3. Example of a recurring tumor-specific antigen (PHOX2B) observed in 4/4 tested tumors. FPKM values for tumor vs. normal tissue in PDX tumors, and structure of target peptide PHOX2B.

FIGS. 4A-B. (FIG. 4A) Schematic of peptide-MHC multimers. (FIG. 4B) Dextramer staining of rare population of tumor-antigen-specific CD8 T-cells identified from HLA-matched donors.

FIGS. 5A-C. (FIG. 5A) Representative surface MHC expression in NB measured by W6/32 pan-MHC class I antibody (red: no antibody; blue: baseline; orange IFN-γ stimulated cells). (FIG. 5B) Antigen presentation experiment using flue CEF1 matrix protein antigen. HLA-A2 neuroblastoma cells were treated with peptide and flu virus and assayed by ELISA for IL-2 release. (FIG. 5C) IL-2 release following co-incubation with flu antigen-specific T-cell hybridoma.

(FIG. 6A) 29 peptides detected by ligandomics in 16 neuroblastoma tumors were mapped onto the HLA population presentation scores. Empirically detected peptides were highly enriched in high-scoring regions of the protein (p=0.000011). (FIG. 6B) Analysis of MYCN HLA presentation across the span of the protein. Analysis of individual peptides (top) reveals the most highly presented peptide derived from MYCN, TVRPKNAAL (SEQ ID NO: 25), to be presented on 9 HLA alleles, representing 58.1% of the population. KATEYVHSL (SEQ ID NO: 26) peptide, detected by ligandomics is predicted to be presented 10 total HLA alleles (31.9% of the population). Analysis of 17mer regions (middle) reveals a peptide LERQRRNDLRSSFLTLR (SEQ ID NO: 27) generating peptides predicted to bind 19 HLA alleles (73.1% of the population). Analysis of 33-mer regions reveals the highest scoring peptide TVRPKNAALGPGRAQS-SELILKRCLPIHQQHNY (SEQ ID NO: 28) presented on 18 HLA alleles in 85.4% of the population, suggesting these as promising regions of the MYCN protein for broadly applicable vaccination.

DESCRIPTION OF ILLUSTRATIVE EMBODIMENTS

Figure 1:
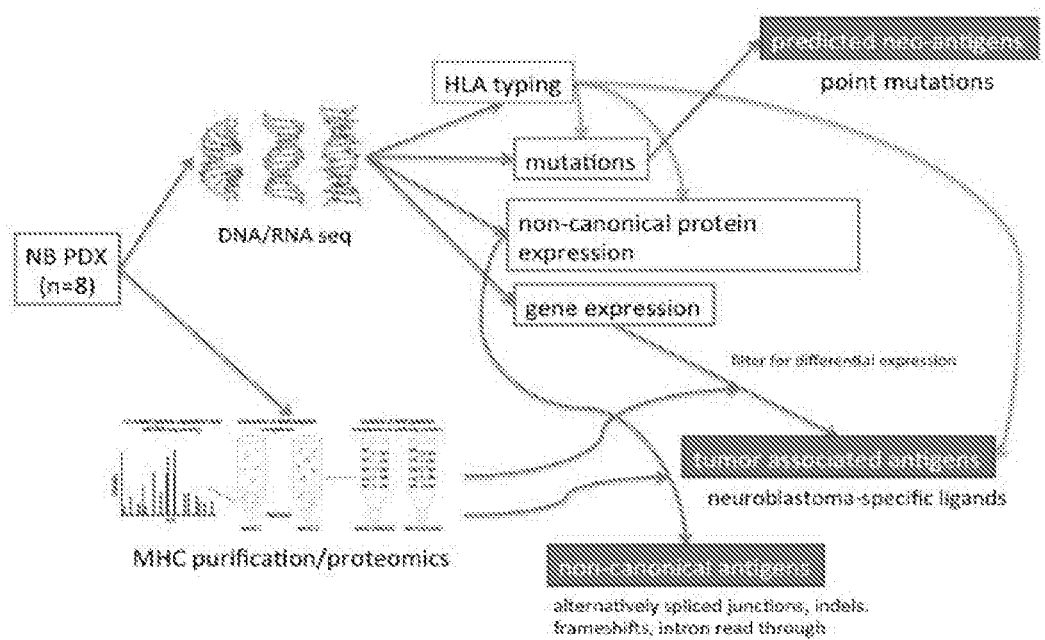
FIG. 1. Workflow of strategies used to identify tumor-specific antigens. MHC class I molecules of 8 patient-derived xenograft and 8 primary patient tumors were purified and peptides acid-eluted for characterization by LC/MS/MS to identify found MHC antigens. Using the HLA typing predicted from exome data using the PHLAT algorithm, binding affinity of peptides was predicted by machine learning algorithm NetMCH and SYFPEITHI algorithm to determine which will best bind MHC and those most likely to elicit a T-cell response. The inventors then filtered these peptides again a database of differential expression generated by comparing 1641 healthy tissues against 153 neuroblastoma tumors. The inventors searched peptides derived from the resulting genes against a database of 190 healthy tissues and 273 tumor samples characterized by MHC proteomics. Additionally, they processed non-canonical reads to generate a proteomic search library to identify antigens generated from alternative splice junctions, indels, frameshifts and intron read-throughs.
Figure 2:
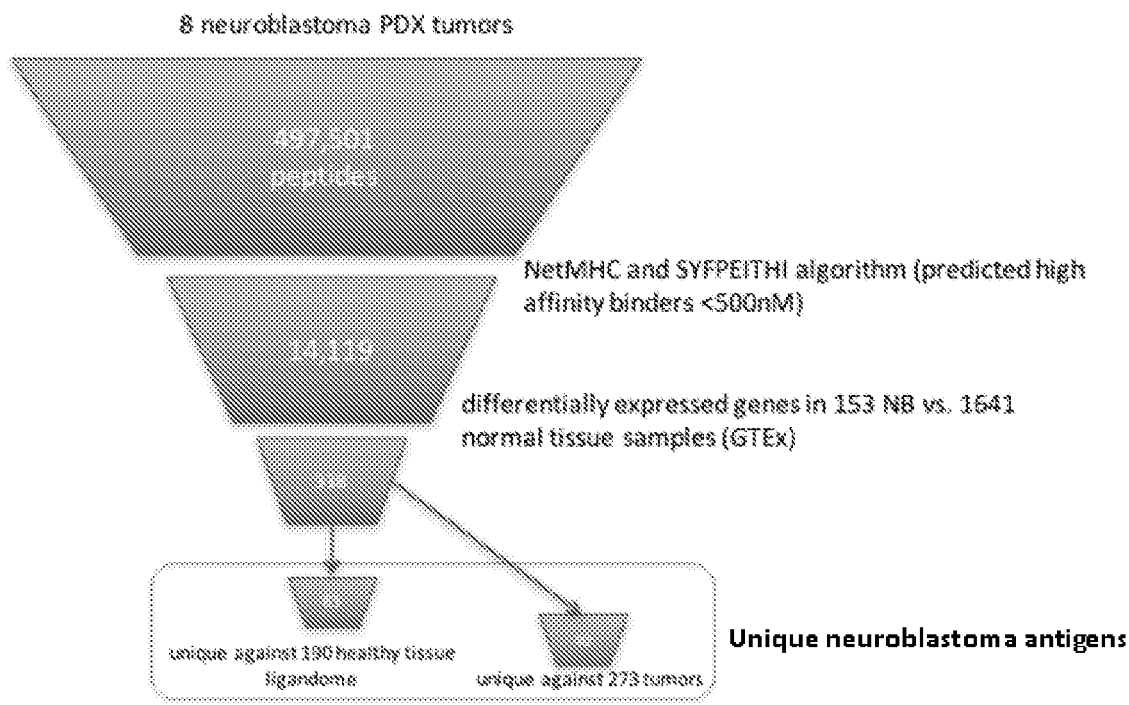
FIG. 2. Identification of MHC class I tumor specific antigens. Schematic of tumor-specific-antigen filtering and identification using combined proteomic, RNA-seq and ligandomic databases.

While immunotherapies including adoptive T-cell therapy has shown remarkable recent results, most of these cases have been in highly mutated tumors such as melanoma and lung cancer (FIG. 1; lines extending rightward from HLA typing box). Furthermore, as discussed above, development of antigen-specific T-cells remains a boutique, labor-intensive process that remains relegated to the few labs capable of performing these techniques. There remains a great need for methods of identifying tumor antigens in tumors that do not present canonical neoantigen (antigens derived from proteins with SNVs).

Neuroblastoma is a tumor characterized by low MHC expression and a low frequency of mutational burden (FIG. 1), and thus a good model for the more "difficult" targets for adoptive immunotherapy. The inventors have developed a scalable method for identifying patient-specific tumor antigens that they expect will be specific and potent targets for adoptive T-cell immunotherapy. In addition, they have created a streamlined workflow for identifying T-cell receptors (TCR) that bind these tumor antigens for use in research and clinical settings.

Taken together, the inventors have developed novel methods for scalable tumor-antigen identification and development of TCRs specific to these antigens. In addition, they have identified neuroblastoma-specific antigens which are promising targets for adoptive cancer immunotherapy as well as antigens in other "difficult" tumors. These and other aspect of the disclosure are set out in detail below.

I. Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

As used herein, the term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials define a term in a manner that contradicts the definition of that term in this application, this application controls.

As used herein, and unless otherwise indicated, the terms "disease", "disorder" or "condition" refer to a state of being or health status of a patient or subject capable of being treated with a compound, pharmaceutical composition, or method provided herein. In some embodiments, the disease is cancer (e.g., pancreatic cancer, colon cancer, gastric cancer, lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma, gastric cancer).

As used herein, and unless otherwise indicated, the terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In some embodiments, "treating" refers to the treatment of cancer.

As used herein, and unless otherwise indicated, the terms "prevent," "preventing," and "prevention" contemplate an action that occurs before a patient begins to suffer from a disorder that involves cancer that delays the onset of, and/or inhibits or reduces the severity of cancer.

As used herein, and unless otherwise indicated, the terms "manage," "managing," and "management" encompass preventing, delaying, or reducing the severity of a recurrence of a disorder such as cancer in a patient who has already suffered from such a disease, disorder or condition. The terms encompass modulating the threshold, development, and/or duration of the disorder that involves cancer or changing how a patient responds to the disorder that involves cancer.

As used herein, and unless otherwise specified, a "therapeutically effective amount" of a compound is an amount sufficient to provide any therapeutic benefit in the treatment or management of a disorder that involves electrically active cells, such as but not limited to neuronal dysfunction, a neuron mediated disorder, ocular disorder or cardiac disorder, or to delay or minimize one or more symptoms associated with a disorder that involves electrically active cells, such as but not limited to neuronal dysfunction, a neuron mediated disorder, ocular disorder or cardiac disorder. A therapeutically effective amount of a compound means an amount of the compound, alone or in combination with one or more other therapies and/or therapeutic agents that provide any therapeutic benefit in the treatment or management of a disorder that involves electrically active cells, such as but not limited to neuronal dysfunction, a neuron mediated disorder, ocular disorder or cardiac disorder.

As used herein, and unless otherwise specified, an "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, and unless otherwise specified, a "prophylactically effective amount" of a compound is an amount sufficient to prevent or delay the onset of cancer or one or more symptoms associated with cancer or prevent or delay its recurrence. A prophylactically effective amount of a compound means an amount of the compound, alone or in combination with one or more other treatment and/or prophylactic agent that provides a prophylactic benefit in the prevention of a disorder such as cancer. The term "prophylactically effective amount" can encompass an amount that prevents a disorder such as cancer, improves overall prophylaxis, or enhances the prophylactic efficacy of another prophylactic agent. The "prophylactically effective amount" can be prescribed prior to, for example, the development of a disorder such as cancer.

As used herein, "patient" or "subject in need thereof" refers to a living organism suffering from or prone to a disease or condition that can be treated by administration of a composition or pharmaceutical composition as provided herein. Non-limiting examples include humans, primates, companion animals (dogs, cats, etc.), other mammals, such as but not limited to, bovines, rats, mice, monkeys, goat, sheep, cows, deer, as well as other non-mammalian animals. In some embodiments, a patient is human.

As used herein, the term "conservative substitution" generally refers to amino acid replacements that preserve the structure and functional properties of a protein or polypeptide. Such functionally equivalent (conservative substitution) peptide amino acid sequences include, but are not limited to, additions or substitutions of amino acid residues within the amino acid sequences encoded by a nucleotide sequence that result in a silent change, thus producing a functionally equivalent gene product. Conservative amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices, and materials similar or equivalent to those described herein can be used in the practice of this disclosure. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, the presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example, mammalian, insect (e.g., *Spodoptera*) and human cells. Cells may be useful when they are naturally non-adherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Nucleic acid" refers to deoxyribonucleotides or ribonucleotides and polymers thereof, in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single- and double-stranded DNA, single- and double-stranded RNA (including siRNA), and hybrid molecules having mixtures of single- and double-stranded DNA and RNA. Nucleic acid as used herein also refers to nucleic acids that have the same basic chemical structure as a naturally occurring nucleic acid. Such analogs have modified sugars and/or modified ring substituents but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogs include, without limitation, phosphorothioates, phosphoramidites, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the disclosure or individual domains of the polypeptides of the disclosure), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more particularly over a region that is 100 to 500 or 1000 or more nucleotides in length. The present disclosure includes polypeptides that are substantially identical to any identified herein.

The word "expression" or "expressed" as used herein in reference to a gene means the transcriptional and/or translational product of that gene. The level of expression of a DNA molecule in a cell may be determined on the basis of either the amount of the corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 MOLECULAR CLONING: A LABORATORY MANUAL, 18.1-18.88. Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selective advantage to the transfected cell. Such a selective advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced into a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetization and electroporation. In some embodiments, the nucleic acid molecules are introduced into a cell using electroporation following standard procedures are well known in the art. For viral-based methods of transfection, any useful viral vector may be used in the methods described herein. Examples of viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) and Prochiantz (2007).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies may include antibodies that have been modified or mutated at one or more amino acid positions to improve or modulate a desired function of the antibody (e.g., glycosylation, expression, antigen recognition, effector functions, antigen binding, specificity, etc.).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high-performance liquid chromatography. A protein that is the predominant species present in a preparation is substantially purified.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

II. Neuroblastoma

Neuroblastoma (NB) is a type of cancer that forms in certain types of nerve tissue. It most frequently starts from one of the adrenal glands, but can also develop in the neck, chest, abdomen, or spine. Symptoms may include bone pain, a lump in the abdomen, neck, or chest, or a painless bluish lump under the skin.

Occasionally neuroblastoma may be due to a mutation inherited from a person's parents. Environmental factors have not been found to be involved. Diagnosis is based on a tissue biopsy. Occasionally it may be found in a baby by ultrasound during pregnancy. At diagnosis the cancer has usually already spread. The cancer is divided into low, intermediate, and high-risk groups based on a child's age, cancer stage, and what the cancer looks like.

Treatment and outcomes depend on the risk group a person is in. Treatments may include observation, surgery, radiation, chemotherapy, or stem cell transplantation. Low-risk disease in babies typically has a good outcome with surgery or simply observation. In high-risk disease chances of long-term survival, however, are less than 40% despite aggressive treatment.

Neuroblastoma is the most common cancer in babies and the third most common cancer in children after leukemia and brain cancer. About 1 in every 7,000 children is affected at some point in time. About 90% of cases occur in children less than 5 years old and it is rare in adults. Of cancer deaths in children about 15% are due to neuroblastoma.

A. Signs and Symptoms

The first symptoms of neuroblastoma are often vague making diagnosis difficult. Fatigue, loss of appetite, fever, and joint pain are common. Symptoms depend on primary tumor locations and metastases if present:

In the abdomen, a tumor may cause a swollen belly and constipation.

A tumor in the chest may cause breathing problems.

A tumor pressing on the spinal cord may cause weakness and thus an inability to stand, crawl, or walk.

Bone lesions in the legs and hips may cause pain and limping.

A tumor in the bones around the eyes or orbits may cause distinct bruising and swelling.

Infiltration of the bone marrow may cause pallor from anemia.

Neuroblastoma often spreads to other parts of the body before any symptoms are apparent and 50 to 60% of all neuroblastoma cases present with metastases.

The most common location for neuroblastoma to originate (i.e., the primary tumor) is in the adrenal glands. This occurs in 40% of localized tumors and in 60% of cases of widespread disease. Neuroblastoma can also develop anywhere along the sympathetic nervous system chain from the neck to the pelvis. Frequencies in different locations include: neck (1%), chest (19%), abdomen (30% non-adrenal), or pelvis (1%). In rare cases, no primary tumor can be discerned.

Rare but characteristic presentations include transverse myelopathy (tumor spinal cord compression, 5% of cases), treatment-resistant diarrhea (tumor vasoactive intestinal peptide secretion, 4% of cases), Homer's syndrome (cervical tumor, 2.4% of cases), opsoclonus myoclonus syndrome and ataxia (suspected paraneoplastic cause, 1.3% of cases), and hypertension (catecholamine secretion or renal artery compression, 1.3% of cases).

B. Cause

The cause of neuroblastoma is not well understood. The great majority of cases are sporadic and non-familial. About 1-2% of cases run in families and have been linked to specific gene mutations. Familial neuroblastoma in some cases is caused by rare germline mutations in the anaplastic lymphoma kinase (ALK) gene. Germline mutations in the PHOX2A or KIF1B gene have been implicated in familial neuroblastoma as well. Neuroblastoma is also a feature of neurofibromatosis type 1 and the Beckwith-Wiedemann syndrome.

MYCN oncogene amplification within the tumor is a common finding in neuroblastoma. The degree of amplification shows a bimodal distribution: either 3- to 10-fold, or 100- to 300-fold. The presence of this mutation is highly correlated to advanced stages of disease.

Duplicated segments of the LMO1 gene within neuroblastoma tumor cells have been shown to increase the risk of developing an aggressive form of the cancer.

Neuroblastoma has been linked to copy-number variation within the NBPF10 gene, which results in the 1q21.1 deletion syndrome or 1q21.1 duplication syndrome.

Several risk factors have been proposed and are the subject of ongoing research. Due to characteristic early onset many studies have focused on parental factors around conception and during gestation. Factors investigated have included occupation (i.e., exposure to chemicals in specific industries), smoking, alcohol consumption, use of medicinal drugs during pregnancy and birth factors; however, results have been inconclusive.

Other studies have examined possible links with atopy and exposure to infection early in life, use of hormones and fertility drugs, and maternal use of hair dye.

C. Diagnosis

The diagnosis is usually confirmed by a surgical pathologist, taking into account the clinical presentation, microscopic findings, and other laboratory tests. It may arise from any neural crest element of the sympathetic nervous system (SNS).

Esthesioneuroblastoma, also known as olfactory neuroblastoma, is believed to arise from the olfactory epithelium and its classification remains controversial. However, since it is not a sympathetic nervous system malignancy, esthesioneuroblastoma is a distinct clinical entity and is not to be confused with neuroblastoma.

D. Biochemistry

In about 90% of cases of neuroblastoma, elevated levels of catecholamines or their metabolites are found in the urine or blood. Catecholamines and their metabolites include dopamine, homovanillic acid (HVA), and/or vanillylmandelic acid (VMA).

E. Imaging

Another way to detect neuroblastoma is the mIBG scan (meta-iodobenzylguanidine), which is taken up by 90 to 95% of all neuroblastomas, often termed "mIBG-avid." The mechanism is that mIBG is taken up by sympathetic neurons and is a functioning analog of the neurotransmitter norepinephrine. When it is radio-ionated with $I^{131}$ or $I^{123}$ (radioactive iodine isotopes), it is a very good radiopharmaceutical for diagnosis and monitoring of response to treatment for this disease. With a half-life of 13 hours, $I^{123}$ is a particular isotope for imaging sensitivity and quality. $I^{131}$ has a half-life of 8 days and at higher doses is an effective therapy as targeted radiation against relapsed and refractory neuroblastoma.

F. Histology

On microscopy, the tumor cells are typically described as small, round and blue, and rosette patterns (Homer Wright rosettes) may be seen. Homer Wright rosettes are tumor cells around the neuropil, not to be confused with pseudorosettes, which are tumor cells around a blood vessel. They are also distinct from the pseudorosettes of an ependymoma which consist of tumor cells with glial fibrillary acidic protein (GFAP)-positive processes tapering off toward a blood vessel (thus a combination of the two). A variety of immunohistochemical stains are used by pathologists to distinguish neuroblastomas from histological mimics, such as rhabdomyosarcoma, Ewing's sarcoma, lymphoma and Wilms' tumor.

Neuroblastoma is one of the peripheral neuroblastic tumors (pNTs) that have similar origins and show a wide pattern of differentiation ranging from benign ganglioneuroma to stroma-rich ganglioneuroblastoma with neuroblastic cells intermixed or in nodules, to highly malignant neuroblastoma. This distinction in the pre-treatment tumor pathology is an important prognostic factor, along with age and mitosis-karyorrhexis index (MKI). This pathology classification system (the Shimada system) describes "favorable" and "unfavorable" tumors by the International Neuroblastoma Pathology Committee (INPC) which was established in 1999 and revised in 2003.

G. Staging

The "International Neuroblastoma Staging System" (INSS) established in 1986 and revised in 1988 stratifies neuroblastoma according to its anatomical presence at diagnosis:

Stage 1: Localized tumor confined to the area of origin.

Stage 2A: Unilateral tumor with incomplete gross resection; identifiable ipsilateral and contralateral lymph node negative for tumor.

Stage 2B: Unilateral tumor with complete or incomplete gross resection; with ipsilateral lymph node positive for tumor; identifiable contralateral lymph node negative for tumor.

Stage 3: Tumor infiltrating across midline with or without regional lymph node involvement; or unilateral tumor with contralateral lymph node involvement; or midline tumor with bilateral lymph node involvement.

Stage 4: Dissemination of tumor to distant lymph nodes, bone marrow, bone, liver, or other organs except as defined by Stage 4S.

Stage 4S: Age<1 year-old with localized primary tumor as defined in Stage 1 or 2, with dissemination limited to liver, skin, or bone marrow (less than 10 percent of nucleated bone marrow cells are tumors).

Although international agreement on staging (INSS) has been used, the need for an international consensus on risk assignment has also been recognized in order to compare similar cohorts in results of studies. Beginning in 2005, representatives of the major pediatric oncology cooperative groups have met to review data for 8,800 neuroblastoma patients treated in Europe, Japan, USA, Canada, and Australia between 1990 and 2002. This task force has proposed the International Neuroblastoma Risk Group (INRG) classification system. Retrospective studies revealed the high survival rate of 12-18 month-old age group, previously categorized as high-risk, and prompted the decision to reclassify 12-18 month old children without N-myc (also commonly referred to as MYCN) amplification to intermediate risk category.

The new INRG risk assignment will classify neuroblastoma at diagnosis based on a new International Neuroblastoma Risk Group Staging System (INRGSS):

Stage L1: Localized disease without image-defined risk factors.

Stage L2: Localized disease with image-defined risk factors.

Stage M: Metastatic disease.

Stage MS: Metastatic disease "special" where MS is equivalent to stage 4S.

The new risk stratification will be based on the new INRGSS staging system, age (dichotomized at 18 months), tumor grade, N-myc amplification, unbalanced 11q aberration, and ploidy into four pre-treatment risk groups: very low, low, intermediate, and high risk.

H. Screening

Urine catecholamine level can be elevated in pre-clinical neuroblastoma. Screening asymptomatic infants at three weeks, six months, and one year has been performed in Japan, Canada, Austria and Germany since the 1980s. Japan began screening six-month-olds for neuroblastoma via analysis of the levels of homovanillic acid and vanilmandelic acid in 1984. Screening was halted in 2004 after studies in Canada and Germany showed no reduction in deaths due to neuroblastoma, but rather caused an increase in diagnoses that would have disappeared without treatment, subjecting those infants to unnecessary surgery and chemotherapy.

I. Treatment

When the lesion is localized, it is generally curable. However, long-term survival for children with advanced disease older than 18 months of age is poor despite aggressive multimodal therapy (intensive chemotherapy, surgery, radiation therapy, stem cell transplant, differentiation agent isotretinoin also called 13-cis-retinoic acid, and frequently immunotherapy with anti-GD2 monoclonal antibody therapy).

Biologic and genetic characteristics have been identified, which, when added to classic clinical staging, has allowed patient assignment to risk groups for planning treatment intensity. These criteria include the age of the patient, extent of disease spread, microscopic appearance, and genetic features including DNA ploidy and N-myc oncogene amplification (N-myc regulates microRNAs), into low, intermediate, and high-risk disease. A recent biology study (COG ANBL00B1) analyzed 2687 neuroblastoma patients and the spectrum of risk assignment was determined: 37% of neuroblastoma cases are low risk, 18% are intermediate risk, and 45% are high risk. There is some evidence that the high- and low-risk types are caused by different mechanisms and are not merely two different degrees of expression of the same mechanism.

The therapies for these different risk categories are very different. Low-risk disease can frequently be observed without any treatment at all or cured with surgery alone. Intermediate-risk disease is treated with surgery and chemotherapy. High-risk neuroblastoma is treated with intensive chemotherapy, surgery, radiation therapy, bone marrow/hematopoietic stem cell transplantation, biological-based therapy with 13-cis-retinoic acid (isotretinoin or Accutane) and antibody therapy usually administered with the cytokines GM-CSF and IL-2.

With current treatments, patients with low and intermediate risk disease have an excellent prognosis with cure rates above 90% for low risk and 70-90% for intermediate risk. In contrast, therapy for high-risk neuroblastoma the past two decades resulted in cures only about 30% of the time. The addition of antibody therapy has raised survival rates for high-risk disease significantly. In March 2009 an early analysis of a Children's Oncology Group (COG) study with 226 high-risk patients showed that two years after stem cell transplant 66% of the group randomized to receive ch14.18 antibody with GM-CSF and IL-2 were alive and disease-free compared to only 46% in the group that did not receive the antibody. The randomization was stopped so all patients enrolling on the trial will receive the antibody therapy.

Chemotherapy agents used in combination have been found to be effective against neuroblastoma. Agents commonly used in induction and for stem cell transplant conditioning are platinum compounds (cisplatin, carboplatin), alkylating agents (cyclophosphamide, ifosfamide, melphalan), topoisomerase II inhibitor (etoposide), anthracycline antibiotics (doxorubicin) and *vinca* alkaloids (vincristine). Some newer regimens include topoisomerase I inhibitors (topotecan and irinotecan) in induction which have been found to be effective against recurrent disease.

J. Prognosis

Between 20% and 50% of high-risk cases do not respond adequately to induction high-dose chemotherapy and are progressive or refractory. Relapse after completion of front-line therapy is also common. Further treatment is available in phase I and phase II clinical trials that test new agents and combinations of agents against neuroblastoma, but the outcome remains very poor for relapsed high-risk disease.

Most long-term survivors alive today had low or intermediate risk disease and milder courses of treatment compared to high-risk disease. The majority of survivors have long-term effects from the treatment. Survivors of intermediate and high-risk treatment often experience hearing loss. Growth reduction, thyroid function disorders, learning difficulties, and greater risk of secondary cancers affect survivors of high-risk disease. An estimated two of three survivors of childhood cancer will ultimately develop at least one chronic and sometimes life-threatening health problem within 20 to 30 years after the cancer diagnosis.

K. Cytogenetic Profiles

Based on a series of 493 neuroblastoma samples, it has been reported that overall genomic pattern, as tested by array-based karyotyping, is a predictor of outcome in neuroblastoma:

Tumors presenting exclusively with whole chromosome copy number changes were associated with excellent survival.

Tumors presenting with any kind of segmental chromosome copy number changes were associated with a high risk of relapse.

Within tumors showing segmental alterations, additional independent predictors of decreased overall survival were N-myc amplification, 1p and 11q deletions, and 1q gain.

Earlier publications categorized neuroblastomas into three major subtypes based on cytogenetic profiles:

Subtype 1: favorable neuroblastoma with near triploidy and a predominance of numerical gains and losses, mostly representing non-metastatic NB stages 1, 2 and 4S.

Subtypes 2A and 2B: found in unfavorable widespread neuroblastoma, stages 3 and 4, with 11q loss and 17q gain without N-myc amplification (subtype 2A) or with N-myc amplification often together with 1p deletions and 17q gain (subtype 2B).

Virtual karyotyping can be performed on fresh or paraffin-embedded tumors to assess copy number at these loci. SNP array virtual karyotyping can be used for tumor samples, including neuroblastomas, because they can detect copy neutral loss of heterozygosity (acquired uniparental disomy). Copy neutral LOH can be biologically equivalent to a deletion and has been detected at key loci in neuroblastoma. ArrayCGH, FISH, or conventional cytogenetics cannot detect copy neutral LOH.

L. Epidemiology

Neuroblastoma comprises 6-10% of all childhood cancers, and 15% of cancer deaths in children. The annual mortality rate is 10 per million children in the 0- to 4-year-old age group, and 4 per million in the 4- to 9-year old age group.

The highest incidence is in the first year of life, and some cases are congenital. The age range is broad, including older children and adults, but only 10% of cases occur in people older than 5 years of age. A large European study reported less than 2% of over 4000 neuroblastoma cases were over 18 years old.

M. Treatment Philosophy

Recent focus has been to reduce therapy for low and intermediate risk neuroblastoma while maintaining survival rates at 90%. A study of 467 intermediate risk patients enrolled in A3961 from 1997 to 2005 confirmed the hypothesis that therapy could be successfully reduced for this risk group. Those with favorable characteristics (tumor grade and response) received four cycles of chemotherapy, and those with unfavorable characteristics received eight cycles, with three-year event free survival and overall survival stable at 90% for the entire cohort. Future plans are to intensify treatment for those patients with aberration of 1p36 or 11q23 chromosomes as well as for those who lack early response to treatment.

By contrast, focus the past 20 years or more has been to intensify treatment for high-risk neuroblastoma. Chemotherapy induction variations, timing of surgery, stem cell transplant regimens, various delivery schemes for radiation, and use of monoclonal antibodies and retinoids to treat minimal residual disease continue to be examined. Recent phase III clinical trials with randomization have been carried out to answer these questions to improve survival of high-risk disease:

III. Methods for Identifying Tumor Specific Autoantigens

In one aspect, the disclosure describes new methods of identifying tumor antigens that can act as targets for immune cells, especially those that have been genetically engineered specifically to express receptors capable of targeting the tumor antigens. These methods are greatly improved over current technologies and permit the identification of antigens from cancers that have a relatively lower mutation rate, as well as identifying recurrent tumor-specific antigens in tumors with higher mutational burden.

To identify antigens, tumor RNA and DNA is obtained from tumor samples and are sequenced in parallel with MHC ligands are empirically characterized by elution and LC/MS/MS proteomics (ligandomics) of tumor cells. Tumor gene expression data are compared to a tumor-specific differential analysis of TARGET/TCGA vs. GTEx to identify highly expressed genes known to be specific to the tumor and absent in normal tissue. Ligands identified by MHC ligandomics are filtered based on differential expression in tumor and remaining ligands are further filtered based on their absence in databases of normal ligandomes. Additional classes of non-canonical tumor antigens are identified using algorithms to match empirically characterized ligands with RNA-seq reads that do not map to canonical proteins. Tumor antigens are prioritized based on peptide/MHC binding affinity as determined by neural network machine learning algorithm NetMHC, quantitative abundance of tumor ligands on MHC surface as determined by LC/MS/MS, biological relevance to tumor type, recurrence across other tumors, population frequency of presenting HLA allele, and recurrence of antigen across multiple tumors.

In order to validate the selected antigens, peptide/MHC dextramers are synthesized specific to tumor ligands and used to sort antigen-specific CD8 cells from healthy HLA-matched donors. Single cell sequencing is then performed on the subset of antigen-specific T-cells to obtain paired α/β TCR sequences. Variable regions of the TCR sequences are deduced from the data and paired with mouse constant regions and codon optimized for improved expression. Expression cassettes of TCR β chains followed by α chain, linked by a P2A peptide for equimolar expression, and are cloned into a pMP71 T-cell specific expression vector. Retroviral TCR vectors are transduced into Jurkat/MA reporter cell line engineered with a NFAT-driven luciferase expression. To validate expression of TCR, transduced Jurkat/MA cells are co-cultured with tumors cells and assayed for luciferase expression.

Using this approach, the inventors have identified a number of different peptide antigens in tumor-expressed polypeptides. These proteins include IGFBPL1 (NP_001007564), GFRA2 (NM_001158510), PHOX2B (NP_003915), PBK (NP_001265874), CHRNA3

(NP_000743), HMX1 (NP_001293071.1), Tyrosine Hydroxylase (AAI43612.1), RBM34 (NP_001155005) and ATP6V0C (NP_001185498). The specific peptide sequences are shown in Table 1 below.

IV. Immune Therapies Involving Vaccines, Engineered Receptor Molecules and Cells A. BitES Bi-specific T-cell engagers (BiTEs) are a class of artificial bispecific monoclonal antibodies that are investigated for the use as anti-cancer drugs. They direct a host's immune system, more specifically the T cells' cytotoxic activity, against cancer cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule, in this case an antigen from Table 1.

Like other bispecific antibodies, and unlike ordinary monoclonal antibodies, BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

BiTEs that were in clinical trials as of July 2010 include Blinatumomab (MT103) for the treatment of non-Hodgkin's lymphoma and acute lymphoblastic leukemia, directed towards CD19, a surface molecule expressed on B cells; and MT110 for the treatment of gastrointestinal and lung cancers, directed towards the EpCAM antigen.

Utilizing the same technology, melanoma (with MCSP specific BiTEs) and acute myeloid leukemia (with CD33 specific BiTEs) can be targeted. Research in this area is currently ongoing. Another avenue for novel anti-cancer therapies is re-engineering some of the currently used conventional antibodies like trastuzumab (targeting HER2/neu), cetuximab and panitumumab (both targeting the EGF receptor), using the BiTE approach. BiTEs against CD66e and EphA2 are being developed as well.

Another example of pf BiTE technology relates to BiTE antibody derived from a T-cell receptor (TCR)-mimic monoclonal antibody (mAb) ESK1, which binds a peptide derived from the intracellular oncoprotein WT1 presented on HLA-A*02:01. Despite the very low density of the complexes at the cell surface, ESK1-BiTE selectively activated and induced proliferation of cytolytic human T cells that killed cells from multiple leukemias and solid tumors in vitro and in mice. In an autologous in vitro setting, ESK1-BiTE induced a robust secondary CD8 T-cell response specific for tumor-associated antigens other than WT1 (Dao et al., *Nature Biotechnol.* 33: 1079-1086, 2015).

B. Other Multivalent Antibody Formats

A variety of multivalent antibody constructs have now been designed. Some of these have specificity for a single epitope, but others have multiple distinct binding specificities. Bispecific antibodies include both full length and $Fab_2$ constructs, as well as molecules called diabodies. Diabodies are noncovalent dimers of single-chain Fv (scFv) fragment that consists of the heavy chain variable ($V_H$) and light chain variable ($V_L$) regions connected by a small peptide linker. Another form of diabody is single-chain $(Fv)_2$ in which two scFv fragments are covalently linked to each other. Trispecific constructs include $Fab_3$ and triabodies, with the latter being the three-scFv-version of diabodies. scFv-Fc are made of two linked single chain variable fragments fused to an intact Fc region. Minibodies are similar to scFv-Fc, but only contain a $CH_1$ domain rather than a full Fc region. Other multivalent constructs include IgNAR an d hcIgG.

C. Engineered T Cells with Peptide Antigen Specificity

In another aspect of the invention, engineered target cells expressing a TCR having specificity for a peptide antigen set forth in Table 1 are disclosed. In embodiments of the disclosure, there are: a composition encoding α and β subunits of a TCR; and instructions for use of the composition. The composition may be, for example, a recombinant virus, or a viral vector. In some embodiments, the composition comprises one or more sequences encoding TCR subunits comprising at least one of: a variable region substantially as described herein.

In some embodiments, vectors can be used to introduce polynucleotide sequences that encode all or part of a functional TCR into a packaging cell line for the preparation of a recombinant virus. In addition to the elements as described herein, the vectors can contain polynucleotide sequences encoding the various components of the recombinant virus and at least one variable region as described herein, as well as any components necessary for the production of the virus that are not provided by the packaging cell line. In other embodiments, in addition to the elements as described herein, the vectors can contain polynucleotide sequences encoding the various components of the recombinant virus and at least one variable region as described here, as well as any components necessary for the production of the virus that are not provided by the packaging cell line. Eukaryotic cell expression vectors are well known in the art and are available from a number of commercial sources.

In some embodiments, one or more multicistronic expression vectors are utilized that include two or more of the elements (e.g., the viral genes, at least one of: an m1-α sequence and an m1-β sequence, a suicide gene or genes) necessary for production of a desired recombinant virus in packaging cells. The use of multicistronic vectors reduces the total number of vectors required and thus avoids the possible difficulties associated with coordinating expression from multiple vectors. In a multicistronic vector the various elements to be expressed are operably linked to one or more promoters (and other expression control elements as necessary). In some embodiments a multicistronic vector comprising a suicide gene and/or a reporter gene, viral elements and nucleotide sequences encoding all or part of an α or β subunit of a TCR, is used, wherein the nucleotide sequences are substantially as described herein.

Each component to be expressed in a multicistronic expression vector may be separated, for example, by an IRES element or a viral 2A element, to allow for separate expression of the various proteins from the same promoter. IRES elements and 2A elements are known in the art (U.S. Pat. No. 4,937,190; de Felipe et al., 2004. *Traffic* 5: 616-626, each of which is incorporated herein by reference in its entirety). In one embodiment, oligonucleotides encoding furin cleavage site sequences (RAKR) (Fang et al., 2005. *Nat. Biotech* 23: 584-590, which is incorporated herein by reference in its entirety) linked with 2A-like sequences from foot-and-mouth diseases virus (FMDV), equine rhinitis A virus (ERAV), and thosea asigna virus (TaV) (Szymczak et al., 2004. *Nat. Biotechnol.* 22: 589-594, which is incorporated herein by reference in its entirety) are used to separate genetic elements in a multicistronic vector. The efficacy of a particular multicistronic vector for use in synthesizing the desired recombinant virus can readily be tested by detecting expression of each of the genes using standard protocols. Exemplary protocols that are well known in the art include, but are not limited to, antibody-specific immunoassays such as Western blotting.

Vectors will usually contain a promoter that is recognized by the packaging cell and that is operably linked to the polynucleotide(s) encoding the targeting molecule, viral components, and the like. A promoter is an expression control element formed by a nucleic acid sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. The activity of the inducible promoters is induced by the presence or absence of biotic or abiotic factors. Inducible promoters can be a useful tool in genetic engineering because the expression of genes to which they are operably linked can be turned on or off at certain stages of development of an organism or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in hypertext transfer protocol: world-wide-web at patentlens.net/daisy/promoters/768/271.html.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. However, heterologous promoters are contemplated, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, α-fetoprotein, and insulin). An enhancer from a eukaryotic cell virus will be used is particularly contemplated. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence and may be located at a site 5' from the promoter.

Other vectors and methods suitable for adaptation to the expression of viral polypeptides, are well known in the art and are readily adapted to the specific circumstances.

Using the teachings provided herein, one of skill in the art will recognize that the efficacy of a particular expression system can be tested by transforming packaging cells with a vector comprising a gene encoding a reporter protein and measuring the expression using a suitable technique, for example, measuring fluorescence from a green fluorescent protein conjugate. Suitable reporter genes are well known in the art.

A vector that encodes a core virus is also known as a "viral vector." There are a large number of available viral vectors that are suitable for use with the invention, including those identified for human gene therapy applications, such as those described by Pfeifer and Verma (2001, incorporated herein by reference in its entirety). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. Human Immunodeficiency virus (HIV-1)-derived vectors belong to this category. Other examples include lentivirus vectors derived from HIV-2, feline immunodeficiency virus (Hy), equine infectious anemia virus, simian immunodeficiency virus (SIV) and maedi/visna virus.

The viral vector in particular may comprise one or more genes encoding components of the recombinant virus as well as nucleic acids encoding all or part of a functional MART-1 TCR. In some embodiments, the viral vector encodes components of the recombinant virus and at least one of: an m1-α variable region, an m1-β variable region and an m2-β variable region, and optionally, a suicide or reporter gene. In other embodiments, the viral vector encodes components of the recombinant virus and at least one of: an m1-α subunit, an m1-β subunit and an m2-β subunit, and optionally, a suicide or reporter gene. The viral vector may also comprise genetic elements that facilitate expression of the corresponding α and β polynucleotide sequences in a target cell, such as promoter and enhancer sequences. In order to prevent replication in the target cell, endogenous viral genes required for replication may be removed and provided separately in the packaging cell line.

In a particular embodiment the viral vector comprises an intact retroviral 5' LTR and a self-inactivating 3' LTR.

Any method known in the art may be used to produce infectious retroviral and/or lentiviral particles whose genome comprises an RNA copy of the viral vector. To this end, the viral vector (along with other vectors encoding at least one of: an m1-α subunit and an m1-β subunit of a TCR that recognizes a peptide antigen from Table 1, and optionally, a suicide gene) may be introduced into a packaging cell line that packages viral genomic RNA based on the viral vector into viral particles.

The packaging cell line provides the viral proteins that are required in trans for the packaging of the viral genomic RNA into viral particles. The packaging cell line may be any cell line that is capable of expressing retroviral proteins. Particular packaging cell lines include 293 (ATCC CCL X), Platinum A, HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins. Such a packaging cell line is described, for example, in U.S. Pat. No. 6,218,181, which is incorporated herein by reference in its entirety. Alternatively, a packaging cell line may be transiently transfected with plasmids comprising nucleic acid that encodes one or more necessary viral proteins, including, but not limited to, gag, pol, rev, and any envelope protein that facilitates transduction of a target cell, along with the viral vectors encoding at least one of an m1-α subunit and an m1-β subunit of a TCR that recognizes a peptide antigen from Table 1.

Viral particles comprising a polynucleotide containing a gene of interest, which typically includes at least one of: an m1-α variable region nucleotide sequence, an m1-β variable region nucleotide sequence, an m2-β variable region nucleotide sequence, and optionally, a suicide or reporter gene, are collected and allowed to infect the target cell. In some embodiments, the gene of interest includes at least one of: an m1-α subunit nucleotide sequence, an m1-β subunit nucleotide sequence and an m2-β subunit nucleotide sequence. In some embodiments, the virus is pseudotyped to achieve target cell specificity. Methods for pseudotyping are well known in the art and also described herein.

In one embodiment, the recombinant virus used to deliver the gene of interest is a modified lentivirus and the viral vector is based on a lentivirus. As lentiviruses are able to infect both dividing and non-dividing cells, in this embodiment it is not necessary for target cells to be dividing (or to stimulate the target cells to divide).

In another embodiment, the recombinant virus used to deliver the gene of interest is a modified gammaretrovirus and the viral vector is based on a gammaretrovirus.

In another embodiment the vector is based on the murine stem cell virus (MSCV; (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138, each of the foregoing which is incorporated herein by reference in its entirety). The MSCV vector provides long-term stable expression in target cells, particularly hematopoietic precursor cells and their differentiated progeny.

In another embodiment, the vector is based on a modified Moloney virus, for example a Moloney Murine Leukemia Virus. The viral vector can also can be based on a hybrid virus such as that described in Choi, J. K., et al. (2001. *Stem Cells* 19, No. 3, 236-246, which is incorporated herein by reference in its entirety).

A DNA viral vector may be used, including, for example adenovirus-based vectors and adeno-associated virus (AAV)-based vectors. Likewise, retroviral-adenoviral vectors also can be used with the methods of the invention.

Other vectors also can be used for polynucleotide delivery including vectors derived from herpes simplex viruses (HSVs), including amplicon vectors, replication-defective HSV and attenuated HSV (Krisky et al. 1998. *Gene Ther.* 5: 1517-30, which is incorporated herein by reference in its entirety).

Other vectors that have recently been developed for gene therapy uses can also be used with the methods of the invention. Such vectors include those derived from baculoviruses and alpha-viruses. Jolly, D. J. (1999). Emerging viral vectors. pp 209-40 in Friedmann T, ed. (1999). The development of human gene therapy. New York: Cold Spring Harbor Lab, which is incorporated herein by reference in its entirety.

In some particular embodiments, the viral construct comprises sequences from a lentivirus genome, such as the HIV genome or the SIV genome. The viral construct may comprise sequences from the 5' and 3' LTRs of a lentivirus. More particularly, the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. In particular, the LTR sequences are HIV LTR sequences.

The viral construct may comprise an inactivated or self-inactivating 3' LTR. The 3' LTR may be made self-inactivating by any method known in the art. In a particular embodiment the U3 element of the 3' LTR contains a deletion of its enhancer sequence, such as the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In a particular embodiment the CMV enhancer/promoter sequence is used.

In some embodiments, the viral construct may comprise an inactivated or self-inactivating 3' LTR. The 3' LTR may be made self-inactivating by any method known in the art. In a particular embodiment, the U3 element of the 3' LTR contains a deletion of its enhancer sequence, such as the TATA box, Sp1 and NF-kappa B sites. As a result of the self-inactivating 3' LTR, the provirus that is integrated into the host cell genome will comprise an inactivated 5' LTR.

The viral construct generally comprises a gene of interest, which typically includes at least one of: an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence, and optionally, a suicide or reporter gene that is desirably expressed in one or more target cells. The gene of interest may located between the 5' LTR and 3' LTR sequences. Further, the gene of interest may in particular be in a functional relationship with other genetic elements, for example transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

In some embodiments, the gene of interest is in a functional relationship with internal promoter/enhancer regulatory sequences. An "internal" promoter/enhancer is one that is located between the 5' LTR and the 3' LTR sequences in the viral construct and is operably linked to the gene that is desirably expressed.

The internal promoter/enhancer may be any promoter, enhancer or promoter/enhancer combination known to increase expression of a gene with which it is in a functional relationship. A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

The internal promoter/enhancer may be selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (Karasuyama et al., 1989. *J. Exp. Med.* 169:13, which is incorporated herein by reference in its entirety), beta-actin (Gunning et al., 1989. *Proc. Natl. Acad. Sci. USA* 84:4831-4835, which is incorporated herein by reference in its entirety) and pgk (see, for example, Adra et al., 1987. *Gene* 60:65-74; Singer-Sam et al., 1984. *Gene* 32:409-417; and Dobson et al., 1982. *Nucleic Acids Res.* 10:2635-2637, each of the foregoing which is incorporated herein by reference in its entirety).

In addition, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or the target cell of interest.

D. Chimeric Antigen Receptors

"Chimeric antigen receptors" (CARs), as used herein, refer to engineered receptors that are capable of grafting a desired specificity to an antigen into an immune effector cells, such as T cells and NK cells. Typically, a CAR protein comprises an extracellular domain that introduces the desired specificity, a transmembrane domain and an intracellular domain that transmits a signal to the immune effector cells when the immune effector cells bind to the antigen. In certain embodiments, the extracellular domain comprises a leader peptide, an antigen recognition region and a spacer region. In certain embodiments, the antigen recognition region is derived from an antibody that specifically binds to the antigen. In certain embodiments, the antigen recognition region is a single-chain variable fragment (scFv) derived from the antibody. In certain embodiment, the single-chain variable fragment comprises a heavy chain variable region fused to a light chain variable region through a flexible linker.

The term "leader peptide" as referred to herein is used according to its ordinary meaning in the art and refers to a peptide having a length of about 5-30 amino acids. A leader peptide is present at the N-terminus of newly synthesized proteins that form part of the secretory pathway. Proteins of the secretory pathway include but are not limited to proteins that reside either inside certain organelles (the endoplasmic reticulum, Golgi or endosomes), are secreted from the cell, or are inserted into a cellular membrane. In some embodiments, the leader peptide forms part of the transmembrane domain of a protein.

In one aspect, the present disclosure provides a CAR protein that binds to an antigen described herein. In some embodiments, the CAR protein includes from the N-terminus to the C-terminus: a leader peptide, an anti-antigen heavy chain variable domain, a linker domain, an anti-antigen light chain variable domain, a CD8a hinge region, a CD8a transmembrane domain (or a CD28 transmembrane domain), a 4-1BB intracellular co-stimulatory signaling domain (or a CD28 intracellular co-stimulatory signaling domain, or a CD28 intracellular co-stimulatory signaling domain followed by a 4-1BB intracellular co-stimulatory signaling domain) and a CD3-ζ intracellular T cell signaling domain.

In some embodiments, the protein includes from the N-terminus to the C-terminus: a CD8a leader peptide, an antigen HuCAR scFV, a human CD8a hinge domain, a CD28 transmembrane domain, the zeta (ζ) chain of the human CD3 complex T-cell signaling domain.

In other embodiments, the protein includes from the N-terminus to the C-terminus: a CD8a leader peptide, an antigen HuCAR scFV, a human CD8a hinge domain, a 4-1BB intracellular co-stimulatory signaling domain, and the zeta (ζ) chain of the human CD3 complex T-cell signaling domain.

In an alternative embodiment, the protein includes from the N-terminus to the C-terminus: a CD8a leader peptide, an antigen HuCAR scFV, a human CD8a hinge domain, a 4-1BB intracellular co-stimulatory signaling domain, a CD28 transmembrane domain, and the zeta (ζ) chain of the human CD3 complex T-cell signaling domain.

In another embodiment, the protein includes from the N-terminus to the C-terminus: a leader peptide, an antigen heavy chain variable domain, a linker domain, an antigen light chain variable domain, a human IgG1-CH2-CH3 domain, a spacer region, a CD28 transmembrane domain, a 4-1BB intracellular co-stimulatory signaling and the zeta (ζ) chain of the human CD3 complex T-cell signaling domain.

In some embodiments, the nucleic acid encodes the antibody heavy chain variable domain and the antibody light chain variable domain from an antibody that binds the antigen.

In another aspect, an expression vector including a nucleic acid provided herein including embodiments thereof is provided. In another aspect, a T lymphocyte including the expression vector provided herein including embodiments thereof is provided. In another aspect, a mammalian cell including the expression vector provided herein including embodiments thereof is provided. In another aspect, a recombinant protein is provided. The recombinant protein includes (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, a recombinant protein is provided. The recombinant protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a recombinant protein is provided. The recombinant protein includes a first portion including an antibody heavy chain variable domain and a second portion including an antibody light chain variable domain, wherein the first portion further includes a transmembrane domain, and wherein the antibody heavy chain variable domain and the antibody light chain variable domain together form an antibody region.

In another aspect, a recombinant protein is provided. The recombinant protein includes a first portion including an antibody heavy chain variable domain and an antibody heavy chain constant domain, and a second portion including an antibody light chain variable domain, wherein the first portion further includes a transmembrane domain, and wherein the antibody heavy chain variable domain, the antibody heavy chain constant domain and the antibody light chain variable domain together form an antibody region.

In another aspect, a recombinant protein is provided. The recombinant protein includes a first portion including an antibody heavy chain variable domain and a second portion including an antibody light chain variable domain and an antibody light chain constant domain, wherein the second portion further includes a transmembrane domain, and wherein the antibody heavy chain variable domain, the antibody light chain variable domain and the antibody light chain constant domain together form an antibody region.

In another aspect, a recombinant protein is provided. The recombinant protein includes a first portion including an antibody heavy chain variable domain and a second portion including an antibody light chain variable domain, wherein the second portion further includes a transmembrane domain, and wherein the antibody heavy chain variable domain and the antibody light chain variable domain together form an antibody region.

In another aspect, a mammalian cell including the recombinant protein provided herein including embodiments thereof is provided, wherein the transmembrane domain is within the cell membrane of the mammalian cell.

In some embodiments, the transmembrane domain is a CD8α transmembrane domain. The term "CD8α transmembrane domain" as provided herein includes any of the recombinant or naturally-occurring forms of the transmembrane domain of CD8α. In some aspects, the variants or homologs have at least 90%, 95%, 96%, 97%, 98%, 99% or 100% amino acid sequence identity across the whole sequence or a portion of the sequence compared to a naturally occurring CD8α transmembrane domain polypeptide. In some embodiments, the CD8α transmembrane domain has the polypeptide sequence of IYIWAPLAGTCGVLLLSLVIT (SEQ ID NO: 10). In some embodiments, the CD8α transmembrane domain is the protein encoded by the nucleic acid sequence of (SEQ ID NO: 11)
ATCTACATCTGGGCTCCACTGGCAGGAACCTGTGGCGTGCTGCTGCTGT
CCCTGGTCATCACA.

In some embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity. In some aspects, the variants or homologs have at least 90%, 95%, 96%, 97%, 98%, 99% or 100% amino acid sequence identity across the whole sequence or a portion of the sequence compared to a naturally occurring CD28 transmembrane domain polypeptide. In some embodiments, the CD28 transmembrane domain has the polypeptide sequence of (SEQ ID NO: 12)
FWVLVVVGGVLACYSLLVTVAFIIFWV.

In some embodiments, the CD28 transmembrane domain is the protein encoded by the nucleic acid sequence of (SEQ ID NO: 13)
TTTTGGGTGCTGGTGGTGGTTGGTGGAGTCCTGGCTTGCTATAGCTTGC
TAGTAACAGTGGCCTTTATTATTTTCTGGGTG.

In some embodiments, the intracellular T cell signaling domain is a CD3-ζ intracellular T cell signaling domain. In some embodiments, the intracellular T cell signaling domain includes the signaling domain of the zeta (ζ) chain of the human CD3 complex. In some embodiments, the intracellular T cell signaling domain is a CD3-ζ intracellular T cell signaling domain. In some embodiments, the intracellular T cell signaling domain is the protein encoded by the nucleic acid sequence of (SEQ ID NO: 14)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGCTAA.

In some embodiments, the isolated nucleic acid provided herein includes an intracellular co-stimulatory signaling sequence encoding an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In some embodiments, the signaling of the co-stimulatory signaling domain results in the production of cytokines and proliferation of the T cell expressing the same. In some embodiments, the intracellular co-stimulatory signaling domain is a CD28 intracellular co-stimulatory signaling domain, a 4-1BB intracellular co-stimulatory signaling domain. In some embodiments, the intracellular co-stimulatory signaling domain includes a CD28 intracellular co-stimulatory signaling domain, a 4-1BB intracellular co-stimulatory signaling domain, an ICOS intracellular co-stimulatory signaling domain, an OX-40 intracellular co-stimulatory signaling domain or any combination thereof. In some embodiments, the CD28 co-stimulating domain has the polypeptide sequence of (SEQ ID NO: 15)
RSKRSRLLHSDYMNMTPRRPGPTRKHYQPYAPPRDFAAYRS.

In some embodiments, the CD28 intracellular co-stimulatory signaling domain is the protein encoded by the nucleic acid sequence of (SEQ ID NO: 16)
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC.

In some embodiments, the 4-1BB intracellular co-stimulatory signaling domain has the polypeptide sequence of (SEQ ID NO: 17)
KRGRKKLLYIFKQPFMRPVOTTQEEDGCSCRFPEEEEGGCEL.

In some embodiments, the 4-1BB intracellular co-stimulatory signaling domain is the protein encoded by the nucleic acid sequence of (SEQ ID NO: 18)
AAACGGGGCAGAAAGAAACTCCTGTATATATTCAAACAACCATTTATGA
GACCAGTACAAACTACTCAAGAGGAAGATGGCTGTAGCTGCCGATTTCC
AGAAGAAGAAGAAGGAGGATGTGAACTG.

In some embodiments, the isolated nucleic acid provided herein includes a spacer sequence encoding a spacer region. A "spacer region" as provided herein is a polypeptide connecting the antibody region with the transmembrane domain or connecting various components of the antibody region. In some embodiments, the spacer region is between the antibody region and the transmembrane domain. In some embodiments, the spacer region connects the heavy chain variable region with the transmembrane domain. In some embodiments, the spacer region connects the heavy chain constant region with the transmembrane domain. In some embodiments, the spacer region connects the light chain variable region with the transmembrane domain. In some embodiments, the spacer region connects the light chain constant region with the transmembrane domain. In some embodiments, the binding affinity of the antibody region to an antigen is increased compared to the absence of the spacer region. In some embodiments, the steric hindrance between an antibody region and an antigen is decreased in the presence of the spacer region.

In some embodiments, the spacer region includes a hinge region. In some embodiments, the hinge region is a CD8α hinge region. In some embodiments, the hinge region is a CD28 hinge region.

In some embodiments, the spacer region includes a Fc region. Examples of spacer regions contemplated for the compositions and methods provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In some embodiments, the spacer region is a fragment of an IgG (e.g., IgG4), wherein said fragment includes a deletion of the CH2 domain. The spacer region may be a peptide linker. In some embodiments, the nucleic acid does not include a spacer sequence encoding a spacer region.

In some embodiments, the spacer region connects various components of the antibody region. In some embodiments, the spacer region connects the heavy chain variable region with the light chain variable region.

In some embodiments, the isolated nucleic acid provided herein includes a linker sequence encoding a linker domain. In some embodiment, the linker domain is inserted between the VH and VL of the scFv. In some embodiments, the linker domain is between the transmembrane domain and the intracellular T cell signaling domain. In some embodiments, the linker domain is between the intracellular T cell signaling domain and the intracellular co-stimulatory signaling domain. In some embodiments, the linker domain comprises the sequence (SEQ ID NO: 19)
GGGGSGGGGSGGGGS.

In some embodiments, the isolated nucleic acid provided herein does not include a linker sequence encoding a linker domain.

In some embodiments, the nucleic acid includes (i) a heavy chain sequence encoding a heavy chain domain of the protein, the heavy chain domain includes a variable heavy chain domain and the transmembrane domain; and (ii) a light chain sequence encoding a light chain domain of the protein, the light chain domain includes a variable light chain domain, wherein the variable heavy chain domain and the variable light chain domain together form at least a portion of the antibody region.

In some embodiments, the nucleic acid includes (i) a heavy chain sequence encoding a heavy chain domain of the protein, the heavy chain domain includes a variable heavy chain domain; and (ii) a light chain sequence encoding a light chain domain of the protein, the light chain domain includes a variable light chain domain and a transmembrane domain, wherein the variable heavy chain domain and the variable light chain domain together form at least a portion of the antibody region.

A "heavy chain sequence" as provided herein refers to the nucleic acid sequence encoding for a heavy chain domain provided herein. A heavy chain domain provided herein may include heavy chain variable (VH) region and/or a heavy chain constant region (CH). A "light chain sequence" as provided herein refers to the nucleic acid sequence encoding for a light chain domain provided herein. A light chain domain provided herein may include a light chain variable (VL) region and/or a light chain constant region (CL). The term "heavy chain domain" as referred to herein is used according to its ordinary meaning in the art and refers to a polypeptide including a heavy chain variable (VH) region and a heavy chain constant region (CH). The term "light chain domain" as referred to herein is used according to its ordinary meaning in the art and refers to a polypeptide including a light chain variable (VL) region and a light chain constant region (CL). In some embodiments, the antibody heavy chain variable domain and the antibody light chain variable domain are humanized.

In some embodiments, the protein or antibody region provided herein including embodiments thereof competes for antigen binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of antibody that binds the antigen.

In some embodiments, the nucleic acid encodes the antibody heavy chain variable domain and the antibody light chain variable domain from an antibody that binds the antigen.

In some embodiments, the protein includes an intracellular co-stimulatory signaling domain and a CD3-ζ intracellular T cell signaling domain. In some embodiments, the protein includes from the amino terminus to the carboxyl terminus: a heavy chain variable domain, a light chain variable domain, a transmembrane domain, an intracellular co-stimulatory signaling domain and a CD3-ζ intracellular T cell signaling domain.

In some embodiments, the protein includes an intracellular co-stimulatory signaling domain and a CD3-ζ intracellular T cell signaling domain. In some embodiments, the protein includes from the amino terminus to the carboxyl terminus: a light chain variable domain, a heavy chain variable domain, a transmembrane domain, an intracellular co-stimulatory signaling domain and a CD3-ζ intracellular T cell signaling domain.

In some embodiments, the recombinant protein includes a first portion including an antibody heavy chain variable domain and a second portion including an antibody light chain variable domain. In some embodiments, the first portion includes an intracellular co-stimulatory signaling domain and a CD3-ζ intracellular T cell signaling domain. In some embodiments, the first portion includes from the amino terminus to the carboxyl terminus: a heavy chain variable domain, a transmembrane domain, an intracellular co-stimulatory signaling domain and a CD3-ζ intracellular T cell signaling domain.

In some embodiments, the recombinant protein includes a first portion including an antibody heavy chain variable domain and a heavy chain constant domain, and a second portion including an antibody light chain variable domain. In some embodiments, the first portion includes an intracellular co-stimulatory signaling domain and a CD3-ζ intracellular T cell signaling domain. In some embodiments, the first portion includes from the amino terminus to the carboxyl terminus: the heavy chain variable domain, a heavy chain constant domain, a transmembrane domain, an intracellular co-stimulatory signaling domain and a CD3-ζ (intracellular T cell signaling domain.

In some embodiments, the protein includes a CD3-ζ intracellular T cell signaling domain and intracellular co-stimulatory signaling domain. In some embodiments, the protein includes from the amino terminus to the carboxyl terminus: a heavy chain variable domain, a light chain variable domain, a transmembrane domain, a CD3-ζ intracellular T cell signaling domain and an intracellular co-stimulatory signaling domain.

In some embodiments, the recombinant protein includes a first portion including an antibody heavy chain variable domain and a second portion including an antibody light chain variable domain. In some embodiments, the first portion includes a CD3-ζ intracellular T cell signaling domain and intracellular co-stimulatory signaling domain. In some embodiments, the first portion includes from the amino terminus to the carboxyl terminus: a heavy chain variable domain, a transmembrane domain, a CD3-ζ intracellular T cell signaling domain and an intracellular co-stimulatory signaling domain.

In some embodiments, the recombinant protein includes a first portion including an antibody heavy chain variable domain and a heavy chain constant domain, and a second portion including an antibody light chain variable domain. In some embodiments, the first portion includes a CD3-ζ intracellular T cell signaling domain and intracellular co-stimulatory signaling domain. In some embodiments, the first portion includes from the amino terminus to the carboxyl terminus: a heavy chain variable domain, a heavy chain constant domain, a transmembrane domain, a CD3-ζ intracellular T cell signaling domain and an intracellular co-stimulatory signaling domain.

In some embodiments, the isolated nucleic acid encodes a protein from the N-terminus to the C-terminus: a leader peptide, an anti-antigen heavy chain variable domain, a linker domain, an anti-antigen light chain variable domain, a human IgG1-CH2-CH3 domain, a spacer region, a CD28 domain, a 4-1BB intracellular co-stimulatory signaling domain and a CD3-ζ intracellular T cell signaling domain.

In some embodiments, the isolated nucleic acid encodes a protein from the N-terminus to the C-terminus: a leader peptide, an anti-antigen heavy chain variable domain, a linker domain, an anti-antigen light chain variable domain, a spacer region, a CD28 domain, a 4-1BB intracellular co-stimulatory signaling domain and a CD3-ζ intracellular T cell signaling domain.

In some embodiments, the isolated nucleic acid encodes a protein from the N-terminus to the C-terminus: a leader peptide, an anti-antigen heavy chain variable domain, a linker domain, an anti-antigen light chain variable domain, a spacer region, a CD28 transmembrane and co-stimulatory domain, and a CD3-ζ intracellular T cell signaling domain.

In some embodiments, the isolated nucleic acid encodes a protein from the N-terminus to the C-terminus: a leader peptide, an anti-antigen heavy chain variable domain, a linker domain, an anti-antigen light chain variable domain, a spacer region, a CD8α transmembrane domain (or a CD28 transmembrane domain), a 4-1BB intracellular co-stimulatory signaling domain and a CD3-ζ intracellular T cell signaling domain.

In some embodiments, the protein includes from the N-terminus to the C-terminus: a leader peptide encoded by the nucleic acid of

```
                                      (SEQ ID NO: 20)
ATGGCCTTACCAGTGACCGCCTTGCTCCTGCCGCTGGCCTTGCTGCTCC
ACGCCGCCAGGCCG,
``` an anti-antigen heavy chain variable domain coding region, a linker domain encoded by the nucleic acid of

```
                                      (SEQ ID NO: 21)
   GGTGGAGGCGGTTCAGGTGGCGGCGGTTCGGGCGGTGGCGGCTCT,
``` an anti-antigen light chain variable domain coding region, a hinge region encoded by the nucleic acid of

```
                                      (SEQ ID NO: 22)
ACCACGACGCCAGCGCCGCGACCACCAACACCGGCGCCCACCATCGCGT

CGCAGCCCCTGTCCCTGCGCCCAGAGGCGTGCCGGCCAGCGGCGGGGGG

CGCAGTGCACACGAGGGGGCTGGACTTCGCCTGTGAT,
``` a CD28 domain encoded by the nucleic acid of SEQ ID NO: 16; a 4-1BB intracellular co-stimulatory signaling domain encoded by the nucleic acid of SEQ ID NO: 18 and a CD3-ζ intracellular T cell signaling domain encoded by the nucleic acid of SEQ ID NO: 14.

In certain embodiments, the antigen CAR protein provided herein demonstrates a high affinity to antigen. In certain embodiments, the CAR protein provided herein has a binding affinity to antigen ($EC_{50}$ as measured by ELISA) of less than 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM or 0.05 nM. For the purposes of this application, ELISA $EC_{50}$ values may be determined as follows. antigen-4 extracellular domain protein (with 6 HIS tag at the C-terminus) was produced recombinantly in HEK293 cells and coated onto a high binding 96-well clear plate (Corning-Costar, Fisher Scientific) at 1 μg/ml concentration (100 μl/well) at 4° C. for 14 to 16 hours. The coated plates were washed with PBS, pH 7.4, briefly and blocked with 200 μl/well of 5% non-fat milk in PBS for 2 hours at 37° C. Serial dilutions of the testing monoclonal antibodies (IgGs or scFvs fragments), starting from 10 μg/ml and 3-fold titration down for 12 steps, were added to the 96-well plate for binding by incubating 45 minutes at 37° C. with a cover on the assay plate. Then the plates were washed with PBS containing Tween 20 (0.05% concentration) for 3 times and PBS one time. Secondary antibody of anti-human or anti-rabbit, or other species IgG specific antibodies with HRP conjugate (Jackson ImmunoResearch) was added for incubation at room temperature for 1 hour per manufacturer's suggested dilution. Detection was conducted by adding HRP substrate, TMB (ThermoFisher) for 10 minutes, and stopped by adding 50 μl/well of 2N $H_2SO_4$. The plates were read for absorbance at 450 nm using a plate reader (SpectraMax M4, Molecular Devices). Data were collected and graphed using a 4-parameter fitting curve with GrapPad Prism 7 software for $EC_{50}$ calculation.

In another aspect, a T lymphocyte including the recombinant protein provided herein including embodiments thereof is provided, wherein the transmembrane domain is within the cell membrane of the T lymphocyte.

E. Vaccines

Cancer vaccines are a form of active immunotherapy where an antigenic peptide, polypeptide or protein, such as the antigens disclosed in Table 1, or an autologous or allogenic tumor cell composition or "vaccine" is administered to a subject. Vaccines may be administered systemically, such as intravenously or intradermally. Vaccines may also be administered multiple times to enhance the immune response against the administered antigens.

1. Adjuvants

As also well known in the art, the immunogenicity of a particular immunogen composition can be enhanced by the use of non-specific stimulators of the immune response, known as adjuvants. Adjuvants have been used experimentally to promote a generalized increase in immunity against poorly immunogenic antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are adsorbed to alum. Emulsification of antigens also prolongs the duration of antigen presentation and initiates an innate immune response. Suitable molecule adjuvants include all acceptable immunostimulatory compounds, such as cytokines, toxins or synthetic compositions.

In some aspects, the compositions described herein may further comprise another adjuvant. Although Alum is an approved adjuvant for humans, adjuvants in experimental animals include complete Freund's adjuvant (a non-specific stimulator of the immune response containing killed *Mycobacterium tuberculosis*), incomplete Freund's adjuvants and aluminum hydroxide adjuvant. Other adjuvants that may also be used in animals and sometimes humans include Interleukin (IL)-1, IL-2, IL-4, IL-7, IL-12, interferon, *Bacillus* Calmette-Guérin (BCG), aluminum hydroxide, muramyl dipeptide (MDP) compounds, such as thur-MDP and nor-MDP (N-acetylmuramyl-L-alanyl-D-isoglutamine MDP), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used.

In one aspect, and approved for humans, an adjuvant effect is achieved by use of an agent, such as alum, used in about 0.05 to about 0.1% solution in phosphate buffered saline. Alternatively, in experimental animals the antigen is made as an admixture with synthetic polymers of sugars (Carbopol®) used as an about 0.25% solution. Adjuvant effects may also be achieved by aggregation of the antigen in the vaccine by heat treatment with temperatures ranging between about 70° to about 101° C. for a 30 second to 2-minute period, respectively. Aggregation by reactivating with pepsin treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is MDP, a bacterial peptidoglycan. The effects of MDP, as with most adjuvants, are not fully understood, although it is now beginning to be understood that they activate cells of the innate immune system, e.g. dendritic cells, macrophages, neutrophils, NKT cells, NK cells, etc. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the compositions of the present disclosure. The use of hemocyanin from keyhole limpet (KLH) is used in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly contemplated, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative muramyl tripeptide phosphatidylethanolamide (MTPPE) are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. This is effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present disclosure.

BCG and BCG-cell wall skeleton (CWS) may also be used as adjuvants, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticuloendothelial system (RES), activates natural killer (NK) cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, NJ).

Amphipathic and surface-active agents, e.g., saponin and derivatives such as QS21 (Cambridge Biotech), form yet another group of adjuvants for use with the immunogens of the present disclosure. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present disclosure.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cCWS or CWS and trehalose dimycolate, as described in U.S. Pat. Nos. 4,436,727, 4,436,728 and 4,505,900. Combinations of just CWS and trehalose dimycolate, without detoxified endotoxins, are also envisioned to be useful, as described in U.S. Pat. No. 4,520,019.

Those of skill in the art will know the different kinds of adjuvants that can be conjugated to vaccines in accordance with this disclosure and which are approved for human vs experimental use. These include alkyl lysophosphilipids (ALP); BCG; and biotin (including biotinylated derivatives) among others. Certain adjuvants particularly contemplated for use are the teichoic acids from Gram bacterial cells. These include the lipoteichoic acids (LTA), ribitol teichoic acids (RTA) and glycerol teichoic acid (GTA). Active forms of their synthetic counterparts may also be employed in connection with the compositions of this disclosure (Takada et al., 1995).

Various adjuvants, even those that are not commonly used in humans, may still be employed in animals. Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

2. Biological Response Modifiers (BRM)

In addition to adjuvants, it may be desirable to co-administer BRM, which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m$^2$) (Johnson/Mead, NJ), cytokines such as interferon, IL-2, or IL-12 or genes encoding proteins involved in immune helper functions, such as B-7. Additional biological response modifiers include those described in Gupta and Kanodia, 2002 and Bisht, et al., 2010, both of which are incorporated herein by reference.

3. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines are also known to have chemoattractant effects and could also be classified under the term chemokines.

4. Immunogenic Carrier Proteins

In some embodiments, the vaccine antigens described herein may be chemically coupled to a carrier or recombinantly expressed with a immunogenic carrier peptide or polypeptide (e.g., an antigen-carrier fusion peptide or polypeptide) to enhance an immune reaction. Exemplary immunogenic carrier amino acid sequences include hepatitis B surface antigen (HBSA), tetanus toxoid (T), keyhole limpet hemocyanin (KLH) and BSA. In humans, TT would be advantageous since it is already an approved protein vaccine. For experimental animals, other albumins such as OVA, mouse serum albumin or rabbit serum albumin also can be used as immunogenic carrier proteins. Means for conjugating a polypeptide or peptide to an immunogenic carrier protein are well known in the art and include, for example, glutaraldehyde, m-maleimidobenzoyl-N-hydroxysuccinimide ester, carbodiimide and bis-biazotized benzidine.

5. Engineered Dendritic Cells

In some embodiments, the disclosure relates to dendritic cell (DC) vaccines. DC vaccines include antigen-presenting cells that are able to induce specific T cell immunity, which are harvested from the patient or from a donor. The DCs can then be exposed in vitro to a peptide antigen from Table 1, for which T cells are to be generated in the patient. Dendritic cells loaded with the antigen are then injected back into the patient. Immunization may be repeated multiple times if desired. Methods for harvesting, expanding, and administering dendritic cells are well known in the art, for example, as described in Fong et al. (2001). DC vaccines are further described elsewhere, such as in U.S. patent application Ser. No. 11/517,814, filed Sep. 8, 2006 and entitled "METHOD FOR THE GENERATION OF ANTIGEN-SPECIFIC LYMPHOCYTES"; U.S. patent application Ser. No. 11/071,785, filed Mar. 2, 2005 and entitled "ANTIGEN SPECIFIC T CELL THERAPY"; and U.S. patent application Ser. No. 11/446,353, filed Jun. 1, 2006 and entitled "METHOD OF TARGETED GENE DELIVERY USING VIRAL VECTORS," each of which is incorporated herein by reference in its entirety. Typical doses of DCs administered to the patient include at least about 10 million cells.

6. MHC Class I Antigens

For an MHC class I peptide to trigger (elicit) a cellular immune response, it also must bind to an MHC-molecule. This process is dependent on the allele of the MHC-molecule and specific polymorphisms of the amino acid sequence of the peptide. Thus, when considering vaccines of this nature, matching of MHC-antigen profiles to the MHC profile of the patient is important.

MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove. In the MHC class I dependent immune reaction, peptides not only have to be able to bind to certain MHC class I molecules expressed by tumor cells, they subsequently also have to be recognized by T cells bearing specific T cell receptors (TCR).

V. Host Cells

Certain embodiments of the present disclosure concern immune cells which express a chimeric antigen receptor (CAR). The immune cells may be T cells (e.g., regulatory T cells, CD4+ T cells, CD8+ T cells, or gamma-delta T cells), Natural Killer (NK) cells, invariant NK cells, or NKT cells. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from a subject of interest, such as a subject suspected of having a particular disease or condition, a subject suspected of having a predisposition to a particular disease or condition, a subject who is undergoing therapy for a particular disease or condition, a subject who is a healthy volunteer or healthy donor, or from blood bank. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, such as a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor may be allogeneic, provided the cells obtained are subject-compatible in that they can be introduced into the subject. Allogeneic donor cells are may or may not be human-leukocyte-antigen (HLA)-compatible. To be rendered subject-compatible, allogeneic cells can be treated to reduce immunogenicity.

A. T Cells

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., $CD4^+$ and/or $CD8^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, CD8+ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012); Wang et al. (2012).

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2 \times 10^6$ lymphocytes), e.g., from about 5 to about 21 days, such as from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. Rapid expansion can provide an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being particularly contemplated. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as a human leukocyte antigen A2 (HLA-A2) binding peptide, in the presence of a T-cell growth factor, such as 300 IU/ml IL-2 or IL-15, with IL-2 being contemplated. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., MOLECULAR CLONING: A LABORATORY MANUAL, 3$^{rd}$ ed., Cold Spring Harbor Press, Cold Spring Harbor, N.Y. 2001; and Ausubel et al., CURRENT PROTOCOLS IN MOLECULAR BIOLOGY, Greene Publishing Associates and John Wiley & Sons, NY, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. NK Cells

In some embodiments, the immune cells are natural killer (NK) cells. Natural killer (NK) cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells constitute about 10% of the lymphocytes in human peripheral blood. When lymphocytes are cultured in the presence of interleukin 2 (IL-2), strong cytotoxic reactivity develops. NK cells are effector cells known as large granular lymphocytes because of their larger size and the presence of characteristic azurophilic granules in their cytoplasm. NK cells differentiate and mature in the bone marrow, lymph nodes, spleen, tonsils, and thymus. NK cells can be detected by specific surface markers, such as CD16, CD56, and CD8 in humans. NK cells do not express T-cell antigen receptors, the pan T marker CD3, or surface immunoglobulin B cell receptors.

Stimulation of NK cells is achieved through a cross-talk of signals derived from cell surface activating and inhibitory receptors. The activation status of NK cells is regulated by a balance of intracellular signals received from an array of germ-line-encoded activating and inhibitory receptors. When NK cells encounter an abnormal cell (e.g., tumor or virus-infected cell) and activating signals predominate, the NK cells can rapidly induce apoptosis of the target cell through directed secretion of cytolytic granules containing perforin and granzymes or engagement of death domain-containing receptors. Activated NK cells can also secrete type I cytokines, such as interferon-γ, tumor necrosis factor-α and granulocyte-macrophage colony-stimulating factor (GM-CSF), which activate both innate and adaptive immune cells as well as other cytokines and. Production of these soluble factors by NK cells in early innate immune responses significantly influences the recruitment and function of other hematopoietic cells. Also, through physical contacts and production of cytokines, NK cells are central players in a regulatory crosstalk network with dendritic cells and neutrophils to promote or restrain immune responses.

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Spanholtz et al., 2011; Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of CD56+/CD3− cells or NK cells. In other methods, umbilical CB is used to derive NK cells by the isolation of CD34+ cells and differentiation into CD56+/CD3− cells by culturing in medium contain SCF, IL-7, IL-15, and IL-2.

C. Engineering of Host Cells

The immune cells (e.g., autologous or allogeneic T cells (e.g., regulatory T cells, CD4+ T cells, CD8+ T cells, or gamma-delta T cells), NK cells, invariant NK cells, or NKT cells can be genetically engineered to express antigen receptors such as engineered TCRs and/or chimeric antigen receptors (CARs). For example, the host cells (e.g, autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook and Ausubel, supra. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids/expression constructs/vectors introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

Delivery of vectors to T cells is discussed above, and that discussion is included here by reference.

VI. Methods of Use

A. Treatments

In some embodiments, the present disclosure provides methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, or hematologic cancers.

In certain embodiments of the present disclosure, immune cells are delivered to an individual in need thereof, such as an individual that has cancer. The cells then enhance the individual's immune system to attack the respective cancer cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective number of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m$^2$. In a certain embodiment, the dose used in the treatment of human subjects ranges from about $3.8 \times 10^9$ to about $3.8 \times 10^{10}$ immune cells/m$^2$. In additional embodiments, a therapeutically effective number of immune cells can vary from about $5 \times 10^6$ cells per kg body weight to about $7.5 \times 10^8$ cells per kg body weight, such as about $2 \times 10^7$ cells to about $5 \times 10^8$ cells per kg body weight, or about $5 \times 10^7$ cells to about $2 \times 10^8$ cells per kg body weight. The exact number of immune cells is readily determined by one of skill in the art based on the age, weight, sex, and physiological condition of the subject. Effective doses can be extrapolated from dose-response curves derived from in vitro or animal model test systems.

B. Pharmaceutical Compositions

Also provided herein are pharmaceutical compositions and formulations comprising immune cells (e.g., T cells, CAR-T cells, dendritic cells or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

C. Combination Therapies

In certain embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In some embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B":

A/B/A B/A/B BIB/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/AB B/A/A/A AB/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VII. Articles of Manufacture or Kits

An article of manufacture or a kit is provided comprising immune cells is also provided herein. The article of manufacture or kit can further comprise a package insert comprising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

VIII. EXAMPLES

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes can be made in the specific embodiments which are disclosed and still obtain a like or similar result without departing from the spirit and scope of the disclosure. These examples are illustrations of the methods and systems described herein and are not intended to limit the scope of the disclosure. Non-limiting examples of such include but are not limited to those presented below.

Example 1

The inventors collected CD8+ cells, purified from HLA-matched donors using negative selection. Peptide/MHC multimers (dextramers) were synthesized for each of the antigens of interest and used to stain the CD8 cells, along with antibodies against CCR7, CD14, CD19, CD4, CD8, CD45RO, CD27, CD3, Perforin, Granzyme B, T-bet, Eomes, and live/dead stain. Cells were flow sorted for dextramer-positive populations expressing CD3 and CD8 and excluding contaminating lymphocytes with non-specific dextramer staining. Antigen specific CD8+ cells were loaded on the 10× Genomics V(D)J single-cell TCR sequencing platform and amplified paired alpha/beta TCR DNA was sequenced using a MiSeq next generation sequencer. Single-cell barcodes were deconvoluted computationally and analyzed using the TCRdist pipeline (*Nature,* 2017 doi:10.1038/nature22383) in order to prioritize TCR sequences coding for homologous CDR3 hyper variable loop domains within the TCR. DNA encoding a bicistronic expression cassette coding for both alpha and beta constant and variable domains with the P2A ribosomal skipping peptide are synthesized and cloned into the pMP71 TCR expression vector. TCR constructs are transducer into the Jurkat/MA cell line, containing an NFAT-driven luciferase reporter, allowing constructs to be screened for tumor antigen specificity using a luciferase assay after co-culture with tumor cells known to express cognate tumor antigen or T2 cells defective in antigen presentation pulsed with synthetic tumor antigen peptide. TCR constructs found to induce antigen-specific responses are further screened using cytokine release assays as measured by ELISA for IL-2 and IFN-γ following co-culture with antigen-expressing cells.

TABLE 1

Listing of Antigens

| Gene | Ligand | HLA allele | Binding affinity (nm) | Tumors | Benign Tissue |
|---|---|---|---|---|---|
| IGFBPL1 | LLLPLLPPLSP (SEQ ID NO: 1) | HLA-A*02:01 | 4.15 | 2 | 0 |
|  | LLLPLLPPL (SEQ ID NO: 23) | HLA-A*02:01 | — | — | — |
|  | LLLPLLPPLSPS (SEQ ID NO: 24) | HLA-A*02:01 | — | — | — |
| GFRA2 | FLDETLRSLA (SEQ ID NO: 2) | HLA-A*02:01 | 22.8 | 3 | 0 |
| PHOX2B | QYNPIRTTF (SEQ ID NO: 3) | HLA-A*24:02 | 53.98 | 2 | 0 |
| PBK | SYQKVIELF (SEQ ID NO: 4) | HLA-A*24:02 | 3.77 | 2 | 7 |
| CHRNA3 | IYPDITYSL (SEQ ID NO: 5) | HLA-A*24:02 | 23.1 | 0 | 0 |
| HMX1 | FLIENLLAA (SEQ ID NO: 6) | HLA-A*02:01 | 2.6 | 0 | 0 |
| TH | ALLSGVRQV (SEQ ID NO: 7) | HLA-A*02:01 | 23.8 | 0 | 0 |
| RBM34 | VLFENTDSVHL (SEQ ID NO: 8) | HLA-A*02:01 | 278.3 | 19 | 1 |
| ATP6V0C | SAAMVFSAL (SEQ ID NO: 9) | HLA-C*03:03 | 6.4 | 2 | 0 |

TABLE 2

NPY Peptides Detected by Ligandomics Across PDX and Primary Tumors in HLA Class I and II

| Peptide | HLA Class | Tumor | SEQ ID NO |
|---|---|---|---|
| YPSKPDNPGED | I | Primary | 29 |
| RYYSALRHY | I | Primary | 30 |
| SPETLISDLLM | I | Primary | 31 |
| TLISDLLM | I | Primary | 32 |
| SSPETLISDLL | I | Primary | 33 |
| SALRHYINL | I | Primary | 34 |
| SSPETLISDL | I | Primary | 35 |
| SPETLISDLL | I | Primary | 36 |
| YPSKPDNPGE | I | Primary | 37 |
| YPSKPDNPGEDA | I | Primary | 38 |
| STENVPRT | I | Primary | 39 |
| TENVPRTR | I | Primary | 40 |
| RESTENVPRT | I | Primary | 41 |
| YPSKPDNPG | I | Primary | 42 |
| SKPDNPGEDAP | I | Primary | 43 |
| RESTENVPR | I | Primary | 44 |
| ESTENVPRT | I | Primary | 45 |
| SALRHYINLITR | I | PDX | 46 |
| RYYSALRHY | I | PDX | 47 |
| SALRHYINL | I | PDX | 48 |
| HYINLITR | I | PDX | 49 |
| YYSALRHYINL | I | PDX | 50 |
| YSALRHYINL | I | PDX | 51 |
| RYYSALRHYINL | I | PDX | 52 |
| YPSKPDNPGEDAPAEDMARYYS | II | Primary | 53 |
| SALRHYINLITR | II | Primary | 54 |
| YPSKPDNPGED | II | Primary | 55 |
| RESTENVPRTRLEDPA | II | Primary | 56 |
| ESTENVPRTRLEDPAMW | II | Primary | 57 |
| MRESTENVPRTRLEDPA | II | Primary | 58 |
| RESTENVPRTRLE | II | Primary | 59 |
| STENVPRTRLEDPAMW | II | Primary | 60 |
| YPSKPDNPG | II | Primary | 61 |
| SSPETLISDLLMRESTENVPR | II | Primary | 62 |
| MRESTENVPRTRLEDPAMW | II | Primary | 63 |
| ESTENVPRTRLE | II | Primary | 64 |
| LRHYINLITR | II | Primary | 65 |
| YPSKPDNPGEDAPAEDMARYY | II | Primary | 66 |
| APAEDMARYYSALRHYINL | II | Primary | 67 |
| YPSKPDNPGEDAPAEDMARY | II | Primary | 68 |
| YPSKPDNPGEDAPAEDMARYYSAL | II | Primary | 69 |
| YSALRHYINLITRQ | II | Primary | 70 |
| APAEDMARYYSALRHYIN | II | Primary | 71 |
| YPSKPDNPGEDAPAEDMARYYSA | II | Primary | 72 |
| SKPDNPGEDAPAEDMARYYSALRHY | II | Primary | 73 |
| LRHYINLITRQRYGKR | II | Primary | 74 |
| DMARYYSALRHYIN | II | Primary | 75 |
| DMARYYSALRHYINL | II | Primary | 76 |
| AEDMARYYSALRHYINL | II | Primary | 77 |
| ARYYSALRHYINL | II | Primary | 78 |
| DMARYYSALRHYINLITRQ | II | Primary | 79 |
| DAPAEDMARYYSALRHYINL | II | Primary | 80 |
| AEDMARYYSALRHYIN | II | Primary | 81 |
| SSPETLISDLLMRESTENVPRTR | II | Primary | 82 |
| YPSKPDNPGEDAPAEDMA | II | Primary | 83 |
| YPSKPDNPGEDAPAEDMAR | II | Primary | 84 |
| YYSALRHYINL | II | Primary | 85 |
| YPSKPDNPGEDAPAE | II | Primary | 86 |
| YPSKPDNPGEDAPAED | II | Primary | 87 |
| PAEDMARYYSALRHYINL | II | Primary | 88 |
| EDMARYYSALRHYINL | II | Primary | 89 |
| PGEDAPAEDMARYYSALRHYINL | II | Primary | 90 |
| SSPETLISDLLMRESTE | II | Primary | 91 |
| YPSKPDNPGEDAPAEDM | II | Primary | 92 |
| SSPETLISDLL | II | Primary | 93 |
| YSALRHYINL | II | Primary | 94 |
| SPETLISDLL | II | Primary | 95 |
| SSPETLISDLLM | II | Primary | 96 |
| ARYYSALRHYINLITRQ | II | Primary | 97 |
| LRHYINLITRQ | II | Primary | 98 |
| LRHYINLITRQRYG | II | Primary | 99 |
| SSPETLISDLLMRESTENVPRT | II | Primary | 100 |
| YYSALRHYINLITR | II | Primary | 101 |
| SALRHYINLITRQRYG | II | Primary | 102 |
| SSPETLISDLLMRESTENVPRTRLE | II | Primary | 103 |
| GEDAPAEDMARYYSALRHYINL | II | Primary | 104 |
| YPSKPDNPGEDAPA | II | Primary | 105 |
| YSALRHYINLITRQRY | II | Primary | 106 |
| ARYYSALRHY | II | Primary | 107 |
| YPSKPDNPGE | II | Primary | 108 |
| YPSKPDNPGEDAP | II | Primary | 109 |
| ESTENVPRT | II | Primary | 110 |
| YPSKPDNPGEDA | II | Primary | 111 |
| YYSALRHYIN | II | Primary | 112 |
| SKPDNPGEDAPAE | II | Primary | 113 |
| SALRHYINLITRQRY | II | Primary | 114 |
| SSPETLISDL | II | Primary | 115 |
| RYYSALRHYINLITR | II | PDX | 116 |
| SALRHYINLITR | II | PDX | 117 |
| APAEDMARYYSALRHYINL | II | PDX | 118 |
| RYYSALRHYINLITRQRYG | II | PDX | 119 |
| DMARYYSALRHYINLITR | II | PDX | 120 |
| ARYYSALRHYINLITRQRY | II | PDX | 121 |
| YSALRHYINLITR | II | PDX | 122 |
| SALRHYINLITRQRYG | II | PDX | 123 |
| RYYSALRHYINLITRQRY | II | PDX | 124 |
| SALRHYINLITRQR | II | PDX | 125 |
| APAEDMARYYSALRHYINLITRQ | II | PDX | 126 |
| SALRHYINLITRQRY | II | PDX | 127 |
| YYSALRHYINLITR | II | PDX | 128 |
| DmARYYSALRHYINLITRQRYG | II | PDX | 129 |
| DMARYYSALRHYINLITRQ | II | PDX | 130 |
| AEDMARYYSALRHYINLITRQ | II | PDX | 131 |
| YYSALRHYINLITRQRYG | II | PDX | 132 |
| ALRHYINLITRQRYG | II | PDX | 133 |
| SSPETLISDLLm | II | PDX | 134 |
| APAEDMARYYSALRHYINLIT | II | PDX | 135 |
| ARYYSALRHYINLITR | II | PDX | 136 |
| DMARYYSALRHYINLITRQR | II | PDX | 137 |
| APAEDMARYYSALRHYINLITR | II | PDX | 138 |
| RYYSALRHYINLITRQR | II | PDX | 139 |
| AEDmARYYSALRHYINLITRQRYG | II | PDX | 140 |
| DMARYYSALRHYINL | II | PDX | 141 |
| APAEDMARYYSALRHYINLI | II | PDX | 142 |
| AEDMARYYSALRHYINLITR | II | PDX | 143 |
| APAEDMARYYSALRHYINLITRQR | II | PDX | 144 |
| YYSALRHYINLIT | II | PDX | 145 |
| APAEDMARYYSALRHYINLITRQRY | II | PDX | 146 |
| ARYYSALRHYINLITRQRYG | II | PDX | 147 |
| ALRHYINLITRQRY | II | PDX | 148 |
| YSALRHYINLITRQRY | II | PDX | 149 |
| SPETLISDLLm | II | PDX | 150 |
| RYYSALRHYINL | II | PDX | 151 |
| YYSALRHYINLITRQR | II | PDX | 152 |
| SSPETLISDLL | II | PDX | 153 |
| SPETLISDLL | II | PDX | 154 |
| SSPETLISDLLMRESTENVPR | II | PDX | 155 |
| SALRHYINLITRQ | II | PDX | 156 |
| ISDLLMRESTENVPRTRLEDPAMW | II | PDX | 157 |
| YYSALRHYINLITRQRY | II | PDX | 158 |
| DMARYYSALRHYINLITRQRYGKRS | II | PDX | 159 |
| RYYSALRHYINLIT | II | PDX | 160 |
| AEDMARYYSALRHYINLITRQRY | II | PDX | 161 |
| PSKPDNPGED | II | PDX | 162 |

Example 2

A. Material and Methods

Isolation of HLA ligands by immunoaffinity purification. Eight patient-derived xenograft tumors and eight primary patient tumors were lysed in 10 mM CHAPS/PBS (AppliChem/Lonza) containing 1× protease inhibitor (Complete; Roche, Basel, Switzerland). Mouse MHC molecules were reduced using a 1 h immunoaffinity purification with H-2K-specific mAb 20-8-4S, covalently linked to CNBr-activated sepharose (GE Healthcare, Little Chalfont, UK). Remaining HLA molecules were purified overnight using the pan-HLA class I-specific mAb W6/32 or a mix of the pan-HLA class II-specific mAb Tü39 and the HLA-DR-specific mAb L243, covalently linked to CNBr-activated. MHC-peptide complexes were eluted by repeated addition of 0.2% trifluoroacetic acid (Merck). Elution fractions $E_1$-$E_4$ were pooled and free MHC ligands were isolated by ultrafiltration using centrifugal filter units (Amicon; Merck Millipore). MHC ligands were extracted and desalted from the filtrate using ZipTip $C_{18}$ pipette tips (Merck Millipore). Extracted peptides were eluted in 35 µl of acetonitrile (Merck)/0.1% trifluoroacetic acid, centrifuged to complete dryness and resuspended in 25 µl of 1% acetonitrile/0.05% trifluoroacetic acid. Samples were stored at −20° C. until analysis by LC-MS/MS.

Analysis of HLA ligands by LC-MS/MS. Peptide samples were separated by reversed-phase liquid chromatography (nanoUHPLC, UltiMate 3000 RSLCnano, Dionex) and subsequently analyzed in an on-line coupled Orbitrap Fusion Lumos (Thermo Fisher Scientific). Samples were analyzed in 3 technical replicates. Sample volumes of 5 µl (sample shares of 20%) were injected onto a 75 µm×2 cm trapping column (Acclaim PepMap RSLC, Dionex) at 4 µl/min for 5.75 min. Peptide separation was subsequently performed at 50° C. and a flow rate of 300 nl/min on a 50 µm×25 cm separation column (Acclaim PepMap RSLC, Dionex) applying a gradient ranging from 2.4-32.0% of acetonitrile over the course of 90 min. Eluting peptides were ionized by nanospray ionization and analyzed in the mass spectrometer implementing the TopSpeed method. Survey scans were generated in the Orbitrap at a resolution of 120,000. Precursor ions were isolated in the quadrupole, fragmented by either collision induced dissociation (CID) in the dual-pressure linear ion trap for MHC class I-purified peptides or higher-energy collisional dissociation (HCD) for MHC class II-purified peptides in the ion-routing multipole. Finally, fragment ions were recorded in the Orbitrap. For fragmentation mass ranges were limited to 400-650 m/z with charge states 2+ and 3+ for MHC class I or 300-1500 m/z with charge states 2+ to 5+ for MHC class II, respectively.

Database Search and Spectral Annotation. Data was processed against the human proteome as comprised in the Swiss-Prot database (world-wide-web at uniport.org, release: Sep. 27, 2013; 20,279 reviewed protein sequences contained) using the SequestHT algorithm in the Proteome Discoverer (v1.3, ThermoFisher) software. For the non-canonical peptide search data was processed against sample-specific fasta files created from RNA-Seq reads. Precursor mass tolerance was set to 5 ppm, fragment mass tolerance to 0.02 Da. Search was not restricted to an enzymatic specificity. Oxidized methionine was allowed as a dynamic modification. False discovery rate (FDR) was determined by the Percolator algorithm based on processing against a decoy database consisting of shuffled sequences. FDR was set at a target value of q≤0.05 (5% FDR). Peptide-spectrum matches (PSMs) with q≤0.05 were filtered according to additional orthogonal parameters to ensure spectral quality and validity. Peptide lengths were limited to 8-12 amino acids for MHC class I and 8-25 aa for MHC class II. HLA annotation was performed using SYFPEITHI and NetMHC-4.0 for HLA class I or NetMHCIIpan for HLA class II, respectively.

B. Results

Figure 6A:
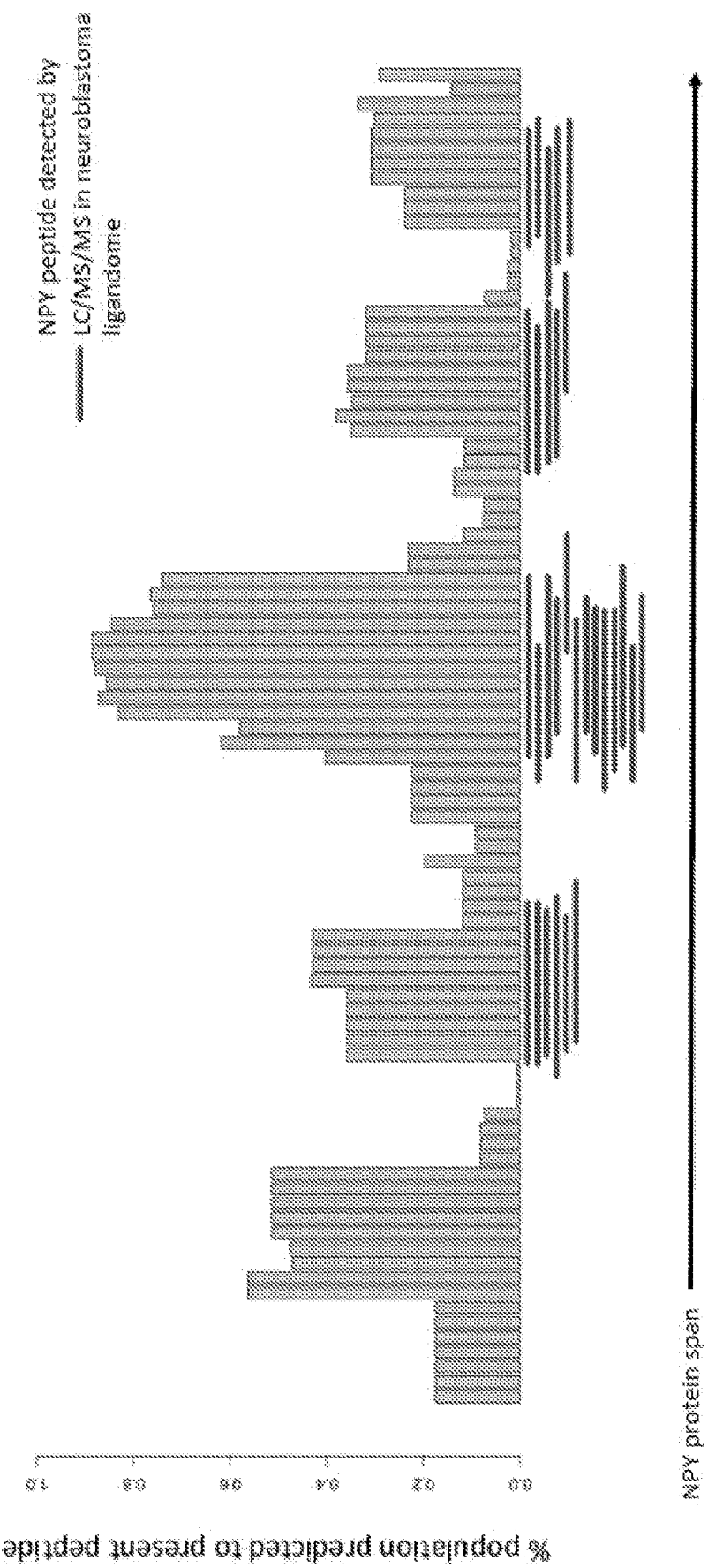
FIGS. 6A-B. HLA presentation score by protein region reveals unprotected domains and protein regions broadly applicable as cancer vaccine candidates.
Figure 6B:
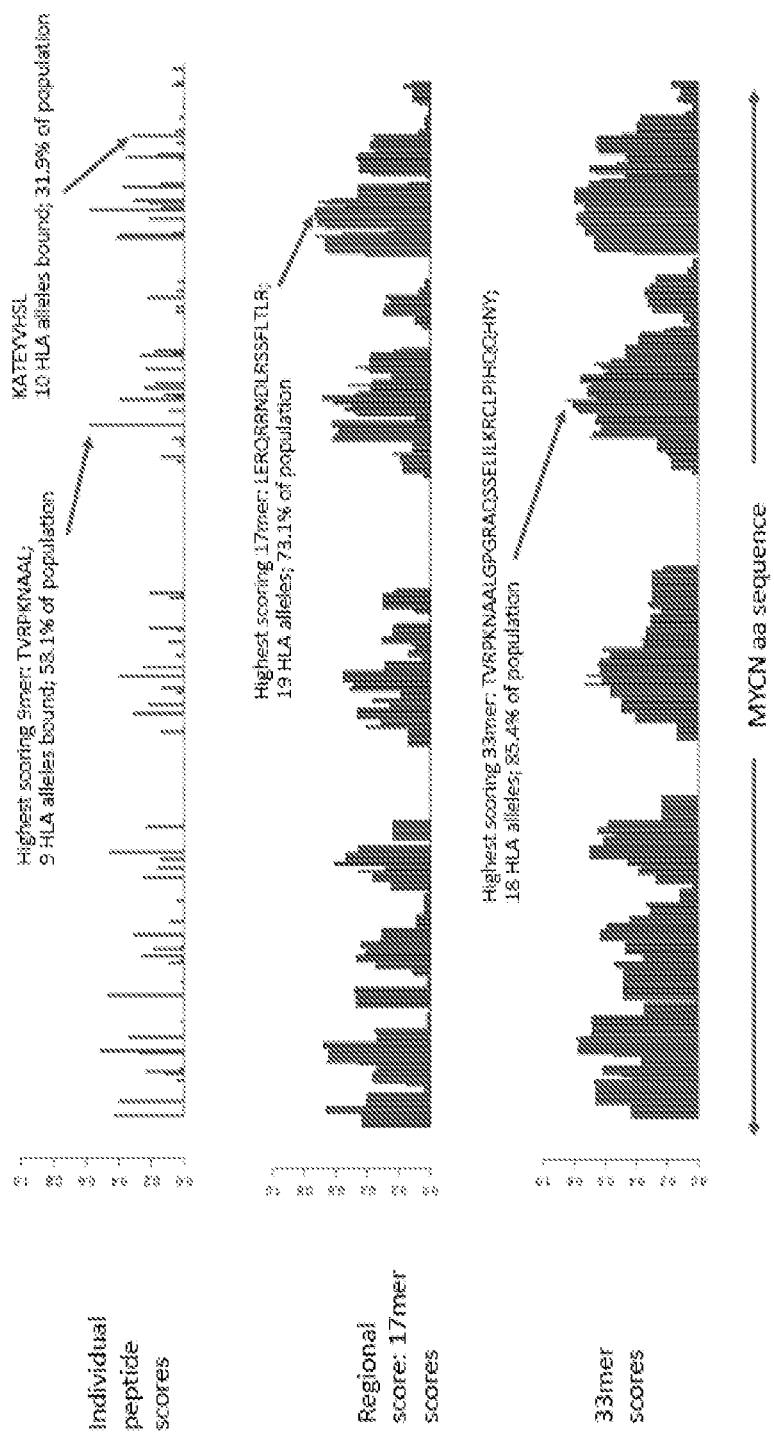
Figure 7:
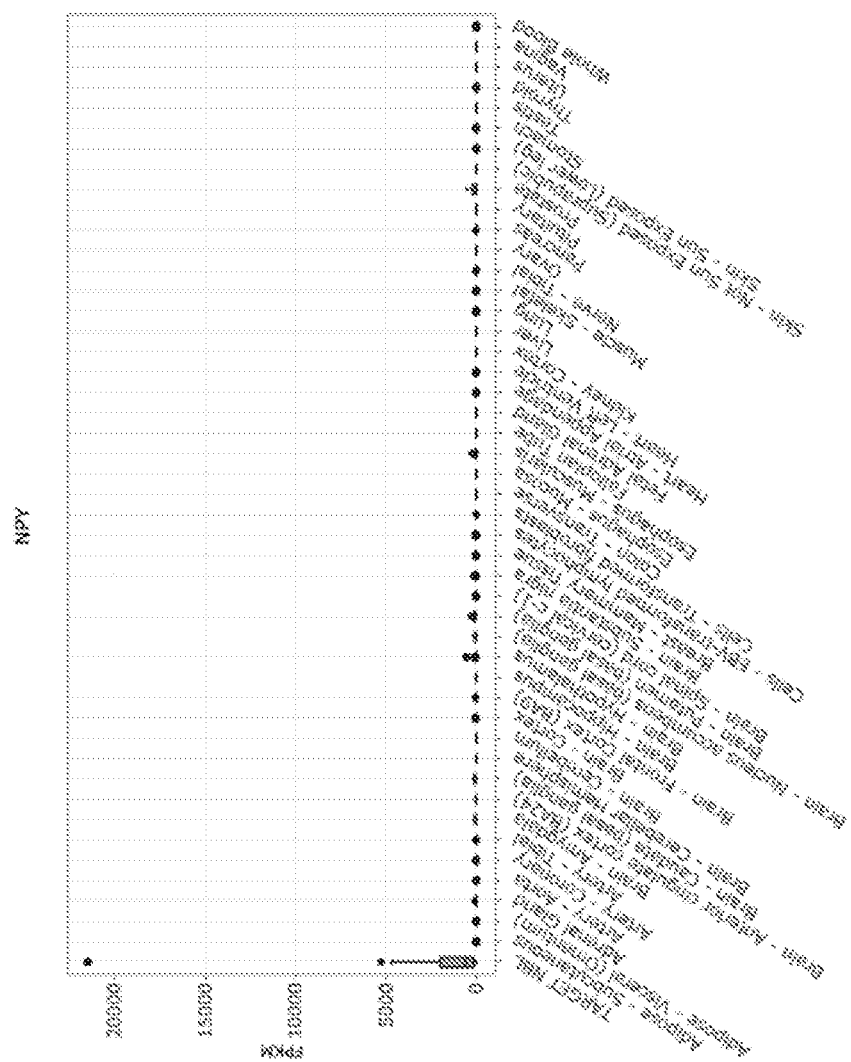
FIG. 7. NPY is highly differentially expressed in neuroblastoma and is a promising target for vaccination. RNA-sequencing data from 153 neuroblastoma tumors in TARGET (first column) compared to 1643 normal tissues from GTEx compiled by organ (subsequent columns) reveals high expression of NPY in neuroblastoma as compared to normal tissues. See Table 2.

In addition to understanding the immune evasion of proteins arising from unprotected domains of proteins, the inventors sought to apply regional HLA presentation to identifying shared tumor epitopes derived from clinically-relevant oncogenes that can be broadly therapeutically applicable across the widest population of patients. They performed mass spectrometry on 16 neuroblastoma tumors to characterize the ligandome and test the predictive ability of the HLA regional scoring across the span of a protein. They mapped the regional presentation score of the most highly represented protein in the neuroblastoma ligandome, NPY (29 MHC Class I peptides detected in 16 neuroblastomas), finding a highly significant concordance between the empirically detected peptides and those regions of the protein expected to be highly presented (FIG. 6A; p=0.000011), and find no peptides in the ligandome derived from the signal peptide region (aa 1-28) which is cleaved from the full-length pro-NPY protein. Based on the high degree of presentation across the NPY protein across 68/84 HLA alleles, its high level of differential expression (FIG. 7), and its role in promoting tumor growth (Tilan and Kitlinska, 2016), the inventors postulate that NPY is a promising candidate for vaccination strategies. Surprisingly, they find that despite the elevated population presentation score in the highly presented regions, none of the peptides presented in these regions are predicted to bind to HLA-A*02:01, highlighting the utility of a population-scale analysis of HLA presentation in identifying broadly presented epitopes that may be overlooked due to lack of presentation by HLA-A*02:01. The inventors next searched the neuroblastoma immunopeptidomics dataset they created for peptides derived from the MYCN oncogene, a major cancer driver in neuroblastoma, finding only a single peptide (KATEYVHSL; (SEQ ID NO: 26)) presented on the relatively rare HLA-C*16:01 (FIG. 6B). Applying the HLA protein scoring map, the inventors find that this peptide is predicted to bind strongly to 10/84 HLA alleles, representing 31.9% of the population (ranking 15$^{th}$ of 456 peptides in population binding score), and suggesting that this peptide can have broad application as a therapeutic target in this pediatric cancer population. This peptide overlaps with the previously reported immunogenic HLA-A*02:01 peptide VILKKATEYV (SEQ ID NO: 163) (Himoudi et al., 2008), suggesting that immunization using this region of MYCN may have wider implications beyond HLA-A*02:01 patients. Using this analysis, the inventors find that the highest scoring MYCN peptide (TVRPKNAAL; (SEQ ID NO: 25)) has predicted binding to 9 HLA alleles, representing 58.1% of the population, and they expect analysis of more neuroblastoma tumor specimens will validate this prediction. The inventors further analyzed regional scores across 17-mers and 33-mers, they find that these regions are predicted to generate peptides binding to 73.1% and 85.4% of the population, respectively (FIG. 6BF). They suggest that these tools can be used to design and prioritize more broadly applicable therapeutic targets and vaccines for cancer, particularly when paired with ligandomics data. Analyses of population-scale presentation along the span of individual proteins and of specific neoantigens is available through the Shiny-NAP web application (reslnmaris01.research.chop.edu:3838/shinyNAP/).

C. Discussion

Here the inventors describe a model for quantifying immunoediting during early tumorigenesis that provides insight into immunologic contributions to recurrent somatic mutation hotspots observed in human cancer, as well as immunologic contributions to cancer susceptibility. The model described herein employs orthogonal methods to recent studies in demonstrating evidence of immunoediting in the TCGA cohort (Rech et al., 2018; Marty et al., 2017 and Rooney et al., 2015). Using an HLA-based hypothesis, the inventors converge on the conclusion that common driver mutations evade the immune system and provide a population-scale HLA-centric basis for their overrepresentation in human cancer. In each of these studies, the immunoediting process is demonstrated to be imperfect, precipitating a need to understand this disparity in immune response. Here, the inventors provide methods that can be employed to elucidate immunoediting across HLA alleles, patients, individual variants, and other genomic or clinical features. The inventors believe that their HLA-centric population-scale model provides a baseline of comparison against which they can estimate the degree of immunoediting, with several examples of disparities across these features highlighted in this manuscript.

This is the first report that the inventors are aware of to map known driver neoantigens across common HLA alleles, and quite strikingly the most recurrent hotspot mutations in human cancer are predicted to bind no common HLA allele with high enough affinity to engage the adaptive immune system, highlighting an immunologic mechanism underlying the evolutionary advantage of common mutations in addition to their oncogenic potency. This is also the first report the inventors are aware of to quantify the contributions of individual HLA alleles to the immunoediting process in cancer, revealing a high disparity in immune protection against cancer across the HLA alleles. These data suggest that the ability of individual HLA alleles to bind cancer neoantigens with high affinity is strongly associated with its ability to contribute to cancer immunoediting. Though these data support the cancer immunoediting theory, the inventors and others show that the immunoediting process leads to incomplete elimination of neoantigens arising from early driver mutations. While the inventors demonstrate that a significant degree of immune evasion may be attributed to immunogenically silent mutations, the absence of complete immunoediting in patients not harboring immunogenically silent mutations may be attributed to factors including tumor intrinsic immune evasion, downregulation of MHC, lack of T cell response of the proper magnitude and quality, poor TCR repertoire, exclusion of T cells from tissue, or peripheral tolerance. The inventors believe that their model can be coupled with genomic surrogates of these features to interrogate these variables in future studies using tumor genomic data.

Here, the inventors show that not all HLA alleles are found to be significantly protective against the neoantigens that they present. They postulate that alleles not found to significantly participate in immunoediting may induce sublethal T cell responses or possess biophysical and/or geometric properties that confer suboptimal interactions with germline-encoded binding regions of the TCR. The findings that specific regions of cancer driver proteins are unprotected by HLA presentation combined with the disparity in binding across HLA alleles raises the question of whether HLA alleles have evolved to confer protectivity against particular viral domains that coincide with motifs found in cancer proteins, and whether the unpresented areas remain unprotected due to lack of evolutionary pressure on these motifs. These results also raise the question of whether HLA presentation of group 2 neoantigens is associated with mutational signatures arising from particular groups of DNA damage that generate variants with more favorable binding properties in the anchor residues (Alexandrov et al., 2013). The inventors have made available the tools for other investigators to test these and other hypotheses (reslnmaris01.research.chop.edu:3838/shinyNAP/).

The inventors also present a tool for mapping the presentation scores across the span of any given protein in the population. They find a highly significant concordance between the peptides empirically detected in the combined ligandome of 16 neuroblastoma tumors carrying various HLA alleles, and the regions of the NPY protein predicted to be most highly presented by HLA across the population. Based on these results paired with the high level of differential expression, and its role in promoting tumor growth, the inventors suggest that NPY is a promising candidate for vaccine development for neuroblastoma patients. Using this tool, the inventors also suggest that current vaccination strategies used against MYCN may have broader application across the population.

As access to genomic data from cancer patients continues to expand, and the peptide/MHC binding and T cell epitope prediction tools improve, this model will benefit from additional statistical power in stratifying subsets of the patient population based on molecular features occurring in smaller subpopulations. Despite the fact that this model predicted no HLA alleles binding to neoantigens derived from the KRAS G12D mutation, it was recently reported by Tran and colleagues that KRAS G12D neoantigen GADGVGKSA (SEQ ID NO: 164) is able to mediate a T cell response in the context of HLA-C*08:02. This antigen is predicted to be a weak HLA binder (15,390 nM), highlighting the fact that T cell epitopes are not always predicted using this algorithm, particularly on rare alleles for which there are limited training data, and that new methods will help identify neoantigens with non-canonical motifs (Abelin et al., 2017). Here, the inventors restricted their analysis of immunoediting by CD8 T cells through MHC class I presentation of 9-mer antigens only, and did not account for immunoediting that may be triggered by other Class I antigens of varying lengths, Class II antigens, or the activities of the innate immune system from NK cells or macrophages, as the inventors were focused on maintaining statistical power by using common HLA alleles and the most common Class I peptide length. In the future, the inventors will be expanding the analysis to additional peptide lengths and releasing additional features to the Shiny-NAP application.

The inventors find that the highest statistically significant immunoediting takes place in glioblastoma, whereas, taken together, sarcomas, pancreatic tumors, ovarian, adrenocortical tumors and lymphomas show no significant evidence of immunoediting. Given that the immunogenically silent KRAS G12D mutation is pathognomonic of pancreatic cancer, these findings may help explain the lack of efficacy of treatments such as checkpoint inhibitors in pancreatic cancer (Winograd et al., 2015) and the lack of immunoediting observed in the inventors' analysis, as these tumors are driven largely by an immunogenically silent mutation. They suggest that their methods could ultimately be used to inform the stratification of groups of patients most likely to respond to immunotherapies such as checkpoint inhibitors and to prioritize peptide vaccines based on patient HLA and antigen immunogenicity. This model can also be used to predict how an individual's HLA profile can determine the types of mutations most likely to develop or be protected against.

Using the model of immunogenicity described herein, it may be possible to infer physical properties of neoantigens that elicit high immunoediting as compared to other neoantigens that are presented but not eliminated by the immune system, study the contributions of various molecular pathways across tumor types and across individual patients that contribute to variable degrees of immunoediting, and as a basis for exploring the mechanisms by which specific HLA alleles may contribute to cancer protection and predisposition. With alleles such HLA-A*68:01 emerging as disproportionately high in their immunoediting score, the inventors will be interested to see whether contributions of HLA alleles to early immunoediting will translate to improved abilities to induce T cell responses against tumor neoantigens in patients, and whether such alleles are associated with improved outcomes in patients treated with modern immunotherapies. The inventors suggest that the immunogenicity map, HLA typing data, and immunoediting model contained herein will facilitate investigation into neoantigen immunogenicity at the level of HLA alleles, mutations, patients, histologies, and aid in prioritization of shared tumor epitopes for therapeutic development, and further the inventors' mechanistic understanding of immune evasion in tumor evolution.

TABLE S1

Driver oncogenes and tumor suppressor genes.

| Gene Symbol | Gene Symbol | Gene Symbol | Gene Symbol | Gene Symbol | Gene Symbol |
|---|---|---|---|---|---|
| ABL1 | CASP8 | FGFR2 | KDM6A | NOTCH2 | SMAD2 |
| ACVR1B | CBL | FGFR3 | KIT | NPM1 | SMAD4 |
| AKT1 | CDC73 | FLT3 | KLF4 | NRAS | SMARCA4 |
| ALK | CDH1 | FOXL2 | KRAS | PAX5 | SMARCB1 |
| APC | CDKN2A | FUBP1 | MAP2K1 | PBRM1 | SMO |
| AR | CEBPA | GATA1 | MAP3K1 | PDGFRA | SOCS1 |
| ARID1A | CIC | GATA2 | MED12 | PHF6 | SOX9 |
| ARID1B | CREBBP | GATA3 | MEN1 | PIK3CA | SPOP |
| ARID2 | CRLF2 | GNA11 | MET | PIK3R1 | SRSF2 |
| ASXL1 | CSF1R | GNAQ | MLH1 | PPP2R1A | STAG2 |
| ATM | CTNNB1 | GNAS | MLL2 | PRDM1 | STK11 |
| ATRX | CYLD | H3F3A | MLL3 | PTCH1 | TET2 |
| AXIN1 | DAXX | HIST1H3B | MPL | PTEN | TNFAIP3 |
| B2M | DNMT1 | HNF1A | MSH2 | PTPN11 | TRAF7 |
| BAP1 | DNMT3A | HRAS | MSH6 | RB1 | TP53 |
| BCL2 | EGFR | IDH1 | MYD88 | RET | TSC1 |
| BCOR | EP300 | IDH2 | NCOR1 | RNF43 | TSHR |
| BRAF | ERBB2 | JAK1 | NF1 | RUNX1 | U2AF1 |
| BRCA1 | EZH2 | JAK2 | NF2 | SETD2 | VHL |
| BACA2 | FAM123B | JAK3 | NFE2L2 | SETBP1 | WT1 |
| CARD11 | FBXW7 | KDM5C | NOTCH1 | SF3B1 | |

List of 125 cancer driver genes implicated in carcinogenesis, including oncogenes and tumor suppressor genes that regulate cell fate, cell survival, and genome maintenance (Vogelstein et al., 2013).

TABLE S3

Validation of HLA genotyping.

| | PHLAT prediction | | | | Clinical genotyping | |
|---|---|---|---|---|---|---|
| | | | SKNAS | | | |
| Locus | Allele 1 | Allele 2 | pval1 | pval2 | Allele 1 | Allele 2 |
| HLA_A | A*24:02 | A*26:01 | 0.082 | 0.013 | A*24:02 | A*26:01 |
| HLA_B | B*14:01:01 | B*40:01:02 | 0.012 | 0.019 | B*14:01:01 | B*40:01:02 |
| HLA-C | C*03:04:01 | C*08:02:01 | 0.0006 | 0.01 | C*03:04:01 | C*08:02:01 |
| | | | NEBC1 | | | |
| Locus | Allele 1 | Allele 2 | pval1 | pval2 | Allele 1 | Allele 2 |
| HLA_A | A*02:01:01 | A*02:01:18 | 0.031 | 0.031 | A*02:01:01 | A*02:01:18 |
| HLA_B | B*15:01:01 | B*57:01:01 | 0.0018 | 0.0098 | B*15:01:01 | B*57:01:01 |
| HLA-C | C:03:03:01 | C*06:02:01 | 0.036 | 0.025 | C*03:03:01 | C*06:02:01 |
| | | | NB1691 | | | |
| Locus | Allele 1 | Allele 2 | pval1 | pval2 | Allele 1 | Allele 2 |
| HLA_A | A*11:01:01 | A*30:02:01 | 0.041 | 0.04 | A*11:01:01 | A*30:02:01 |
| HLA_B | B*18:01:01 | B*50:01:01 | 0.025 | 0.004 | B*18:01:01 | B*50:01:01 |
| HLA-C | C*05:01:01 | C*07:02:01 | 0.022 | 0.15 | C*05:01:01 | C*07:02:01 |

Comparison of HLA predictions across 15 HLA alleles as inferred from PHLAT algorithm from exome sequencing data of 3 neuroblastoma cell lines compared to clinical genotyping performed using next generation sequencing of amplified HLA loci.

TABLE S5

| | | | | | | expected | observed | |
| | | | | % of | | mut freq | mut freq | |
| | | | mut | population | HLAs | with HLA | with HLA | |
| Hugo_Symbol | HGVSp_Short | variant | freq | binders | bound | binder | binder | p-val |
|---|---|---|---|---|---|---|---|---|
| PTEN | p.D92E | PTEN_D92E | 5 | 60.70% | 12 | 3.033 | 0 | 0.00942 |
| KRAS | p.G12A | KRAS_G12A | 35 | 12.20% | 4 | 4.282 | 0 | 0.01039 |
| SMAD4 | p.R361H | SMAD4_R361H | 17 | 19.60% | 2 | 3.337 | 0 | 0.02435 |
| TP53 | p.A159V | TP53_A159V | 14 | 42.90% | 8 | 6.000 | 2 | 0.02483 |
| KRAS | p.A146T | KRAS_A146T | 21 | 14.90% | 6 | 3.126 | 0 | 0.03391 |
| EGFR | p.L858R | EGFR_L858R | 23 | 50.00% | 9 | 11.501 | 7 | 0.04653 |
| IDH1 | p.R132H | IDH1_R132H | 361 | 10.20% | 8 | 36.801 | 27 | 0.04831 |
| AKT1 | p.E17K | AKT1_E17K | 42 | 37.00% | 9 | 15.578 | 10 | 0.04921 |

List of variants most underrepresented when measured with population of patients harboring HLA alleles predicted to bind neoantigens derived from variant ($p \leq 0.05$). Percent of population with binders is the probability of a TCGA subject harboring an HLA allele capable of binding a neoepitope derived from the particular variant. Observed mutation is frequency calculated from the number of patients with at least one HLA allele from the set of those capable of binding the variant.

TABLE S6

Immunoedited subjects from TCGA.

| Patient | HLAA1 | HLAA2 | HLAB1 | HLAB2 | HLAC1 | HLAC2 | Histology |
|---|---|---|---|---|---|---|---|
| TCGA-E6-A1LX | A0181 | A0201 | B2705 | B2705 | C0102 | C0102 | Uterine Corpus Endometrial Carcinoma |
| TCGA-06-5416 | A0181 | A0201 | B4047 | B4409 | C0304 | C0501 | Glioblastoma multiforme |
| TCGA-BS-A0UV | A2402 | A2402 | B4001 | B4001 | C0304 | C0304 | Uterine Corpus Endometrial Carcinoma |
| TCGA-BR-8680 | A3303 | A3403 | B4001 | B4601 | C0102 | C0304 | Stomach adenocarcinoma |
| TCGA-AI-A3EL | A1101 | A3101 | B1301 | B4601 | C0102 | C0406 | Uterine Corpus Endometrial Carcinoma |
| TCGA-AZ-6601 | A0301 | A3303 | B5201 | B5801 | C0302 | C1202 | Colon adenocarcinoma |
| TCGA-19-5956 | A0101 | A0201 | B4002 | B4402 | C0202 | C0704 | Glioblastoma multiforme |
| TCGA-EY-A1GI | A0201 | A3004 | B2705 | B5108 | C0102 | C1602 | Uterine Corpus Endometrial Carcinoma |
| TCGA-B5-A11R | A2301 | A2402 | B4201 | B5301 | C0401 | C1701 | Uterine Corpus Endometrial Carcinoma |
| TCGA-HU-A4GB | A0205 | A2402 | B2705 | B5201 | C0102 | C1202 | Stomach adenocarcinoma |
| TCGA-66-2785 | A3004 | A3403 | B3503 | B5001 | C0602 | C0602 | Lung squamous cell carcinoma |
| TCGA-EE-A2GC | A0181 | A0201 | B5101 | B5101 | C0102 | C0102 | Skin Cutaneous Melanoma |
| TCGA-HU-A4GU | A2402 | A3303 | B5101 | B5502 | C0102 | C1502 | Stomach adenocarcinoma |
| TCGA-FF-8042 | A3303 | A3403 | B5801 | B5801 | C0302 | C0302 | Lymphoid Neoplasm Diffuse Large B-cell Lymphoma |
| TCGA-XR-A8TC | A0326 | A7401 | B3501 | B4403 | C0401 | C0401 | Liver hepatocellular carcinoma |
| TCGA-AD-A5EI | A2902 | A3301 | B1503 | B1503 | C0210 | C0210 | Colon adenocarcinoma |
| TCGA-A6-5661 | A0202 | A3402 | B1801 | B5101 | C0210 | C1601 | Colon adenocarcinoma |
| TCGA-90-A4EE | A0101 | A0201 | B4403 | B4403 | C1601 | C1601 | Lung squamous cell carcinoma |
| TCGA-CI-6032 | A0206 | A2301 | B0801 | B4901 | C0701 | C0701 | Kidney renal clear cell carcinoma |
| TCGA-CM-5861 | A3001 | A3404 | B1302 | B4101 | C0602 | C1701 | Colon adenocarcinoma |
| TCGA-AA-3950 | A0122N | A0201 | B1501 | B2705 | C0202 | C0303 | Colon adenocarcinoma |
| TCGA-DU-6392 | A0101 | A2902 | B0801 | B4403 | C0701 | C1601 | Brain Lower Grade Glioma |
| TCGA-VR-AA7D | A3002 | A3004 | B4501 | B4501 | C0602 | C1601 | Esophageal carcinoma |

| Expected patient MHC binders | Observed patient MHC binders | Observed/ expected | p-val |
|---|---|---|---|
| 44.0939 | 13 | 0.295 | 0.00000000031 |
| 41.9031 | 24 | 0.573 | 0.00037043520 |
| 26.0852 | 13 | 0.498 | 0.00082312012 |

TABLE S6-continued

Immunoedited subjects from TCGA.

| | | | |
|---|---|---|---|
| 15.6429 | 6 | 0.384 | 0.00178142136 |
| 22.3299 | 11 | 0.493 | 0.00196043875 |
| 8.8916 | 2 | 0.225 | 0.00269152331 |
| 24.7529 | 14 | 0.566 | 0.00457841105 |
| 9.3801 | 3 | 0.320 | 0.00634408278 |
| 4.1931 | 0 | 0.000 | 0.00731436278 |
| 3.8517 | 0 | 0.000 | 0.00872800270 |
| 3.2859 | 0 | 0.000 | 0.01453692038 |
| 3.3544 | 0 | 0.000 | 0.02065550596 |
| 4.7547 | 1 | 0.210 | 0.02459995404 |
| 2.1206 | 0 | 0.000 | 0.02519037483 |
| 1.5558 | 0 | 0.000 | 0.02792634977 |
| 4.5870 | 1 | 0.218 | 0.02824416837 |
| 4.4461 | 1 | 0.225 | 0.03752230499 |
| 2.4062 | 0 | 0.000 | 0.03757148287 |
| 1.5889 | 0 | 0.000 | 0.04225146265 |
| 4.3154 | 1 | 0.232 | 0.04352150345 |
| 2.7070 | 0 | 0.000 | 0.04472055570 |
| 54.6497 | 44 | 0.805 | 0.04538654766 |
| 2.3716 | 0 | 0.000 | 0.04891212032 |

List of subjects with highest degrees of immunoediting in the TCGA ($p \leq 0.05$). Expected binders calculated by summing the probability of all individual variants in each patient being bound to an HLA allele in the TCGA. Observed binders is the summed number of variant/HLA pairs that generate at least one epitope across each variant. Observed/expected represents the degree of underrepresentation of presented neoantigens in each patient (0 being perfect immunoediting). Despite being ranked the lowest in significance for immunoediting, uterine cancer represents 5 of the top 10 patients with the most significant degrees of immunoediting. The most significantly immunoedited subject also ranks 3 of 7300 in number of immunogenically silent mutations.

All of the methods disclosed and claimed herein can be made and executed without undue experimentation in light of the present disclosure. While the compositions and methods of this disclosure have been described in terms of particular embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

IX. REFERENCES

The following references, to the extent that they provide exemplary procedural or other details supplementary to those set forth herein, are specifically incorporated herein by reference.

Adra et al., 1987. *Gene* 60:65-74
Austin-Ward and Villaseca, Revista *Medica* de Chile, 126 (7):838-845, 1998.
Ausubel et al., CURRENT PROTOCOLS IN MOLECULAR BIOLOGY, Greene Publishing Associates and John Wiley & Sons, NY, 1994.
Azuma et al., *Cell Immunol.*, 116(1):123-134, 1988.
Bisht et al., *Indian J. Cancer,* 47(4):443-451, 2010.
Boussif et al., *Proc Nat Acad Sci USA,* 92:7297-7301, 1995.
Bukowski et al., *Clinical Cancer Res.,* 4(10):2337-2347, 1998.
Camacho et al. (2004) *J Clin Oncology* 22(145): Abstract No. 2505.
Christodoulides et al., *Microbiology,* 144(Pt 11):3027-3037, 1998.
Choi, J. K., et al. 2001. *Stem Cells* 19, No. 3, 236-246.
Dao et al., *Nature Biotechnol.* 33: 1079-1086, 2015.
Davidson et al., *J. Immunother.,* 21(5):389-398, 1998.
de Felipe et al., 2004. *Traffic* 5: 616-626.
Dobson et al., 1982. *Nucleic Acids Res.* 10:2635-2637.
Fang et al., 2005. *Nat. Biotech* 23: 584-590.
Fong et al., *J. Immunol.* 166:4254-4259, 2001.
Ford et al., *Gene Therapy* 8:1-4, 2001.
Gunning et al., 1989. *Proc. Natl. Acad. Sci. USA* 84:4831-4835.
Gupta and Kanodia, Natl. *Med. J. India,* 15(4):202-207, 2002.
Hanibuchi et al., *Int. J. Cancer,* 78(4):480-485, 1998.
Hawley, R. G., et al. (1994) *Gene Ther.* 1:136-138.
Hawley, R. G., et al. (1996) *Proc. Natl. Acad. Sci. USA* 93:10297-10302.
Heemskerk et al., *Hum. Gene Ther.* 19:496-510 (2008).
Hellstrand et al., *Acta Oncologica,* 37(4):347-353, 1998.
Hermanson and Kaufman, *Front. Immunol.,* 6, 195, 2015.
Hollander, *Front. Immunol.,* 3:3, 2012.
Hui and Hashimoto, *Infection Immun.,* 66(11):5329-5336, 1998.
Hurwitz et al. (1998) *Proc. Natl. Acad. Sci. USA* 95(17): 10067-10071.
Husson et al., *J. Bacteriol.,* 172(2):519-524, 1990.
Jacobs et al., *Nature,* 327(6122):532-535, 1987.
Johnson et al., *Blood* 114:535-46 (2009).
Jolly, D. J. (1999). Emerging viral vectors. pp 209-40 in Friedmann T, ed.
Karasuyama et al., 1989. *J. Exp. Med.* 169:13.
Keller, G., et al. (1998) *Blood* 92:877-887.
Krisky et al., et al. 1998. *Gene Ther.* 5: 1517-30.
Lieberman, Pharmaceutical Dosage Forms (vols. 1-3, 1992)
Lloyd, The Art, Science and Technology of Pharmaceutical Compounding (1999)
Lotte et al., *Adv. Tuberc. Res.,* 21:107-93; 194-245, 1984.
Luelmo, *Am. Rev. Respir. Dis.,* 125(3 Pt 2):70-72, 1982.
Martin et al., *Nature,* 345(6277):739-743, 1990.

Mokyr et al. (1998) *Cancer Res.* 58:5301-5304.
Pardoll, *Nat. Rev. Cancer,* 12(4): 252-64, 2012b.
Pfeifer, A. and I. M. Verma, 2001, *Annu. Rev. Genomics Hum. Genet.* 2:177-211,
Pickar, Dosage Calculations, 1999.
Prochiantz, *Nat. Methods* 4:119-20, 2007.
Qin et al., *Proc. Natl. Acad. Sci. USA,* 95(24):14411-14416, 1998.
Rabinovich et al., *Science,* 265(5177):1401-1404, 1994.
Remington: The Science and Practice of Pharmacy, 20th Edition, 2003, Gennaro, Ed., Lippincott, Williams & Wilkins.
Remington's Pharmaceutical Sciences, 15th ed., pages 1035-1038 and 1570-1580, Mack Publishing Company, Easton, PA, 1980.
Sambrook et al., MOLECULAR CLONING, A LABORATORY MANUAL, Cold Springs Harbor Press (Cold Springs Harbor, NY 1989).
Schonfeld et al., *Mol. Ther.,* 23, 330-338, 2015.
Schumacher and Schreiber, *Science,* 348:69-74, 2015.
Shah et al., *PLoS One,* 8:e776781, 2013.
Singer-Sam et al., 1984. *Gene* 32:409-417.
Singleton et al., DICTIONARY OF MICROBIOLOGY AND MOLECULAR BIOLOGY, 2nd ed., J. Wiley & Sons (New York, N.Y. 1994).
Snapper et al., *Proc. Natl. Acad. Sci. USA,* 85(18):6987-6991, 1988.
Spanholtz et al., *PLoS One,* 6(6):e20740, 2011.
Szymczak et al., 2004. *Nat. Biotechnol.* 22: 589-594.
Takada et al., *J. Clin. Microbiol.,* 33(3):658-660, 1995.
Terakura et al. (2012) *Blood,* 1:72-82.
U.S. Pat. No. 4,435,386
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,579,945
U.S. Pat. No. 4,866,034
U.S. Pat. No. 4,877,611
U.S. Pat. No. 4,937,190
U.S. Pat. No. 4,950,645
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,207,156
U.S. Pat. No. 6,218,181
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,735,553
Wang et al. (2012) *J. Immunother.* 35(9):689-701.
WO 00/37504
WO 01/14424
WO 91/16347
WO 98/42752
WO1995/001994
WO1998/042752
WO2000/037504
WO2001/014424
WO2009/101611
WO2009/114335
WO2010/027827
WO2011/066342
WO2015016718
Yamamoto et al., *Jpn. J. Cancer Res.,* 79:866 873, 1988.
Yin et al., *J. Biol. Resp. Modif.,* 8:190 205, 1989.
Abelin, J. G., Keskin, D. B., Sarkizova, S., Hartigan, C. R., Zhang, W., Sidney, J., Stevens, J., Lane, W., Zhang, G. L., Eisenhaure, T. M., et al. (2017). Mass Spectrometry Profiling of HLA-Associated Peptidomes in Mono-allelic Cells Enables More Accurate Epitope Prediction. Immunity 46, 315-326.
Alexandrov, L. B., Nik-Zainal, S., Wedge, D. C., Aparicio, S. A. J. R., Behjati, S., Biankin, A. V., Bignell, G. R., Bolli, N., Borg, A., Børresen-Dale, A.-L., et al. (2013). Signatures of mutational processes in human cancer. Nature 500, 415-421.
Andreatta, M., and Nielsen, M. (2016). Gapped sequence alignment using artificial neural networks: application to the MHC class I system. Bioinformatics 32, 511-517.
Bai, Y., Ni, M., Cooper, B., Wei, Y., and Fury, W. (2014). Inference of high resolution HLA types using genome-wide RNA or DNA sequencing reads. BMC Genomics 15, 325.
Coley, W. B. (1891a). II. Contribution to the Knowledge of Sarcoma. Ann Surg 14, 199-220.
de Sousa, J. R., Sotto, M. N., and Simões Quaresma, J. A. (2017). Leprosy As a Complex Infection: Breakdown of the Th1 and Th2 Immune Paradigm in the Immunopathogenesis of the Disease. Frontiers in Immunology 8.
Dunn, G. P., Old, L. J., and Schreiber, R. D. (2004). The Immunobiology of Cancer Immunosurveillance and Immunoediting. Immunity 21, 137-148.
Eng, J. K., McCormack, A. L., and Yates, J. R. (1994). An approach to correlate tandem mass spectral data of peptides with amino acid sequences in a protein database. J Am Soc Mass Spectrom 5, 976-989.
Falk, K., Rotzschke, O., Stevanovic, S., Jung, G., and Rammensee, H. G. (1991). Allele-specific motifs revealed by sequencing of self-peptides eluted from MHC molecules. Nature 351, 290-296.
Flexner, S., and Jobling, J. W. (1908). SERUM TREATMENT OF EPIDEMIC CEREBRO-SPINAL MENINGITIS. The Journal of Experimental Medicine 10, 141-203.
Fritsch, E. F., Rajasagi, M., Ott, P. A., Brusic, V., Hacohen, N., and Wu, C. J. (2014). HLA-Binding Properties of Tumor Neoepitopes in Humans. Cancer Immunology Research 2, 522-529.
Gallagher, M. P., Kelly, P. J., Jardine, M., Perkovic, V., Cass, A., Craig, J. C., Eris, J., and Webster, A. C. (2010). Long-Term Cancer Risk of Immunosuppressive Regimens after Kidney Transplantation. Journal of the American Society of Nephrology: JASN 21, 852-858.
Gragert, L., Madbouly, A., Freeman, J., and Maiers, M. (2013). Six-locus high resolution HLA haplotype frequencies derived from mixed-resolution DNA typing for the entire US donor registry. Human Immunology 74, 1313-1320.
Grulich, A. E., van Leeuwen, M. T., Falster, M. O., and Vajdic, C. M. (2007). Incidence of cancers in people with HIV/AIDS compared with immunosuppressed transplant recipients: a meta-analysis. The Lancet 370, 59-67.
He, Y., Rappuoli, R., De Groot, A. S., and Chen, R. T. (2010). Emerging Vaccine Informatics. Journal of Biomedicine and Biotechnology 2010, 26. Abelin, J. G., Keskin, D. B., Sarkizova, S., Hartigan, C. R., Zhang, W., Sidney, J., Stevens, J., Lane, W., Zhang, G. L., Eisenhaure, T. M., et al. (2017). Mass Spectrometry Profiling of HLA-Associated Peptidomes in Mono-allelic Cells Enables More Accurate Epitope Prediction. Immunity 46, 315-326.

Kall, L., Canterbury, J. D., Weston, J., Noble, W. S., and MacCoss, M. J. (2007). Semi-supervised learning for peptide identification from shotgun proteomics datasets. Nat Methods 4, 923-925.

Kowalewski, D. J., and Stevanovic, S. (2013). Biochemical large-scale identification of MHC class I ligands. Methods Mol Biol 960, 145-157.

Fritsch, E. F., Rajasagi, M., Ott, P. A., Brusic, V., Hacohen, N., and Wu, C. J. (2014). HLA-Binding Properties of Tumor Neoepitopes in Humans. Cancer Immunology Research 2, 522-529.

Himoudi, N., Yan, M., Papanastasiou, A., and Anderson, J. (2008). MYCN as a target for cancer immunotherapy. Cancer Immunology, Immunotherapy 57, 693-700.

Ichim, C. V. (2005). Revisiting immunosurveillance and immunostimulation: Implications for cancer immunotherapy. Journal of Translational Medicine 3, 8.

Lundegaard, C., Lamberth, K., Harndahl, M., Buus, S., Lund, O., and Nielsen, M. (2008). NetMHC-3.0: accurate web accessible predictions of human, mouse and monkey MHC class I affinities for peptides of length 8-11. Nucleic Acids Research 36, W509-W512.

Louveau, A., Harris, T. H., and Kipnis, J. (2015a). Revisiting the Mechanisms of CNS Immune Privilege. Trends in Immunology 36, 569-577.

Louveau, A., Smirnov, I., Keyes, T. J., Eccles, J. D., Rouhani, S. J., Peske, J. D., Derecki, N. C., Castle, D., Mandell, J. W., Lee, K. S., et al. (2015b). Structural and functional features of central nervous system lymphatic vessels. Nature 523, 337.

Maiers, M., Gragert, L., and Klitz, W. (2007). High-resolution HLA alleles and haplotypes in the United States population. Human Immunology 68, 779-788.

Marty, R., Kaabinejadian, S., Rossell, D., Slifker, MJ., van de Haar, J., Engin, H. B., de Prisco, N., Ideker, T., Hildebrand, W. H., Font-Burgada, J., et al. (2017). MHC-I Genotype Restricts the Oncogenic Mutational Landscape. Cell 171, 1272-1283.e1215.

Nielsen, M., Lundegaard, C., Blicher, T., Lamberth, K., Harndahl, M., Justesen, S., Roder, G., Peters, B., Sette, A., Lund, O., et al. (2007). NetMHCpan, a Method for Quantitative Predictions of Peptide Binding to Any HLA-A and -B Locus Protein of Known Sequence. PLOS ONE 2, e796.

Penn, I., and Starzl, T. E. (1973). Immunosuppression and Cancer. Transplantation proceedings 5, 943-947.

Prehn, R. T. (1972). The Immune Reaction as a Stimulator of Tumor Growth. Science 176, 170-171.

Rammensee, H., Bachmann, J., Emmerich, N. P., Bachor, O. A., and Stevanovic, S. (1999). SYFPEITHI: database for MHC ligands and peptide motifs. Immunogenetics 50, 213-219.

Robinson, J., Halliwell, J. A., Hayhurst, J. D., Flicek, P., Parham, P., and Marsh, Steven G E. (2015).

The IPD and IMGT/HLA database: allele variant databases. Nucleic Acids Research 43, D423-D431.

Rooney, M. S., Shukla, S. A., Wu, C. J., Getz, G., and Hacohen, N. (2015). Molecular and genetic properties of tumors associated with local immune cytolytic activity. Cell 160, 48-61.

Tilan, J., and Kitlinska, J. (2016). Neuropeptide Y (NPY) in tumor growth and progression: Lessons learned from pediatric oncology. Neuropeptides 55, 55-66.

Tran, E., Robbins, P. F., Lu, Y.-C., Prickett, T. D., Gartner, JJ., Jia, L., Pasetto, A., Zheng, Z., Ray, S., Groh, E. M., et al. (2016). T-Cell Transfer Therapy Targeting Mutant KRAS in Cancer. The New England journal of medicine 375, 2255-2262.

Trowsdale, J., and Knight, J. C. (2013). Major Histocompatibility Complex Genomics and Human Disease. Annual Review of Genomics and Human Genetics 14, 301-323.

Vogelstein, B., Papadopoulos, N., Velculescu, V. E., Zhou, S., Diaz, L. A., and Kinzler, K. W. (2013). Cancer Genome Landscapes. Science (New York, NY) 339, 1546-1558.

Winograd, R., Byrne, K. T., Evans, R. A., Odorizzi, P. M., Meyer, A. R. L, Bajor, D. L., Clendenin, C., Stanger, B. Z., Furth, E. E., Wherry, E. J., et al. (2015). Induction of T-cell Immunity Overcomes Complete Resistance to PD-1 and CTLA-4 Blockade and Improves Survival in Pancreatic Carcinoma. Cancer Immunology Research 3, 399-411.

What is claimed is:

1. A chimeric antigen receptor (CAR) protein, wherein the CAR protein binds to an antigen selected from the group consisting of

FLDETLRSLA, (SEQ ID NO: 2)

QYNPIRTTF, (SEQ ID NO: 3)

ALLSGVRQV, and (SEQ ID NO: 7)

SAAMVFSAL. (SEQ ID NO: 9)

2. A polynucleotide molecule encoding the CAR protein of claim 1.

3. The polynucleotide molecule of claim 2, further comprising a promoter active in eukaryotic cells.

4. The polynucleotide molecule of claim 2, wherein the polynucleotide is an expression vector.

5. An expression vector encoding the CAR protein of claim 1, wherein the coding region for the CAR protein is under the control of a promoter active in eukaryotic cells.

6. An engineered T cell comprising a polynucleotide molecule encoding a chimeric antigen receptor (CAR) that binds an antigen selected from the group consisting of

FLDETLRSLA, (SEQ ID NO: 2)

QYNPIRTTF, (SEQ ID NO: 3)

ALLSGVRQV, and (SEQ ID NO: 7)

SAAMVFSAL. (SEQ ID NO: 9)

7. The engineered cell of claim 6, further comprising a transposase.

8. A method of treating cancer in a human subject in need thereof comprising administering to the subject an effective amount of a therapeutic composition comprising one or more of the engineered cells of claim 6.

9. A method of generating an anti-cancer immune response in a subject comprising administering to said subject a vaccine composition comprising more than one of the antigens selected from the group consisting

FLDETLRSLA, (SEQ ID NO: 2)

QYNPIRTTF, (SEQ ID NO: 3)

ALLSGVRQV, and (SEQ ID NO: 7)

SAAMVFSAL. (SEQ ID NO: 9)

10. The CAR protein of claim 1, wherein the CAR protein binds to FLDETLRSLA (SEQ ID NO: 2).

11. The CAR protein of claim 1, wherein the CAR protein binds to QYNPIRTTF (SEQ ID NO: 3).

12. The CAR protein of claim 1, wherein the CAR protein binds to ALLSGVRQV (SEQ ID NO: 7).

13. The CAR protein of claim 1, wherein the CAR protein binds to SAAMVFSAL (SEQ ID NO: 9).

* * * * *

SEQUENCE LISTING

```
<160> NUMBER OF SEQ ID NOS: 164

<210> SEQ ID NO 1
<211> LENGTH: 10
<212> TYPE: PRT
<213> ORGANISM: Homo sapiens

<400> SEQUENCE: 1

Leu Leu Pro Leu Leu Pro Pro Leu Ser Pro
1               5                   10

<210> SEQ ID NO 2
<211> LENGTH: 10
<212> TYPE: PRT
<213> ORGANISM: Zea mays

<400> SEQUENCE: 2

Phe Leu Asp Glu Thr Leu Arg Ser Leu Ala
1               5                   10
```

```
<210> SEQ ID NO 3
<211> LENGTH: 9
<212> TYPE: PRT
<213> ORGANISM: Homo sapiens

<400> SEQUENCE: 3

Gln Tyr Asn Pro Ile Arg Thr Thr Phe
1               5

<210> SEQ ID NO 4
<211> LENGTH: 9
<212> TYPE: PRT
<213> ORGANISM: Homo sapiens

<400> SEQUENCE: 4

Ser Tyr Gln Lys Val Ile Glu Leu Phe
1               5

<210> SEQ ID NO 5
<211> LENGTH: 9
<212> TYPE: PRT
<213> ORGANISM: Homo sapiens

<400> SEQUENCE: 5

Ile Tyr Pro Asp Ile Thr Tyr Ser Leu
1               5

<210> SEQ ID NO 6
<211> LENGTH: 9
<212> TYPE: PRT
<213> ORGANISM: Homo sapiens

<400> SEQUENCE: 6

Phe Leu Ile Glu Asn Leu Leu Ala Ala
1               5

<210> SEQ ID NO 7
<211> LENGTH: 9
<212> TYPE: PRT
<213> ORGANISM: Homo sapiens

<400> SEQUENCE: 7

Ala Leu Leu Ser Gly Val Arg Gln Val
1               5

<210> SEQ ID NO 8
<211> LENGTH: 11
<212> TYPE: PRT
<213> ORGANISM: Homo sapiens

<400> SEQUENCE: 8

Val Leu Phe Glu Asn Thr Asp Ser Val His Leu
1               5                   10

<210> SEQ ID NO 9
<211> LENGTH: 9
<212> TYPE: PRT
<213> ORGANISM: Homo sapiens

<400> SEQUENCE: 9

Ser Ala Ala Met Val Phe Ser Ala Leu
1               5

<210> SEQ ID NO 10
```

```
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 11
<211> LENGTH: 63
<212> TYPE: DNA
<213> ORGANISM: Artificial Sequence
<220> FEATURE:
<223> OTHER INFORMATION: Synthetic primer

<400> SEQUENCE: 11
atctacatct gggctccact ggcaggaacc tgtggcgtgc tgctgctgtc cctggtcatc        60
aca                                                                     63

<210> SEQ ID NO 12
<211> LENGTH: 27
<212> TYPE: PRT
<213> ORGANISM: Artificial Sequence
<220> FEATURE:
<223> OTHER INFORMATION: Synthetic peptide

<400> SEQUENCE: 12

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 13
<211> LENGTH: 81
<212> TYPE: DNA
<213> ORGANISM: Artificial Sequence
<220> FEATURE:
<223> OTHER INFORMATION: Synthetic peptide

<400> SEQUENCE: 13
ttttgggtgc tggtggtggt tggtggagtc ctggcttgct atagcttgct agtaacagtg        60
gcctttatta ttttctgggt g                                                  81

<210> SEQ ID NO 14
<211> LENGTH: 339
<212> TYPE: DNA
<213> ORGANISM: Artificial Sequence
<220> FEATURE:
<223> OTHER INFORMATION: Synthetic primer

<400> SEQUENCE: 14
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatgggggg aaagccgaga aggaagaacc ctcaggaagg cctgtacaat       180
gaactgcaga aagataagat ggcggaggcc tacagtgaga ttgggatgaa aggcgagcgc       240 cggagggggca aggggcacga tggcctttac cagggtctca gtacagccac caaggacacc      300
tacgacgccc ttcacatgca ggccctgccc cctcgctaa                              339
```

<210> SEQ ID NO 15
<211> LENGTH: 41
<212> TYPE: PRT
<213> ORGANISM: Artificial Sequence
<220> FEATURE:
<223> OTHER INFORMATION: Synthetic peptide

<400> SEQUENCE: 15

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 16
<211> LENGTH: 123
<212> TYPE: DNA
<213> ORGANISM: Artificial Sequence
<220> FEATURE:
<223> OTHER INFORMATION: Synthetic peptide

<400> SEQUENCE: 16
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 17
<211> LENGTH: 42
<212> TYPE: PRT
<213> ORGANISM: Artificial Sequence
<220> FEATURE:
<223> OTHER INFORMATION: Synthetic peptide

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 18
<211> LENGTH: 126
<212> TYPE: DNA
<213> ORGANISM: Artificial Sequence
<220> FEATURE:
<223> OTHER INFORMATION: Synthetic primer

<400> SEQUENCE: 18
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide -continued

```
<400> SEQUENCE: 19

Gly Gly Gly Gly Ser Gly Gly Gly Ser Gly Gly Gly Gly Ser
1               5                   10                  15

<210> SEQ ID NO 20
<211> LENGTH: 63
<212> TYPE: DNA
<213> ORGANISM: Artificial Sequence
<220> FEATURE:
<223> OTHER INFORMATION: Synthetic primer

<400> SEQUENCE: 20
atggccttac cagtgaccgc cttgctcctg ccgctggcct tgctgctcca cgccgccagg      60
ccg                                                                   63

<210> SEQ ID NO 21
<211> LENGTH: 45
<212> TYPE: DNA
<213> ORGANISM: Artificial Sequence
<220> FEATURE:
<223> OTHER INFORMATION: Synthetic primer

<400> SEQUENCE: 21
ggtggaggcg gttcaggtgg cggcggttcg ggcggtggcg gctct                     45

<210> SEQ ID NO 22
<211> LENGTH: 135
<212> TYPE: DNA
<213> ORGANISM: Artificial Sequence
<220> FEATURE:
<223> OTHER INFORMATION: Synthetic primer

<400> SEQUENCE: 22
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg    120
gacttcgcct gtgat                                                    135

<210> SEQ ID NO 23
<211> LENGTH: 9
<212> TYPE: PRT
<213> ORGANISM: Homo sapiens

<400> SEQUENCE: 23

Leu Leu Leu Pro Leu Leu Pro Pro Leu
1               5

<210> SEQ ID NO 24
<211> LENGTH: 12
<212> TYPE: PRT
<213> ORGANISM: Homo sapiens

<400> SEQUENCE: 24

Leu Leu Leu Pro Leu Leu Pro Pro Leu Ser Pro Ser
1               5                   10

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 25

Thr Val Arg Pro Lys Asn Ala Ala Leu
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Lys Ala Thr Glu Tyr Val His Ser Leu
1               5

<210> SEQ ID NO 27
<211> LENGTH: 17
<212> TYPE: PRT
<213> ORGANISM: Artificial sequence
<220> FEATURE:
<223> OTHER INFORMATION: Synthetic peptide

<400> SEQUENCE: 27

Leu Glu Arg Gln Arg Arg Asn Asp Leu Arg Ser Ser Phe Leu Thr Leu
1               5                   10                  15

Arg

<210> SEQ ID NO 28
<211> LENGTH: 33
<212> TYPE: PRT
<213> ORGANISM: Artificial sequence
<220> FEATURE:
<223> OTHER INFORMATION: Synthetic peptide

<400> SEQUENCE: 28

Thr Val Arg Pro Lys Asn Ala Ala Leu Gly Pro Gly Arg Ala Gln Ser
1               5                   10                  15

Ser Glu Leu Ile Leu Lys Arg Cys Leu Pro Ile His Gln Gln His Asn
            20                  25                  30

Tyr

<210> SEQ ID NO 29
<211> LENGTH: 11
<212> TYPE: PRT
<213> ORGANISM: Artificial sequence
<220> FEATURE:
<223> OTHER INFORMATION: Synthetic peptide

<400> SEQUENCE: 29

Tyr Pro Ser Lys Pro Asp Asn Pro Gly Glu Asp
1               5                   10

<210> SEQ ID NO 30
<211> LENGTH: 9
<212> TYPE: PRT
<213> ORGANISM: Artificial sequence
<220> FEATURE:
<223> OTHER INFORMATION: Synthetic peptide

<400> SEQUENCE: 30

Arg Tyr Tyr Ser Ala Leu Arg His Tyr
1               5
```

```
<210> SEQ ID NO 31
<211> LENGTH: 11
<212> TYPE: PRT
<213> ORGANISM: Artificial sequence
<220> FEATURE:
<223> OTHER INFORMATION: Synthetic peptide

<400> SEQUENCE: 31

Ser Pro Glu Thr Leu Ile Ser Asp Leu Leu Met
1               5                   10

<210> SEQ ID NO 32
<211> LENGTH: 8
<212> TYPE: PRT
<213> ORGANISM: Artificial sequence
<220> FEATURE:
<223> OTHER INFORMATION: Synthetic peptide

<400> SEQUENCE: 32

Thr Leu Ile Ser Asp Leu Leu Met
1               5

<210> SEQ ID NO 33
<211> LENGTH: 11
<212> TYPE: PRT
<213> ORGANISM: Artificial sequence
<220> FEATURE:
<223> OTHER INFORMATION: Synthetic peptide

<400> SEQUENCE: 33

Ser Ser Pro Glu Thr Leu Ile Ser Asp Leu Leu
1               5                   10

<210> SEQ ID NO 34
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

Ser Ala Leu Arg His Tyr Ile Asn Leu
1               5

<210> SEQ ID NO 35
<211> LENGTH: 10
<212> TYPE: PRT
<213> ORGANISM: Artificial sequence
<220> FEATURE:
<223> OTHER INFORMATION: Synthetic peptide

<400> SEQUENCE: 35

Ser Ser Pro Glu Thr Leu Ile Ser Asp Leu
1               5                   10

<210> SEQ ID NO 36
<211> LENGTH: 10
<212> TYPE: PRT
<213> ORGANISM: Artificial sequence
<220> FEATURE:
<223> OTHER INFORMATION: Synthetic peptide

<400> SEQUENCE: 36

Ser Pro Glu Thr Leu Ile Ser Asp Leu Leu
1               5                   10

<210> SEQ ID NO 37
```

```
<211> LENGTH: 10
<212> TYPE: PRT
<213> ORGANISM: Artificial sequence
<220> FEATURE:
<223> OTHER INFORMATION: Synthetic peptide

<400> SEQUENCE: 37

Tyr Pro Ser Lys Pro Asp Asn Pro Gly Glu
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic peptide

<400> SEQUENCE: 38

Tyr Pro Ser Lys Pro Asp Asn Pro Gly Glu Asp Ala
1               5                   10

<210> SEQ ID NO 39
<211> LENGTH: 8
<212> TYPE: PRT
<213> ORGANISM: Artificial sequence
<220> FEATURE:
<223> OTHER INFORMATION: Synthetic peptide

<400> SEQUENCE: 39

Ser Thr Glu Asn Val Pro Arg Thr
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic peptide

<400> SEQUENCE: 40

Thr Glu Asn Val Pro Arg Thr Arg
1               5

<210> SEQ ID NO 41
<211> LENGTH: 10
<212> TYPE: PRT
<213> ORGANISM: Artificial sequence
<220> FEATURE:
<223> OTHER INFORMATION: Synthetic peptide

<400> SEQUENCE: 41

Arg Glu Ser Thr Glu Asn Val Pro Arg Thr
1               5                   10

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Tyr Pro Ser Lys Pro Asp Asn Pro Gly
1               5

<210> SEQ ID NO 43
<211> LENGTH: 11
```

```
<212> TYPE: PRT
<213> ORGANISM: Artificial sequence
<220> FEATURE:
<223> OTHER INFORMATION: Synthetic peptide

<400> SEQUENCE: 43

Ser Lys Pro Asp Asn Pro Gly Glu Asp Ala Pro
1               5                   10

<210> SEQ ID NO 44
<211> LENGTH: 9
<212> TYPE: PRT
<213> ORGANISM: Artificial sequence
<220> FEATURE:
<223> OTHER INFORMATION: Synthetic peptide

<400> SEQUENCE: 44

Arg Glu Ser Thr Glu Asn Val Pro Arg
1               5

<210> SEQ ID NO 45
<211> LENGTH: 9
<212> TYPE: PRT
<213> ORGANISM: Artificial sequence
<220> FEATURE:
<223> OTHER INFORMATION: Synthetic peptide

<400> SEQUENCE: 45

Glu Ser Thr Glu Asn Val Pro Arg Thr
1               5

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Ser Ala Leu Arg His Tyr Ile Asn Leu Ile Thr Arg
1               5                   10

<210> SEQ ID NO 47
<211> LENGTH: 9
<212> TYPE: PRT
<213> ORGANISM: Artificial sequence
<220> FEATURE:
<223> OTHER INFORMATION: Synthetic peptide

<400> SEQUENCE: 47

Arg Tyr Tyr Ser Ala Leu Arg His Tyr
1               5

<210> SEQ ID NO 48
<211> LENGTH: 9
<212> TYPE: PRT
<213> ORGANISM: Artificial sequence
<220> FEATURE:
<223> OTHER INFORMATION: Synthetic peptide

<400> SEQUENCE: 48

Ser Ala Leu Arg His Tyr Ile Asn Leu
1               5

<210> SEQ ID NO 49
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 49

His Tyr Ile Asn Leu Ile Thr Arg
1               5

<210> SEQ ID NO 50
<211> LENGTH: 11
<212> TYPE: PRT
<213> ORGANISM: Artificial sequence
<220> FEATURE:
<223> OTHER INFORMATION: Synthetic peptide

<400> SEQUENCE: 50

Tyr Tyr Ser Ala Leu Arg His Tyr Ile Asn Leu
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic peptide

<400> SEQUENCE: 51

Tyr Ser Ala Leu Arg His Tyr Ile Asn Leu
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Arg Tyr Tyr Ser Ala Leu Arg His Tyr Ile Asn Leu
1               5                   10

<210> SEQ ID NO 53
<211> LENGTH: 22
<212> TYPE: PRT
<213> ORGANISM: Artificial sequence
<220> FEATURE:
<223> OTHER INFORMATION: Synthetic peptide

<400> SEQUENCE: 53

Tyr Pro Ser Lys Pro Asp Asn Pro Gly Glu Asp Ala Pro Ala Glu Asp
1               5                   10                  15

Met Ala Arg Tyr Tyr Ser
            20

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Ser Ala Leu Arg His Tyr Ile Asn Leu Ile Thr Arg
1               5                   10

<210> SEQ ID NO 55
```

```
<211> LENGTH: 11
<212> TYPE: PRT
<213> ORGANISM: Artificial sequence
<220> FEATURE:
<223> OTHER INFORMATION: Synthetic peptide

<400> SEQUENCE: 55

Tyr Pro Ser Lys Pro Asp Asn Pro Gly Glu Asp
1               5                   10

<210> SEQ ID NO 56
<211> LENGTH: 16
<212> TYPE: PRT
<213> ORGANISM: Artificial sequence
<220> FEATURE:
<223> OTHER INFORMATION: Synthetic peptide

<400> SEQUENCE: 56

Arg Glu Ser Thr Glu Asn Val Pro Arg Thr Arg Leu Glu Asp Pro Ala
1               5                   10                  15

<210> SEQ ID NO 57
<211> LENGTH: 17
<212> TYPE: PRT
<213> ORGANISM: Artificial sequence
<220> FEATURE:
<223> OTHER INFORMATION: Synthetic peptide

<400> SEQUENCE: 57

Glu Ser Thr Glu Asn Val Pro Arg Thr Arg Leu Glu Asp Pro Ala Met
1               5                   10                  15

Trp

<210> SEQ ID NO 58
<211> LENGTH: 17
<212> TYPE: PRT
<213> ORGANISM: Artificial sequence
<220> FEATURE:
<223> OTHER INFORMATION: Synthetic peptide

<400> SEQUENCE: 58

Met Arg Glu Ser Thr Glu Asn Val Pro Arg Thr Arg Leu Glu Asp Pro
1               5                   10                  15

Ala

<210> SEQ ID NO 59
<211> LENGTH: 13
<212> TYPE: PRT
<213> ORGANISM: Artificial sequence
<220> FEATURE:
<223> OTHER INFORMATION: Synthetic peptide

<400> SEQUENCE: 59

Arg Glu Ser Thr Glu Asn Val Pro Arg Thr Arg Leu Glu
1               5                   10

<210> SEQ ID NO 60
<211> LENGTH: 16
<212> TYPE: PRT
<213> ORGANISM: Artificial sequence
<220> FEATURE:
<223> OTHER INFORMATION: Synthetic peptide

<400> SEQUENCE: 60

Ser Thr Glu Asn Val Pro Arg Thr Arg Leu Glu Asp Pro Ala Met Trp
1               5                   10                  15
```

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Tyr Pro Ser Lys Pro Asp Asn Pro Gly
1               5

<210> SEQ ID NO 62
<211> LENGTH: 21
<212> TYPE: PRT
<213> ORGANISM: Artificial sequence
<220> FEATURE:
<223> OTHER INFORMATION: Synthetic peptide

<400> SEQUENCE: 62

Ser Ser Pro Glu Thr Leu Ile Ser Asp Leu Leu Met Arg Glu Ser Thr
1               5                   10                  15

Glu Asn Val Pro Arg
            20

<210> SEQ ID NO 63
<211> LENGTH: 19
<212> TYPE: PRT
<213> ORGANISM: Artificial sequence
<220> FEATURE:
<223> OTHER INFORMATION: Synthetic peptide

<400> SEQUENCE: 63

Met Arg Glu Ser Thr Glu Asn Val Pro Arg Thr Arg Leu Glu Asp Pro
1               5                   10                  15

Ala Met Trp

<210> SEQ ID NO 64
<211> LENGTH: 12
<212> TYPE: PRT
<213> ORGANISM: Artificial sequence
<220> FEATURE:
<223> OTHER INFORMATION: Synthetic peptide

<400> SEQUENCE: 64

Glu Ser Thr Glu Asn Val Pro Arg Thr Arg Leu Glu
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic peptide

<400> SEQUENCE: 65

Leu Arg His Tyr Ile Asn Leu Ile Thr Arg
1               5                   10

<210> SEQ ID NO 66
<211> LENGTH: 21
<212> TYPE: PRT
<213> ORGANISM: Artificial sequence
<220> FEATURE:
<223> OTHER INFORMATION: Synthetic peptide

```
<400> SEQUENCE: 66

Tyr Pro Ser Lys Pro Asp Asn Pro Gly Glu Asp Ala Pro Ala Glu Asp
1               5                   10                  15

Met Ala Arg Tyr Tyr
            20

<210> SEQ ID NO 67
<211> LENGTH: 19
<212> TYPE: PRT
<213> ORGANISM: Artificial sequence
<220> FEATURE:
<223> OTHER INFORMATION: Synthetic peptide

<400> SEQUENCE: 67

Ala Pro Ala Glu Asp Met Ala Arg Tyr Tyr Ser Ala Leu Arg His Tyr
1               5                   10                  15

Ile Asn Leu

<210> SEQ ID NO 68
<211> LENGTH: 20
<212> TYPE: PRT
<213> ORGANISM: Artificial sequence
<220> FEATURE:
<223> OTHER INFORMATION: Synthetic peptide

<400> SEQUENCE: 68

Tyr Pro Ser Lys Pro Asp Asn Pro Gly Glu Asp Ala Pro Ala Glu Asp
1               5                   10                  15

Met Ala Arg Tyr
            20

<210> SEQ ID NO 69
<211> LENGTH: 24
<212> TYPE: PRT
<213> ORGANISM: Artificial sequence
<220> FEATURE:
<223> OTHER INFORMATION: Synthetic peptide

<400> SEQUENCE: 69

Tyr Pro Ser Lys Pro Asp Asn Pro Gly Glu Asp Ala Pro Ala Glu Asp
1               5                   10                  15

Met Ala Arg Tyr Tyr Ser Ala Leu
            20

<210> SEQ ID NO 70
<211> LENGTH: 14
<212> TYPE: PRT
<213> ORGANISM: Artificial sequence
<220> FEATURE:
<223> OTHER INFORMATION: Synthetic peptide

<400> SEQUENCE: 70

Tyr Ser Ala Leu Arg His Tyr Ile Asn Leu Ile Thr Arg Gln
1               5                   10

<210> SEQ ID NO 71
<211> LENGTH: 18
<212> TYPE: PRT
<213> ORGANISM: Artificial sequence
<220> FEATURE:
<223> OTHER INFORMATION: Synthetic peptide
```

<400> SEQUENCE: 71

Ala Pro Ala Glu Asp Met Ala Arg Tyr Tyr Ser Ala Leu Arg His Tyr
1               5                   10                  15

Ile Asn

<210> SEQ ID NO 72
<211> LENGTH: 23
<212> TYPE: PRT
<213> ORGANISM: Artificial sequence
<220> FEATURE:
<223> OTHER INFORMATION: Synthetic peptide

<400> SEQUENCE: 72

Tyr Pro Ser Lys Pro Asp Asn Pro Gly Glu Asp Ala Pro Ala Glu Asp
1               5                   10                  15

Met Ala Arg Tyr Tyr Ser Ala
            20

<210> SEQ ID NO 73
<211> LENGTH: 25
<212> TYPE: PRT
<213> ORGANISM: Artificial sequence
<220> FEATURE:
<223> OTHER INFORMATION: Synthetic peptide

<400> SEQUENCE: 73

Ser Lys Pro Asp Asn Pro Gly Glu Asp Ala Pro Ala Glu Asp Met Ala
1               5                   10                  15

Arg Tyr Tyr Ser Ala Leu Arg His Tyr
            20                  25

<210> SEQ ID NO 74
<211> LENGTH: 16
<212> TYPE: PRT
<213> ORGANISM: Artificial sequence
<220> FEATURE:
<223> OTHER INFORMATION: Synthetic peptide

<400> SEQUENCE: 74

Leu Arg His Tyr Ile Asn Leu Ile Thr Arg Gln Arg Tyr Gly Lys Arg
1               5                   10                  15

<210> SEQ ID NO 75
<211> LENGTH: 14
<212> TYPE: PRT
<213> ORGANISM: Artificial sequence
<220> FEATURE:
<223> OTHER INFORMATION: Synthetic peptide

<400> SEQUENCE: 75

Asp Met Ala Arg Tyr Tyr Ser Ala Leu Arg His Tyr Ile Asn
1               5                   10

<210> SEQ ID NO 76
<211> LENGTH: 15
<212> TYPE: PRT
<213> ORGANISM: Artificial sequence
<220> FEATURE:
<223> OTHER INFORMATION: Synthetic peptide

<400> SEQUENCE: 76

Asp Met Ala Arg Tyr Tyr Ser Ala Leu Arg His Tyr Ile Asn Leu
1               5                   10                  15

```
<210> SEQ ID NO 77
<211> LENGTH: 17
<212> TYPE: PRT
<213> ORGANISM: Artificial sequence
<220> FEATURE:
<223> OTHER INFORMATION: Synthetic peptide

<400> SEQUENCE: 77

Ala Glu Asp Met Ala Arg Tyr Tyr Ser Ala Leu Arg His Tyr Ile Asn
1               5                   10                  15

Leu

<210> SEQ ID NO 78
<211> LENGTH: 13
<212> TYPE: PRT
<213> ORGANISM: Artificial sequence
<220> FEATURE:
<223> OTHER INFORMATION: Synthetic peptide

<400> SEQUENCE: 78

Ala Arg Tyr Tyr Ser Ala Leu Arg His Tyr Ile Asn Leu
1               5                   10

<210> SEQ ID NO 79
<211> LENGTH: 19
<212> TYPE: PRT
<213> ORGANISM: Artificial sequence
<220> FEATURE:
<223> OTHER INFORMATION: Synthetic peptide

<400> SEQUENCE: 79

Asp Met Ala Arg Tyr Tyr Ser Ala Leu Arg His Tyr Ile Asn Leu Ile
1               5                   10                  15

Thr Arg Gln

<210> SEQ ID NO 80
<211> LENGTH: 20
<212> TYPE: PRT
<213> ORGANISM: Artificial sequence
<220> FEATURE:
<223> OTHER INFORMATION: Synthetic peptide

<400> SEQUENCE: 80

Asp Ala Pro Ala Glu Asp Met Ala Arg Tyr Tyr Ser Ala Leu Arg His
1               5                   10                  15

Tyr Ile Asn Leu
            20

<210> SEQ ID NO 81
<211> LENGTH: 16
<212> TYPE: PRT
<213> ORGANISM: Artificial sequence
<220> FEATURE:
<223> OTHER INFORMATION: Synthetic peptide

<400> SEQUENCE: 81

Ala Glu Asp Met Ala Arg Tyr Tyr Ser Ala Leu Arg His Tyr Ile Asn
1               5                   10                  15

<210> SEQ ID NO 82
<211> LENGTH: 23
<212> TYPE: PRT
<213> ORGANISM: Artificial sequence
<220> FEATURE:
<223> OTHER INFORMATION: Synthetic peptide
```

<400> SEQUENCE: 82

Ser Ser Pro Glu Thr Leu Ile Ser Asp Leu Leu Met Arg Glu Ser Thr
1               5                   10                  15

Glu Asn Val Pro Arg Thr Arg
            20

<210> SEQ ID NO 83
<211> LENGTH: 18
<212> TYPE: PRT
<213> ORGANISM: Artificial sequence
<220> FEATURE:
<223> OTHER INFORMATION: Synthetic peptide

<400> SEQUENCE: 83

Tyr Pro Ser Lys Pro Asp Asn Pro Gly Glu Asp Ala Pro Ala Glu Asp
1               5                   10                  15

Met Ala

<210> SEQ ID NO 84
<211> LENGTH: 19
<212> TYPE: PRT
<213> ORGANISM: Artificial sequence
<220> FEATURE:
<223> OTHER INFORMATION: Synthetic peptide

<400> SEQUENCE: 84

Tyr Pro Ser Lys Pro Asp Asn Pro Gly Glu Asp Ala Pro Ala Glu Asp
1               5                   10                  15

Met Ala Arg

<210> SEQ ID NO 85
<211> LENGTH: 11
<212> TYPE: PRT
<213> ORGANISM: Artificial sequence
<220> FEATURE:
<223> OTHER INFORMATION: Synthetic peptide

<400> SEQUENCE: 85

Tyr Tyr Ser Ala Leu Arg His Tyr Ile Asn Leu
1               5                   10

<210> SEQ ID NO 86
<211> LENGTH: 15
<212> TYPE: PRT
<213> ORGANISM: Artificial sequence
<220> FEATURE:
<223> OTHER INFORMATION: Synthetic peptide

<400> SEQUENCE: 86

Tyr Pro Ser Lys Pro Asp Asn Pro Gly Glu Asp Ala Pro Ala Glu
1               5                   10                  15

<210> SEQ ID NO 87
<211> LENGTH: 16
<212> TYPE: PRT
<213> ORGANISM: Artificial sequence
<220> FEATURE:
<223> OTHER INFORMATION: Synthetic peptide

<400> SEQUENCE: 87

Tyr Pro Ser Lys Pro Asp Asn Pro Gly Glu Asp Ala Pro Ala Glu Asp
1               5                   10                  15

<210> SEQ ID NO 88
<211> LENGTH: 18
<212> TYPE: PRT
<213> ORGANISM: Artificial sequence
<220> FEATURE:
<223> OTHER INFORMATION: Synthetic peptide

<400> SEQUENCE: 88

Pro Ala Glu Asp Met Ala Arg Tyr Tyr Ser Ala Leu Arg His Tyr Ile
1               5                   10                  15

Asn Leu

<210> SEQ ID NO 89
<211> LENGTH: 16
<212> TYPE: PRT
<213> ORGANISM: Artificial sequence
<220> FEATURE:
<223> OTHER INFORMATION: Synthetic peptide

<400> SEQUENCE: 89

Glu Asp Met Ala Arg Tyr Tyr Ser Ala Leu Arg His Tyr Ile Asn Leu
1               5                   10                  15

<210> SEQ ID NO 90
<211> LENGTH: 23
<212> TYPE: PRT
<213> ORGANISM: Artificial sequence
<220> FEATURE:
<223> OTHER INFORMATION: Synthetic peptide

<400> SEQUENCE: 90

Pro Gly Glu Asp Ala Pro Ala Glu Asp Met Ala Arg Tyr Tyr Ser Ala
1               5                   10                  15

Leu Arg His Tyr Ile Asn Leu
            20

<210> SEQ ID NO 91
<211> LENGTH: 17
<212> TYPE: PRT
<213> ORGANISM: Artificial sequence
<220> FEATURE:
<223> OTHER INFORMATION: Synthetic peptide

<400> SEQUENCE: 91

Ser Ser Pro Glu Thr Leu Ile Ser Asp Leu Leu Met Arg Glu Ser Thr
1               5                   10                  15

Glu

<210> SEQ ID NO 92
<211> LENGTH: 17
<212> TYPE: PRT
<213> ORGANISM: Artificial sequence
<220> FEATURE:
<223> OTHER INFORMATION: Synthetic peptide

<400> SEQUENCE: 92

Tyr Pro Ser Lys Pro Asp Asn Pro Gly Glu Asp Ala Pro Ala Glu Asp
1               5                   10                  15

Met

<210> SEQ ID NO 93
<211> LENGTH: 11
<212> TYPE: PRT
<213> ORGANISM: Artificial sequence
<220> FEATURE:

<223> OTHER INFORMATION: Synthetic peptide

<400> SEQUENCE: 93

Ser Ser Pro Glu Thr Leu Ile Ser Asp Leu Leu
1               5                   10

<210> SEQ ID NO 94
<211> LENGTH: 10
<212> TYPE: PRT
<213> ORGANISM: Artificial sequence
<220> FEATURE:
<223> OTHER INFORMATION: Synthetic peptide

<400> SEQUENCE: 94

Tyr Ser Ala Leu Arg His Tyr Ile Asn Leu
1               5                   10

<210> SEQ ID NO 95
<211> LENGTH: 10
<212> TYPE: PRT
<213> ORGANISM: Artificial sequence
<220> FEATURE:
<223> OTHER INFORMATION: Synthetic peptide

<400> SEQUENCE: 95

Ser Pro Glu Thr Leu Ile Ser Asp Leu Leu
1               5                   10

<210> SEQ ID NO 96
<211> LENGTH: 12
<212> TYPE: PRT
<213> ORGANISM: Artificial sequence
<220> FEATURE:
<223> OTHER INFORMATION: Synthetic peptide

<400> SEQUENCE: 96

Ser Ser Pro Glu Thr Leu Ile Ser Asp Leu Leu Met
1               5                   10

<210> SEQ ID NO 97
<211> LENGTH: 17
<212> TYPE: PRT
<213> ORGANISM: Artificial sequence
<220> FEATURE:
<223> OTHER INFORMATION: Synthetic peptide

<400> SEQUENCE: 97

Ala Arg Tyr Tyr Ser Ala Leu Arg His Tyr Ile Asn Leu Ile Thr Arg
1               5                   10                  15

Gln

<210> SEQ ID NO 98
<211> LENGTH: 11
<212> TYPE: PRT
<213> ORGANISM: Artificial sequence
<220> FEATURE:
<223> OTHER INFORMATION: Synthetic peptide

<400> SEQUENCE: 98

Leu Arg His Tyr Ile Asn Leu Ile Thr Arg Gln
1               5                   10

<210> SEQ ID NO 99
<211> LENGTH: 14
<212> TYPE: PRT
<213> ORGANISM: Artificial sequence

```
<220> FEATURE:
<223> OTHER INFORMATION: Synthetic peptide

<400> SEQUENCE: 99

Leu Arg His Tyr Ile Asn Leu Ile Thr Arg Gln Arg Tyr Gly
1               5                   10

<210> SEQ ID NO 100
<211> LENGTH: 22
<212> TYPE: PRT
<213> ORGANISM: Artificial sequence
<220> FEATURE:
<223> OTHER INFORMATION: Synthetic peptide

<400> SEQUENCE: 100

Ser Ser Pro Glu Thr Leu Ile Ser Asp Leu Leu Met Arg Glu Ser Thr
1               5                   10                  15

Glu Asn Val Pro Arg Thr
            20

<210> SEQ ID NO 101
<211> LENGTH: 14
<212> TYPE: PRT
<213> ORGANISM: Artificial sequence
<220> FEATURE:
<223> OTHER INFORMATION: Synthetic peptide

<400> SEQUENCE: 101

Tyr Tyr Ser Ala Leu Arg His Tyr Ile Asn Leu Ile Thr Arg
1               5                   10

<210> SEQ ID NO 102
<211> LENGTH: 16
<212> TYPE: PRT
<213> ORGANISM: Artificial sequence
<220> FEATURE:
<223> OTHER INFORMATION: Synthetic peptide

<400> SEQUENCE: 102

Ser Ala Leu Arg His Tyr Ile Asn Leu Ile Thr Arg Gln Arg Tyr Gly
1               5                   10                  15

<210> SEQ ID NO 103
<211> LENGTH: 25
<212> TYPE: PRT
<213> ORGANISM: Artificial sequence
<220> FEATURE:
<223> OTHER INFORMATION: Synthetic peptide

<400> SEQUENCE: 103

Ser Ser Pro Glu Thr Leu Ile Ser Asp Leu Leu Met Arg Glu Ser Thr
1               5                   10                  15

Glu Asn Val Pro Arg Thr Arg Leu Glu
            20                  25

<210> SEQ ID NO 104
<211> LENGTH: 22
<212> TYPE: PRT
<213> ORGANISM: Artificial sequence
<220> FEATURE:
<223> OTHER INFORMATION: Synthetic peptide

<400> SEQUENCE: 104

Gly Glu Asp Ala Pro Ala Glu Asp Met Ala Arg Tyr Tyr Ser Ala Leu
1               5                   10                  15
```

Arg His Tyr Ile Asn Leu
            20

<210> SEQ ID NO 105
<211> LENGTH: 14
<212> TYPE: PRT
<213> ORGANISM: Artificial sequence
<220> FEATURE:
<223> OTHER INFORMATION: Synthetic peptide

<400> SEQUENCE: 105

Tyr Pro Ser Lys Pro Asp Asn Pro Gly Glu Asp Ala Pro Ala
1               5                   10

<210> SEQ ID NO 106
<211> LENGTH: 16
<212> TYPE: PRT
<213> ORGANISM: Artificial sequence
<220> FEATURE:
<223> OTHER INFORMATION: Synthetic peptide

<400> SEQUENCE: 106

Tyr Ser Ala Leu Arg His Tyr Ile Asn Leu Ile Thr Arg Gln Arg Tyr
1               5                   10                  15

<210> SEQ ID NO 107
<211> LENGTH: 10
<212> TYPE: PRT
<213> ORGANISM: Artificial sequence
<220> FEATURE:
<223> OTHER INFORMATION: Synthetic peptide

<400> SEQUENCE: 107

Ala Arg Tyr Tyr Ser Ala Leu Arg His Tyr
1               5                   10

<210> SEQ ID NO 108
<211> LENGTH: 10
<212> TYPE: PRT
<213> ORGANISM: Artificial sequence
<220> FEATURE:
<223> OTHER INFORMATION: Synthetic peptide

<400> SEQUENCE: 108

Tyr Pro Ser Lys Pro Asp Asn Pro Gly Glu
1               5                   10

<210> SEQ ID NO 109
<211> LENGTH: 13
<212> TYPE: PRT
<213> ORGANISM: Artificial sequence
<220> FEATURE:
<223> OTHER INFORMATION: Synthetic peptide

<400> SEQUENCE: 109

Tyr Pro Ser Lys Pro Asp Asn Pro Gly Glu Asp Ala Pro
1               5                   10

<210> SEQ ID NO 110
<211> LENGTH: 9
<212> TYPE: PRT
<213> ORGANISM: Artificial sequence
<220> FEATURE:
<223> OTHER INFORMATION: Synthetic peptide

<400> SEQUENCE: 110

Glu Ser Thr Glu Asn Val Pro Arg Thr
1               5

<210> SEQ ID NO 111
<211> LENGTH: 12
<212> TYPE: PRT
<213> ORGANISM: Artificial sequence
<220> FEATURE:
<223> OTHER INFORMATION: Synthetic peptide

<400> SEQUENCE: 111

Tyr Pro Ser Lys Pro Asp Asn Pro Gly Glu Asp Ala
1               5                   10

<210> SEQ ID NO 112
<211> LENGTH: 10
<212> TYPE: PRT
<213> ORGANISM: Artificial sequence
<220> FEATURE:
<223> OTHER INFORMATION: Synthetic peptide

<400> SEQUENCE: 112

Tyr Tyr Ser Ala Leu Arg His Tyr Ile Asn
1               5                   10

<210> SEQ ID NO 113
<211> LENGTH: 13
<212> TYPE: PRT
<213> ORGANISM: Artificial sequence
<220> FEATURE:
<223> OTHER INFORMATION: Synthetic peptide

<400> SEQUENCE: 113

Ser Lys Pro Asp Asn Pro Gly Glu Asp Ala Pro Ala Glu
1               5                   10

<210> SEQ ID NO 114
<211> LENGTH: 15
<212> TYPE: PRT
<213> ORGANISM: Artificial sequence
<220> FEATURE:
<223> OTHER INFORMATION: Synthetic peptide

<400> SEQUENCE: 114

Ser Ala Leu Arg His Tyr Ile Asn Leu Ile Thr Arg Gln Arg Tyr
1               5                   10                  15

<210> SEQ ID NO 115
<211> LENGTH: 10
<212> TYPE: PRT
<213> ORGANISM: Artificial sequence
<220> FEATURE:
<223> OTHER INFORMATION: Synthetic peptide

<400> SEQUENCE: 115

Ser Ser Pro Glu Thr Leu Ile Ser Asp Leu
1               5                   10

<210> SEQ ID NO 116
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 116

Arg Tyr Tyr Ser Ala Leu Arg His Tyr Ile Asn Leu Ile Thr Arg
1               5                   10                  15

<210> SEQ ID NO 117
<211> LENGTH: 12
<212> TYPE: PRT
<213> ORGANISM: Artificial sequence
<220> FEATURE:
<223> OTHER INFORMATION: Synthetic peptide

<400> SEQUENCE: 117

Ser Ala Leu Arg His Tyr Ile Asn Leu Ile Thr Arg
1               5                   10

<210> SEQ ID NO 118
<211> LENGTH: 19
<212> TYPE: PRT
<213> ORGANISM: Artificial sequence
<220> FEATURE:
<223> OTHER INFORMATION: Synthetic peptide

<400> SEQUENCE: 118

Ala Pro Ala Glu Asp Met Ala Arg Tyr Tyr Ser Ala Leu Arg His Tyr
1               5                   10                  15

Ile Asn Leu

<210> SEQ ID NO 119
<211> LENGTH: 19
<212> TYPE: PRT
<213> ORGANISM: Artificial sequence
<220> FEATURE:
<223> OTHER INFORMATION: Synthetic peptide

<400> SEQUENCE: 119

Arg Tyr Tyr Ser Ala Leu Arg His Tyr Ile Asn Leu Ile Thr Arg Gln
1               5                   10                  15

Arg Tyr Gly

<210> SEQ ID NO 120
<211> LENGTH: 18
<212> TYPE: PRT
<213> ORGANISM: Artificial sequence
<220> FEATURE:
<223> OTHER INFORMATION: Synthetic peptide

<400> SEQUENCE: 120

Asp Met Ala Arg Tyr Tyr Ser Ala Leu Arg His Tyr Ile Asn Leu Ile
1               5                   10                  15

Thr Arg

<210> SEQ ID NO 121
<211> LENGTH: 19
<212> TYPE: PRT
<213> ORGANISM: Artificial sequence
<220> FEATURE:
<223> OTHER INFORMATION: Synthetic peptide

<400> SEQUENCE: 121

Ala Arg Tyr Tyr Ser Ala Leu Arg His Tyr Ile Asn Leu Ile Thr Arg
1               5                   10                  15

Gln Arg Tyr
```

```
<210> SEQ ID NO 122
<211> LENGTH: 13
<212> TYPE: PRT
<213> ORGANISM: Artificial sequence
<220> FEATURE:
<223> OTHER INFORMATION: Synthetic peptide

<400> SEQUENCE: 122

Tyr Ser Ala Leu Arg His Tyr Ile Asn Leu Ile Thr Arg
1               5                   10

<210> SEQ ID NO 123
<211> LENGTH: 16
<212> TYPE: PRT
<213> ORGANISM: Artificial sequence
<220> FEATURE:
<223> OTHER INFORMATION: Synthetic peptide

<400> SEQUENCE: 123

Ser Ala Leu Arg His Tyr Ile Asn Leu Ile Thr Arg Gln Arg Tyr Gly
1               5                   10                  15

<210> SEQ ID NO 124
<211> LENGTH: 18
<212> TYPE: PRT
<213> ORGANISM: Artificial sequence
<220> FEATURE:
<223> OTHER INFORMATION: Synthetic peptide

<400> SEQUENCE: 124

Arg Tyr Tyr Ser Ala Leu Arg His Tyr Ile Asn Leu Ile Thr Arg Gln
1               5                   10                  15

Arg Tyr

<210> SEQ ID NO 125
<211> LENGTH: 14
<212> TYPE: PRT
<213> ORGANISM: Artificial sequence
<220> FEATURE:
<223> OTHER INFORMATION: Synthetic peptide

<400> SEQUENCE: 125

Ser Ala Leu Arg His Tyr Ile Asn Leu Ile Thr Arg Gln Arg
1               5                   10

<210> SEQ ID NO 126
<211> LENGTH: 23
<212> TYPE: PRT
<213> ORGANISM: Artificial sequence
<220> FEATURE:
<223> OTHER INFORMATION: Synthetic peptide

<400> SEQUENCE: 126

Ala Pro Ala Glu Asp Met Ala Arg Tyr Tyr Ser Ala Leu Arg His Tyr
1               5                   10                  15

Ile Asn Leu Ile Thr Arg Gln
                20

<210> SEQ ID NO 127
<211> LENGTH: 15
<212> TYPE: PRT
<213> ORGANISM: Artificial sequence
<220> FEATURE:
<223> OTHER INFORMATION: Synthetic peptide
```

<400> SEQUENCE: 127

Ser Ala Leu Arg His Tyr Ile Asn Leu Ile Thr Arg Gln Arg Tyr
1               5                   10                  15

<210> SEQ ID NO 128
<211> LENGTH: 14
<212> TYPE: PRT
<213> ORGANISM: Artificial sequence
<220> FEATURE:
<223> OTHER INFORMATION: Synthetic peptide

<400> SEQUENCE: 128

Tyr Tyr Ser Ala Leu Arg His Tyr Ile Asn Leu Ile Thr Arg
1               5                   10

<210> SEQ ID NO 129
<211> LENGTH: 22
<212> TYPE: PRT
<213> ORGANISM: Artificial sequence
<220> FEATURE:
<223> OTHER INFORMATION: Synthetic peptide

<400> SEQUENCE: 129

Asp Met Ala Arg Tyr Tyr Ser Ala Leu Arg His Tyr Ile Asn Leu Ile
1               5                   10                  15

Thr Arg Gln Arg Tyr Gly
            20

<210> SEQ ID NO 130
<211> LENGTH: 19
<212> TYPE: PRT
<213> ORGANISM: Artificial sequence
<220> FEATURE:
<223> OTHER INFORMATION: Synthetic peptide

<400> SEQUENCE: 130

Asp Met Ala Arg Tyr Tyr Ser Ala Leu Arg His Tyr Ile Asn Leu Ile
1               5                   10                  15

Thr Arg Gln

<210> SEQ ID NO 131
<211> LENGTH: 21
<212> TYPE: PRT
<213> ORGANISM: Artificial sequence
<220> FEATURE:
<223> OTHER INFORMATION: Synthetic peptide

<400> SEQUENCE: 131

Ala Glu Asp Met Ala Arg Tyr Tyr Ser Ala Leu Arg His Tyr Ile Asn
1               5                   10                  15

Leu Ile Thr Arg Gln
            20

<210> SEQ ID NO 132
<211> LENGTH: 18
<212> TYPE: PRT
<213> ORGANISM: Artificial sequence
<220> FEATURE:
<223> OTHER INFORMATION: Synthetic peptide

<400> SEQUENCE: 132

Tyr Tyr Ser Ala Leu Arg His Tyr Ile Asn Leu Ile Thr Arg Gln Arg
1               5                   10                  15

Tyr Gly

<210> SEQ ID NO 133
<211> LENGTH: 15
<212> TYPE: PRT
<213> ORGANISM: Artificial sequence
<220> FEATURE:
<223> OTHER INFORMATION: Synthetic peptide

<400> SEQUENCE: 133

Ala Leu Arg His Tyr Ile Asn Leu Ile Thr Arg Gln Arg Tyr Gly
1               5                   10                  15

<210> SEQ ID NO 134
<211> LENGTH: 12
<212> TYPE: PRT
<213> ORGANISM: Artificial sequence
<220> FEATURE:
<223> OTHER INFORMATION: Synthetic peptide

<400> SEQUENCE: 134

Ser Ser Pro Glu Thr Leu Ile Ser Asp Leu Leu Met
1               5                   10

<210> SEQ ID NO 135
<211> LENGTH: 21
<212> TYPE: PRT
<213> ORGANISM: Artificial sequence
<220> FEATURE:
<223> OTHER INFORMATION: Synthetic peptide

<400> SEQUENCE: 135

Ala Pro Ala Glu Asp Met Ala Arg Tyr Tyr Ser Ala Leu Arg His Tyr
1               5                   10                  15

Ile Asn Leu Ile Thr
            20

<210> SEQ ID NO 136
<211> LENGTH: 16
<212> TYPE: PRT
<213> ORGANISM: Artificial sequence
<220> FEATURE:
<223> OTHER INFORMATION: Synthetic peptide

<400> SEQUENCE: 136

Ala Arg Tyr Tyr Ser Ala Leu Arg His Tyr Ile Asn Leu Ile Thr Arg
1               5                   10                  15

<210> SEQ ID NO 137
<211> LENGTH: 20
<212> TYPE: PRT
<213> ORGANISM: Artificial sequence
<220> FEATURE:
<223> OTHER INFORMATION: Synthetic peptide

<400> SEQUENCE: 137

Asp Met Ala Arg Tyr Tyr Ser Ala Leu Arg His Tyr Ile Asn Leu Ile
1               5                   10                  15

Thr Arg Gln Arg
            20

<210> SEQ ID NO 138
<211> LENGTH: 22
<212> TYPE: PRT
<213> ORGANISM: Artificial sequence
<220> FEATURE:
<223> OTHER INFORMATION: Synthetic peptide

<400> SEQUENCE: 138

Ala Pro Ala Glu Asp Met Ala Arg Tyr Tyr Ser Ala Leu Arg His Tyr
1               5                   10                  15

Ile Asn Leu Ile Thr Arg
            20

<210> SEQ ID NO 139
<211> LENGTH: 17
<212> TYPE: PRT
<213> ORGANISM: Artificial sequence
<220> FEATURE:
<223> OTHER INFORMATION: Synthetic peptide

<400> SEQUENCE: 139

Arg Tyr Tyr Ser Ala Leu Arg His Tyr Ile Asn Leu Ile Thr Arg Gln
1               5                   10                  15

Arg

<210> SEQ ID NO 140
<211> LENGTH: 24
<212> TYPE: PRT
<213> ORGANISM: Artificial sequence
<220> FEATURE:
<223> OTHER INFORMATION: Synthetic peptide

<400> SEQUENCE: 140

Ala Glu Asp Met Ala Arg Tyr Tyr Ser Ala Leu Arg His Tyr Ile Asn
1               5                   10                  15

Leu Ile Thr Arg Gln Arg Tyr Gly
            20

<210> SEQ ID NO 141
<211> LENGTH: 15
<212> TYPE: PRT
<213> ORGANISM: Artificial sequence
<220> FEATURE:
<223> OTHER INFORMATION: Synthetic peptide

<400> SEQUENCE: 141

Asp Met Ala Arg Tyr Tyr Ser Ala Leu Arg His Tyr Ile Asn Leu
1               5                   10                  15

<210> SEQ ID NO 142
<211> LENGTH: 20
<212> TYPE: PRT
<213> ORGANISM: Artificial sequence
<220> FEATURE:
<223> OTHER INFORMATION: Synthetic peptide

<400> SEQUENCE: 142

Ala Pro Ala Glu Asp Met Ala Arg Tyr Tyr Ser Ala Leu Arg His Tyr
1               5                   10                  15

Ile Asn Leu Ile
            20

<210> SEQ ID NO 143
<211> LENGTH: 20

```
<212> TYPE: PRT
<213> ORGANISM: Artificial sequence
<220> FEATURE:
<223> OTHER INFORMATION: Synthetic peptide

<400> SEQUENCE: 143

Ala Glu Asp Met Ala Arg Tyr Tyr Ser Ala Leu Arg His Tyr Ile Asn
1               5                   10                  15

Leu Ile Thr Arg
            20

<210> SEQ ID NO 144
<211> LENGTH: 24
<212> TYPE: PRT
<213> ORGANISM: Artificial sequence
<220> FEATURE:
<223> OTHER INFORMATION: Synthetic peptide

<400> SEQUENCE: 144

Ala Pro Ala Glu Asp Met Ala Arg Tyr Tyr Ser Ala Leu Arg His Tyr
1               5                   10                  15

Ile Asn Leu Ile Thr Arg Gln Arg
            20

<210> SEQ ID NO 145
<211> LENGTH: 13
<212> TYPE: PRT
<213> ORGANISM: Artificial sequence
<220> FEATURE:
<223> OTHER INFORMATION: Synthetic peptide

<400> SEQUENCE: 145

Tyr Tyr Ser Ala Leu Arg His Tyr Ile Asn Leu Ile Thr
1               5                   10

<210> SEQ ID NO 146
<211> LENGTH: 25
<212> TYPE: PRT
<213> ORGANISM: Artificial sequence
<220> FEATURE:
<223> OTHER INFORMATION: Synthetic peptide

<400> SEQUENCE: 146

Ala Pro Ala Glu Asp Met Ala Arg Tyr Tyr Ser Ala Leu Arg His Tyr
1               5                   10                  15

Ile Asn Leu Ile Thr Arg Gln Arg Tyr
            20                  25

<210> SEQ ID NO 147
<211> LENGTH: 20
<212> TYPE: PRT
<213> ORGANISM: Artificial sequence
<220> FEATURE:
<223> OTHER INFORMATION: Synthetic peptide

<400> SEQUENCE: 147

Ala Arg Tyr Tyr Ser Ala Leu Arg His Tyr Ile Asn Leu Ile Thr Arg
1               5                   10                  15

Gln Arg Tyr Gly
            20

<210> SEQ ID NO 148
<211> LENGTH: 14
<212> TYPE: PRT
<213> ORGANISM: Artificial sequence
```

<220> FEATURE:
<223> OTHER INFORMATION: Synthetic peptide

<400> SEQUENCE: 148

Ala Leu Arg His Tyr Ile Asn Leu Ile Thr Arg Gln Arg Tyr
1               5                   10

<210> SEQ ID NO 149
<211> LENGTH: 16
<212> TYPE: PRT
<213> ORGANISM: Artificial sequence
<220> FEATURE:
<223> OTHER INFORMATION: Synthetic peptide

<400> SEQUENCE: 149

Tyr Ser Ala Leu Arg His Tyr Ile Asn Leu Ile Thr Arg Gln Arg Tyr
1               5                   10                  15

<210> SEQ ID NO 150
<211> LENGTH: 11
<212> TYPE: PRT
<213> ORGANISM: Artificial sequence
<220> FEATURE:
<223> OTHER INFORMATION: Synthetic peptide

<400> SEQUENCE: 150

Ser Pro Glu Thr Leu Ile Ser Asp Leu Leu Met
1               5                   10

<210> SEQ ID NO 151
<211> LENGTH: 12
<212> TYPE: PRT
<213> ORGANISM: Artificial sequence
<220> FEATURE:
<223> OTHER INFORMATION: Synthetic peptide

<400> SEQUENCE: 151

Arg Tyr Tyr Ser Ala Leu Arg His Tyr Ile Asn Leu
1               5                   10

<210> SEQ ID NO 152
<211> LENGTH: 16
<212> TYPE: PRT
<213> ORGANISM: Artificial sequence
<220> FEATURE:
<223> OTHER INFORMATION: Synthetic peptide

<400> SEQUENCE: 152

Tyr Tyr Ser Ala Leu Arg His Tyr Ile Asn Leu Ile Thr Arg Gln Arg
1               5                   10                  15

<210> SEQ ID NO 153
<211> LENGTH: 11
<212> TYPE: PRT
<213> ORGANISM: Artificial sequence
<220> FEATURE:
<223> OTHER INFORMATION: Synthetic peptide

<400> SEQUENCE: 153

Ser Ser Pro Glu Thr Leu Ile Ser Asp Leu Leu
1               5                   10

<210> SEQ ID NO 154
<211> LENGTH: 10
<212> TYPE: PRT
<213> ORGANISM: Artificial sequence
<220> FEATURE:

```
<223> OTHER INFORMATION: Synthetic peptide

<400> SEQUENCE: 154

Ser Pro Glu Thr Leu Ile Ser Asp Leu Leu
1               5                   10

<210> SEQ ID NO 155
<211> LENGTH: 21
<212> TYPE: PRT
<213> ORGANISM: Artificial sequence
<220> FEATURE:
<223> OTHER INFORMATION: Synthetic peptide

<400> SEQUENCE: 155

Ser Ser Pro Glu Thr Leu Ile Ser Asp Leu Leu Met Arg Glu Ser Thr
1               5                   10                  15

Glu Asn Val Pro Arg
            20

<210> SEQ ID NO 156
<211> LENGTH: 13
<212> TYPE: PRT
<213> ORGANISM: Artificial sequence
<220> FEATURE:
<223> OTHER INFORMATION: Synthetic peptide

<400> SEQUENCE: 156

Ser Ala Leu Arg His Tyr Ile Asn Leu Ile Thr Arg Gln
1               5                   10

<210> SEQ ID NO 157
<211> LENGTH: 24
<212> TYPE: PRT
<213> ORGANISM: Artificial sequence
<220> FEATURE:
<223> OTHER INFORMATION: Synthetic peptide

<400> SEQUENCE: 157

Ile Ser Asp Leu Leu Met Arg Glu Ser Thr Glu Asn Val Pro Arg Thr
1               5                   10                  15

Arg Leu Glu Asp Pro Ala Met Trp
            20

<210> SEQ ID NO 158
<211> LENGTH: 17
<212> TYPE: PRT
<213> ORGANISM: Artificial sequence
<220> FEATURE:
<223> OTHER INFORMATION: Synthetic peptide

<400> SEQUENCE: 158

Tyr Tyr Ser Ala Leu Arg His Tyr Ile Asn Leu Ile Thr Arg Gln Arg
1               5                   10                  15

Tyr

<210> SEQ ID NO 159
<211> LENGTH: 25
<212> TYPE: PRT
<213> ORGANISM: Artificial sequence
<220> FEATURE:
<223> OTHER INFORMATION: Synthetic peptide

<400> SEQUENCE: 159

Asp Met Ala Arg Tyr Tyr Ser Ala Leu Arg His Tyr Ile Asn Leu Ile
1               5                   10                  15
```

```
Thr Arg Gln Arg Tyr Gly Lys Arg Ser
            20                  25

<210> SEQ ID NO 160
<211> LENGTH: 14
<212> TYPE: PRT
<213> ORGANISM: Artificial sequence
<220> FEATURE:
<223> OTHER INFORMATION: Synthetic peptide

<400> SEQUENCE: 160

Arg Tyr Tyr Ser Ala Leu Arg His Tyr Ile Asn Leu Ile Thr
1               5                   10

<210> SEQ ID NO 161
<211> LENGTH: 23
<212> TYPE: PRT
<213> ORGANISM: Artificial sequence
<220> FEATURE:
<223> OTHER INFORMATION: Synthetic peptide

<400> SEQUENCE: 161

Ala Glu Asp Met Ala Arg Tyr Tyr Ser Ala Leu Arg His Tyr Ile Asn
1               5                   10                  15

Leu Ile Thr Arg Gln Arg Tyr
            20

<210> SEQ ID NO 162
<211> LENGTH: 10
<212> TYPE: PRT
<213> ORGANISM: Artificial sequence
<220> FEATURE:
<223> OTHER INFORMATION: Synthetic peptide

<400> SEQUENCE: 162

Pro Ser Lys Pro Asp Asn Pro Gly Glu Asp
1               5                   10

<210> SEQ ID NO 163
<211> LENGTH: 10
<212> TYPE: PRT
<213> ORGANISM: Artificial sequence
<220> FEATURE:
<223> OTHER INFORMATION: Synthetic peptide

<400> SEQUENCE: 163

Val Ile Leu Lys Lys Ala Thr Glu Tyr Val
1               5                   10

<210> SEQ ID NO 164
<211> LENGTH: 9
<212> TYPE: PRT
<213> ORGANISM: Artificial sequence
<220> FEATURE:
<223> OTHER INFORMATION: Synthetic peptide

<400> SEQUENCE: 164

Gly Ala Asp Gly Val Gly Lys Ser Ala
1               5
```